ns009234069B2

(12) United States Patent
Nakagawa et al.

(10) Patent No.: US 9,234,069 B2
(45) Date of Patent: Jan. 12, 2016

(54) PENTAMETHYLENEDIISOCYANATE, METHOD FOR PRODUCING PENTAMETHYLENEDIISOCYANATE, POLYISOCYANATE COMPOSITION, POLYURETHANE RESIN, AND POLYUREA RESIN

(75) Inventors: Toshihiko Nakagawa, Ichihara (JP); Hiroshi Takeuchi, Ichihara (JP); Kuniaki Sato, Ichihara (JP); Satoshi Yamasaki, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 14/001,837

(22) PCT Filed: Mar. 7, 2012

(86) PCT No.: PCT/JP2012/055821
§ 371 (c)(1),
(2), (4) Date: Aug. 27, 2013

(87) PCT Pub. No.: WO2012/121291
PCT Pub. Date: Sep. 13, 2012

(65) Prior Publication Data
US 2013/0338330 A1    Dec. 19, 2013

(30) Foreign Application Priority Data
Mar. 9, 2011 (JP) .................................. 2011-051505

(51) Int. Cl.
*C08G 18/73*    (2006.01)
*C07C 265/04*    (2006.01)
(Continued)

(52) U.S. Cl.
CPC .............. *C08G 18/73* (2013.01); *C07C 263/10* (2013.01); *C07C 265/04* (2013.01);
(Continued)

(58) Field of Classification Search
CPC .. C07C 263/10; C07C 265/04; C07C 265/14; C08G 18/73
See application file for complete search history.

(56) References Cited

U.S. PATENT DOCUMENTS

2009/0292100 A1    11/2009    Fiene et al.
(Continued)

FOREIGN PATENT DOCUMENTS

CN    101981202 A    2/2011
(Continued)

OTHER PUBLICATIONS

International Search Report PCT/JP2012/055821 dated May 29, 2012.
(Continued)

*Primary Examiner* — Michael L Leonard
(74) *Attorney, Agent, or Firm* — Foley & Lardner LLP

(57) ABSTRACT

A Pentamethylene diisocyanate is obtained by phosgenating pentamethylenediamine or its salt obtained by a biochemical method, and contains 5 to 400 ppm of a compound represented by the general formula (1) below and a compound represented by the general formula (2) below in total:

[Chemical Formula 1]

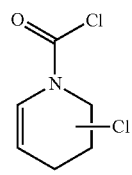

(1)

[Chemical Formula 2]

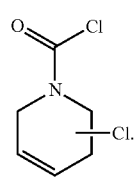

(2)

4 Claims, 9 Drawing Sheets

(51) Int. Cl.

| | |
|---|---|
| *C07C 263/10* | (2006.01) |
| *C07C 265/14* | (2006.01) |
| *C08G 18/48* | (2006.01) |
| *C08G 18/62* | (2006.01) |
| *C08G 18/75* | (2006.01) |
| *C08G 18/79* | (2006.01) |
| *C08G 18/02* | (2006.01) |
| *C08G 18/10* | (2006.01) |
| *C08G 18/40* | (2006.01) |
| *C08G 18/42* | (2006.01) |
| *C12P 13/00* | (2006.01) |

(52) U.S. Cl.
 CPC ........... *C07C 265/14* (2013.01); *C08G 18/022* (2013.01); *C08G 18/10* (2013.01); *C08G 18/4063* (2013.01); *C08G 18/4211* (2013.01); *C08G 18/4216* (2013.01); *C08G 18/4288* (2013.01); *C08G 18/4808* (2013.01); *C08G 18/4825* (2013.01); *C08G 18/4854* (2013.01); *C08G 18/6225* (2013.01); *C08G 18/755* (2013.01); *C08G 18/792* (2013.01); *C12P 13/001* (2013.01); *C12Y 401/01018* (2013.01)

(56) References Cited

U.S. PATENT DOCUMENTS

| | | | |
|---|---|---|---|
| 2010/0022707 A1 * | 1/2010 | Schaefer et al. | ............... 524/612 |
| 2010/0204430 A1 | 8/2010 | Marc et al. | |
| 2010/0292429 A1 | 11/2010 | Volkert et al. | |
| 2012/0010427 A1 | 1/2012 | Hamada et al. | |
| 2013/0079486 A1 | 3/2013 | Hidesaki et al. | |

FOREIGN PATENT DOCUMENTS

| | | | | |
|---|---|---|---|---|
| JP | 2003-252846 A | 9/2003 | | |
| JP | 2003-292612 A | 10/2003 | | |
| JP | 2004-000114 A | 1/2004 | | |
| JP | 2004-208646 A | 7/2004 | | |
| JP | 2004-222569 A | 8/2004 | | |
| JP | 2005-006650 A | 1/2005 | | |
| JP | 2005-048179 A | 2/2005 | | |
| JP | 2006-348057 A | 12/2006 | | |
| JP | 2009-131239 A | 6/2009 | | |
| JP | 2009-155284 A | 7/2009 | | |
| JP | 2009-54553 | 12/2009 | | |
| JP | 2010-254764 | 11/2010 | | |
| JP | 2010254764 A | * | 11/2010 | ............. C08G 18/79 |
| JP | 2011-201863 | 10/2011 | | |
| JP | 2011-201864 | 10/2011 | | |
| JP | 2012-152202 A | 8/2012 | | |
| KR | 10-2010-0075905 A | 7/2010 | | |
| WO | WO-2010/110142 A1 | 9/2010 | | |
| WO | WO 2011/108473 A1 | 9/2011 | | |

OTHER PUBLICATIONS

Japanese Office Action dated Sep. 16, 2014 issued in Application No. 2013-503579.

International Preliminary Report on Patentability and Written Opinion in PCT/JP2012/055821 dated Sep. 19, 2013.

Office Action received in Chinese Patent Application No. 201280005547.X dated Jun. 16, 2014.

Office Action issued in Korean Patent Application No. 10-2013-7023268 dated Jan. 14, 2015.

Office Action issued in Japanese Patent Application No. 2013-503579 dated Apr. 21, 2015.

* cited by examiner

SEQUENCE LISTING

```
<160> NUMBER OF SEQ ID NOS: 4

<210> SEQ ID NO 1
<211> LENGTH: 47
<212> TYPE: DNA
<213> ORGANISM: Artificial
<220> FEATURE:
<223> OTHER INFORMATION: Primer

<400> SEQUENCE: 1
aaggtaccac aaaaaggata aaacaatgaa cgttattgca atattga                47

<210> SEQ ID NO 2
<211> LENGTH: 30
<212> TYPE: DNA
<213> ORGANISM: Artificial
<220> FEATURE:
<223> OTHER INFORMATION: Primer

<400> SEQUENCE: 2
```

```
agtctagatt attttttgct ttcttctttc                                             30
```

<210> SEQ ID NO 3
<211> LENGTH: 2177
<212> TYPE: DNA
<213> ORGANISM: Escherichia coli
<220> FEATURE:
<221> NAME/KEY: CDS
<222> LOCATION: (24)..(2171)

<400> SEQUENCE: 3

```
ggtaccacaa aaggataaa aca atg aac gtt att gca ata ttg aat cac atg         53
                         Met Asn Val Ile Ala Ile Leu Asn His Met
                           1               5                  10 ggg gtt tat ttt aaa gaa gaa ccc atc cgt gaa ctt cat cgc gcg ctt         101
Gly Val Tyr Phe Lys Glu Glu Pro Ile Arg Glu Leu His Arg Ala Leu
                 15                  20                  25 gaa cgt ctg aac ttc cag att gtt tac ccg aac gac cgt gac gac tta         149
Glu Arg Leu Asn Phe Gln Ile Val Tyr Pro Asn Asp Arg Asp Asp Leu
             30                  35                  40 tta aaa ctg atc gaa aac aat gcg cgt ctg tgc ggc gtt att ttt gac         197
Leu Lys Leu Ile Glu Asn Asn Ala Arg Leu Cys Gly Val Ile Phe Asp
         45                  50                  55 tgg gat aaa tat aat ctc gag ctg tgc gaa gaa att agc aaa atg aac         245
Trp Asp Lys Tyr Asn Leu Glu Leu Cys Glu Glu Ile Ser Lys Met Asn
     60                  65                  70 gag aac ctg ccg ttg tac gcg ttc gct aat acg tat tcc act ctc gat         293
Glu Asn Leu Pro Leu Tyr Ala Phe Ala Asn Thr Tyr Ser Thr Leu Asp
 75                  80                  85                  90 gta agc ctg aat gac ctg cgt tta cag att agc ttc ttt gaa tat gcg         341
Val Ser Leu Asn Asp Leu Arg Leu Gln Ile Ser Phe Phe Glu Tyr Ala
                 95                 100                 105 ctg ggt gct gct gaa gat att gct aat aag atc aag cag acc act gac         389
Leu Gly Ala Ala Glu Asp Ile Ala Asn Lys Ile Lys Gln Thr Thr Asp
            110                 115                 120 gaa tat atc aac act att ctg cct ccg ctg act aaa gca ctg ttt aaa         437
Glu Tyr Ile Asn Thr Ile Leu Pro Pro Leu Thr Lys Ala Leu Phe Lys
            125                 130                 135 tat gtt cgt gaa ggt aaa tat act ttc tgt act cct ggt cac atg ggc         485
Tyr Val Arg Glu Gly Lys Tyr Thr Phe Cys Thr Pro Gly His Met Gly
140                 145                 150 ggt act gca ttc cag aaa agc ccg gta ggt agc ctg ttc tat gat ttc         533
Gly Thr Ala Phe Gln Lys Ser Pro Val Gly Ser Leu Phe Tyr Asp Phe
155                 160                 165                 170 ttt ggt ccg aat acc atg aaa tct gat att tcc att tca gta tct gaa         581
Phe Gly Pro Asn Thr Met Lys Ser Asp Ile Ser Ile Ser Val Ser Glu
                175                 180                 185 ctg ggt tct ctg ctg gat cac agt ggt cca cac aaa gaa gca gaa cag         629
Leu Gly Ser Leu Leu Asp His Ser Gly Pro His Lys Glu Ala Glu Gln
            190                 195                 200 tat atc gct cgc gtc ttt aac gca gac cgc agc tac atg gtg acc aac         677
Tyr Ile Ala Arg Val Phe Asn Ala Asp Arg Ser Tyr Met Val Thr Asn
            205                 210                 215 ggt act tcc act gcg aac aaa att gtt ggt atg tac tct gct cca gca         725
Gly Thr Ser Thr Ala Asn Lys Ile Val Gly Met Tyr Ser Ala Pro Ala
        220                 225                 230 ggc agc acc att ctg att gac cgt aac tgc cac aaa tcg ctg acc cac         773
Gly Ser Thr Ile Leu Ile Asp Arg Asn Cys His Lys Ser Leu Thr His
235                 240                 245                 250 ctg atg atg atg agc gat gtt acg cca atc tat ttc cgc ccg acc cgt         821
Leu Met Met Met Ser Asp Val Thr Pro Ile Tyr Phe Arg Pro Thr Arg
```

-continued

```
                  255                 260                 265
aac gct tac ggt att ctt ggt ggt atc cca cag agt gaa ttc cag cac       869
Asn Ala Tyr Gly Ile Leu Gly Gly Ile Pro Gln Ser Glu Phe Gln His
        270                 275                 280 gct acc att gct aag cgc gtg aaa gaa aca cca aac gca acc tgg ccg       917
Ala Thr Ile Ala Lys Arg Val Lys Glu Thr Pro Asn Ala Thr Trp Pro
            285                 290                 295 gta cat gct gta att acc aac tct acc tat gat ggt ctg ctg tac aac       965
Val His Ala Val Ile Thr Asn Ser Thr Tyr Asp Gly Leu Leu Tyr Asn
    300                 305                 310 acc gac ttc atc aag aaa aca ctg gat gtg aaa tcc atc cac ttt gac      1013
Thr Asp Phe Ile Lys Lys Thr Leu Asp Val Lys Ser Ile His Phe Asp
315                 320                 325                 330 tcc gcg tgg gtg cct tac acc aac ttc tca ccg att tac gaa ggt aaa      1061
Ser Ala Trp Val Pro Tyr Thr Asn Phe Ser Pro Ile Tyr Glu Gly Lys
            335                 340                 345 tgc ggt atg agc ggt ggc cgt gta gaa ggg aaa gtg att tac gaa acc      1109
Cys Gly Met Ser Gly Gly Arg Val Glu Gly Lys Val Ile Tyr Glu Thr
    350                 355                 360 cag tcc act cac aaa ctg ctg gcg gcg ttc tct cag gct tcc atg atc      1157
Gln Ser Thr His Lys Leu Leu Ala Ala Phe Ser Gln Ala Ser Met Ile
        365                 370                 375 cac gtt aaa ggt gac gta aac gaa gaa acc ttt aac gaa gcc tac atg      1205
His Val Lys Gly Asp Val Asn Glu Glu Thr Phe Asn Glu Ala Tyr Met
            380                 385                 390 atg cac acc acc act tct ccg cac tac ggt atc gtg gcg tcc act gaa      1253
Met His Thr Thr Thr Ser Pro His Tyr Gly Ile Val Ala Ser Thr Glu
395                 400                 405                 410 acc gct gcg gcg atg atg aaa ggc aat gca ggt aag cgt ctg atc aac      1301
Thr Ala Ala Ala Met Met Lys Gly Asn Ala Gly Lys Arg Leu Ile Asn
            415                 420                 425 ggt tct att gaa cgt gcg atc aaa ttc cgt aaa gag atc aaa cgt ctg      1349
Gly Ser Ile Glu Arg Ala Ile Lys Phe Arg Lys Glu Ile Lys Arg Leu
        430                 435                 440 aga acg gaa tct gat ggc tgg ttc ttt gat gta tgg cag ccg gat cat      1397
Arg Thr Glu Ser Asp Gly Trp Phe Phe Asp Val Trp Gln Pro Asp His
            445                 450                 455 atc gat acg act gaa tgc tgg ccg ctg cgt tct gac agc acc tgg cac      1445
Ile Asp Thr Thr Glu Cys Trp Pro Leu Arg Ser Asp Ser Thr Trp His
    460                 465                 470 ggc ttc aaa aac atc gat aac gag cac atg tat ctt gac ccg atc aaa      1493
Gly Phe Lys Asn Ile Asp Asn Glu His Met Tyr Leu Asp Pro Ile Lys
475                 480                 485                 490 gtc acc ctg ctg act ccg ggg atg gaa aaa gac ggc acc atg agc gac      1541
Val Thr Leu Leu Thr Pro Gly Met Glu Lys Asp Gly Thr Met Ser Asp
            495                 500                 505 ttt ggt att ccg gcc agc atc gtg gcg aaa tac ctc gac gaa cat ggc      1589
Phe Gly Ile Pro Ala Ser Ile Val Ala Lys Tyr Leu Asp Glu His Gly
        510                 515                 520 atc gtt gtt gag aaa acc ggt ccg tat aac ctg ctg ttc ctg ttc agc      1637
Ile Val Val Glu Lys Thr Gly Pro Tyr Asn Leu Leu Phe Leu Phe Ser
            525                 530                 535 atc ggt atc gat aag acc aaa gca ctg agc ctg ctg cgt gct ctg act      1685
Ile Gly Ile Asp Lys Thr Lys Ala Leu Ser Leu Leu Arg Ala Leu Thr
    540                 545                 550 gac ttt aaa cgt gcg ttc gac ctg aac ctg cgt gtg aaa aac atg ctg      1733
Asp Phe Lys Arg Ala Phe Asp Leu Asn Leu Arg Val Lys Asn Met Leu
555                 560                 565                 570 ccg tct ctg tat cgt gaa gat cct gaa ttc tat gaa aac atg cgt att      1781
```

```
                Pro Ser Leu Tyr Arg Glu Asp Pro Glu Phe Tyr Glu Asn Met Arg Ile
                            575                 580                 585 cag gaa ctg gct cag aat atc cac aaa ctg att gtt cac cac aat ctg              1829
Gln Glu Leu Ala Gln Asn Ile His Lys Leu Ile Val His His Asn Leu
                590                 595                 600 ccg gat ctg atg tat cgc gca ttt gaa gtg ctg ccg acg atg gta atg              1877
Pro Asp Leu Met Tyr Arg Ala Phe Glu Val Leu Pro Thr Met Val Met
            605                 610                 615 act ccg tat gct gca ttc cag aaa gag ctg cac ggt atg acc gaa gaa              1925
Thr Pro Tyr Ala Ala Phe Gln Lys Glu Leu His Gly Met Thr Glu Glu
        620                 625                 630 gtt tac ctc gac gaa atg gta ggt cgt att aac gcc aat atg atc ctt              1973
Val Tyr Leu Asp Glu Met Val Gly Arg Ile Asn Ala Asn Met Ile Leu
635                 640                 645                 650 ccg tac ccg ccg gga gtt cct ctg gta atg ccg ggt gaa atg atc acc              2021
Pro Tyr Pro Pro Gly Val Pro Leu Val Met Pro Gly Glu Met Ile Thr
                655                 660                 665 gaa gaa agc cgt ccg gtt ctg gag ttc ctg cag atg ctg tgt gaa atc              2069
Glu Glu Ser Arg Pro Val Leu Glu Phe Leu Gln Met Leu Cys Glu Ile
            670                 675                 680 ggc gct cac tat ccg ggc ttt gaa acc gat att cac ggt gca tac cgt              2117
Gly Ala His Tyr Pro Gly Phe Glu Thr Asp Ile His Gly Ala Tyr Arg
        685                 690                 695 cag gct gat ggc cgc tat acc gtt aag gta ttg aaa gaa gaa agc aaa              2165
Gln Ala Asp Gly Arg Tyr Thr Val Lys Val Leu Lys Glu Glu Ser Lys
    700                 705                 710 aaa taa tctaga                                                                2177
Lys
715

<210> SEQ ID NO 4
<211> LENGTH: 715
<212> TYPE: PRT
<213> ORGANISM: Escherichia coli

<400> SEQUENCE: 4

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175
```

```
Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
            290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590
```

```
Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
        610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715
```

PENTAMETHYLENEDIISOCYANATE, METHOD FOR PRODUCING PENTAMETHYLENEDIISOCYANATE, POLYISOCYANATE COMPOSITION, POLYURETHANE RESIN, AND POLYUREA RESIN

TECHNICAL FIELD

The present invention relates to pentamethylene diisocyanate and a production method thereof a polyisocyanate composition and a polyurethane resin; in particular, the present invention relates to pentamethylene diisocyanate and a production method thereof a polyisocyanate composition obtained from the pentamethylene diisocyanate, a polyurethane resin obtained from pentamethylene diisocyanate or a polyisocyanate composition, and a polyurea resin obtained from the pentamethylene diisocyanate.

BACKGROUND ART

Pentamethylene diisocyanate (PDI), and a modified substance (e.g., a polyisocyanate composition such as isocyanurate) obtained by modifying pentamethylene diisocyanate are used as a material of for example, polyurethane resins.

Pentamethylene diisocyanate is produced, industrially, for example, by phosgenation of pentamethylenediamine (PDA). Pentamethylenediamine, i.e., a material of pentamethylene diisocyanate, is produced, for example, by biochemical methods such as fermentation and enzymatic methods.

As such a method for producing pentamethylenediamine and pentamethylene diisocyanate, to be specific, Patent Document 1 below has proposed, for example, a production of pentamethylene diisocyanate by decarboxylation of lysine with enzyme to prepare an aqueous hydrochloride solution of diaminopentane, and then precipitation in an organic solvent, removal and purification, and thereafter, phosgenation in a liquid phase or a gas phase. Patent Document 1 below also describes that pentamethylene diisocyanate is produced such that the hydrolyzable chlorine content is below 10 ppm.

Furthermore, Patent Document 2 below has proposed, for example, that use of pentamethylene diisocyanate having a hydrolyzable chlorine concentration of 100 ppm or less allows production of a modified substance (polyisocyanurate composition) having excellent storage stability at low costs.

CITATION LIST

Patent Document

Patent Document 1 Japanese Unexamined Patent Application Publication No. 2009-545553
Patent Document 2 Japanese Unexamined Patent Publication No. 2010-254764

SUMMARY OF THE INVENTION

Problem to be Solved by the Invention

However, even if the hydrolyzable chlorine concentration is simply reduced as described in Patent Document 1 and Patent Document 2 above, when pentamethylene diisocyanate is modified, sufficient modification velocity cannot be ensured, and reaction has to be conducted for a long period of time in the presence of a large amount of catalyst, and therefore, increase in costs is inevitable.

Moreover, a modified substance obtained by using pentamethylene diisocyanate in which hydrolyzable chlorine concentration is simply reduced is, for example, poor in storage stability. To be specific, when the modified substance is exposed to a high temperature environment, side reaction is caused to reduce the isocyanate group content, and furthermore, for example, disadvantages such as a great degree of changes in color and viscosity may be caused.

Furthermore, a polyurethane resin, and a polyurea resin obtained by using such pentamethylene diisocyanate or a modified substance thereof may have poor physical properties that are required industrially.

An object of the present invention is to provide a pentamethylene diisocyanate that allows production of a polyisocyanate composition having excellent storage stability and a polyurethane resin having excellent physical properties for low costs and a production method thereof; a polyisocyanate composition obtained from the pentamethylene diisocyanate; a polyurethane resin obtained from the pentamethylene diisocyanate or polyisocyanate composition; and a polyurea resin obtained from the pentamethylene diisocyanate.

Means for Solving the Problem

To achieve the above-described object, a pentamethylene diisocyanate of the present invention is obtained by phosgenating pentamethylenediamine or its salt obtained by a biochemical method, and contains 5 to 400 ppm of a compound represented by the general formula (1) below and a compound represented by the general formula (2) below in total:

[Chemical Formula 1]

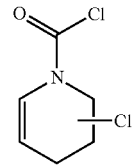

(1)

[Chemical Formula 2]

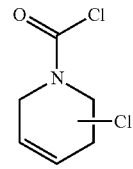

(2)

It is preferable that the pentamethylene diisocyanate of the present invention is obtained by
preparing an aqueous solution of pentamethylenediamine or its salt by a biochemical method,
extracting the pentamethylenediamine or its salt from the aqueous solution, and
phosgenating the extracted pentamethylenediamine or its salt to produce a pentamethylene diisocyanate; and
heating the pentamethylene diisocyanate in the presence of an inactive gas at 180° C. to 245° C., and thereafter, purifying the pentamethylene diisocyanate by distillation.

It is preferable that the pentamethylene diisocyanate of the present invention is obtained by heating the pentamethylene diisocyanate in the presence of a phosphorus-containing compound.

A method for producing pentamethylene diisocyanate of the present invention is a method for producing a pentamethylene diisocyanate containing 5 to 400 ppm of the above-described compound represented by general formula (1) and the above-described compound represented by general formula (2) in total, the method including:

preparing an aqueous solution of pentamethylenediamine or its salt by a biochemical method, extracting the pentamethylenediamine or its salt from the aqueous solution, phosgenating the extracted pentamethylenediamine or its salt to produce a pentamethylene diisocyanate, and heating the pentamethylene diisocyanate in the presence of an inactive gas at 180° C. to 245° C., and thereafter, purifying the pentamethylene diisocyanate by distillation.

In the method for producing pentamethylene diisocyanate of the present invention, it is preferable that the pentamethylene diisocyanate is heated in the presence of a phosphorus-containing compound.

A polyisocyanate composition of the present invention is produced by modifying the above-described pentamethylene diisocyanate, and contains at least one functional group of (a) to (e) below:
- (a) an isocyanurate group,
- (b) an allophanate group,
- (c) a biuret group,
- (d) a urethane group, and
- (e) a urea group.

A polyurethane resin of the present invention is produced by allowing the above-described pentamethylene diisocyanate and/or the above-described polyisocyanate composition, to react with an active hydrogen compound.

In the polyurethane resin of the present invention, it is preferable that the active hydrogen compound is derived from plants.

A polyurea resin of the present invention is produced by allowing the above-described pentamethylene diisocyanate to react with polyamine.

Effects of the Invention

Pentamethylene diisocyanate of the present invention allows production of a polyisocyanate composition with excellent storage stability, and production of a polyurethane resin with various excellent physical properties at low costs.

Therefore, a polyisocyanate composition produced by using pentamethylene diisocyanate of the present invention is excellent in storage stability, and a polyurethane resin and a polyurea resin produced by using the pentamethylene diisocyanate and/or polyisocyanate composition are excellent in various physical properties.

Thus, such a polyurethane resin and a polyurea resin can be used widely in various industrial fields.

EMBODIMENT OF THE INVENTION

Figure 1:
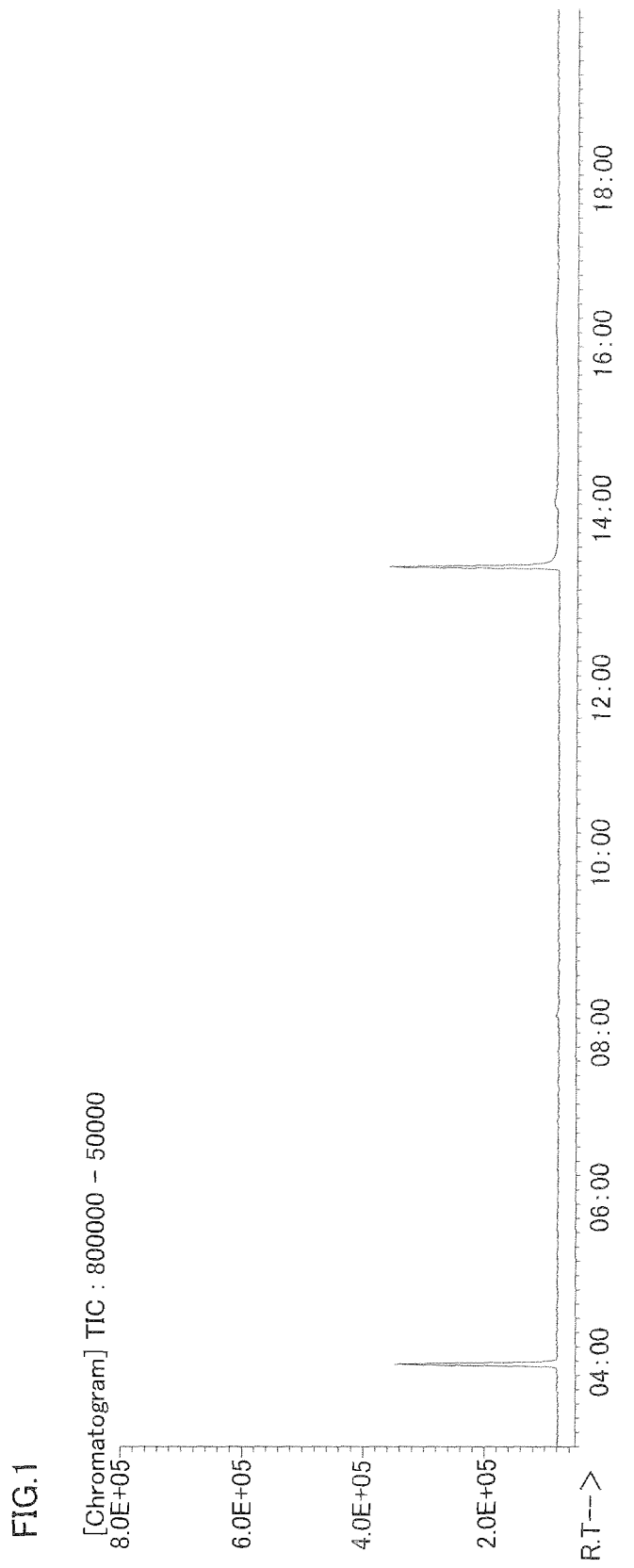
FIG. 1 shows a chromatogram of GC-MS analysis 1 in structural analysis of an unknown substance.

Pentamethylenediisocyanate (PDI) of the present invention is produced by phosgenating pentamethylenediamine (PDA) or its salt obtained by a biochemical method.

Examples of the biochemical method include an enzyme method by enzyme reaction (e.g., lysine decarboxylation in water, etc.), and fermentation method by fermentation (e.g., microbe fermentation of glucose, etc.).

As the biochemical method, preferably, an enzyme method, to be more specific, lysine decarboxylation in water is used.

In lysine decarboxylation, lysine decarboxylase acts on lysine (chemical formula: $NH_2(CH_2)_4CH(NH_2)COOH$, also called: 1,5-pentamethylenediamine-1-carboxylic acid).

Examples of lysine include L-lysine.

As the lysine, lysine salts can also be used.

Examples of lysine salts include organic salts such as carboxylate (e.g., formate, acetate, adipate, oxalate, 2-ethylhexanoate, stearate, sebacate, succinate, etc.), and sulfonate; and inorganic salts such as nitrate, sulfate, hydrochloride, phosphate, carbonate, and hydrogencarbonate.

As the lysine salt, preferably, lysine hydrochloride, or lysine carbonate is used, and more preferably, lysine hydrochloride is used.

Examples of such lysine hydrochloride include L-lysine•monohydrochloride.

The lysine (or its salt) concentration is not particularly limited, and for example, 10 to 700 g/L, preferably 20 to 500 g/L.

Lysine decarboxylase is an enzyme that converts lysine (or its salt) to pentamethylenediamine (or its salt), and is not particularly limited. Examples of lysine decarboxylases include those derived from a known organism. Specific examples of lysine decarboxylases include those derived from microorganism, such as *Bacillus halodurans, Bacillus subtilis, Escherichia coli, Selenomonas ruminantium, Vibrio cholerae, Vibrio parahaemolyticus, Streptomyces coelicolor, Streptomyces pilosus, Eikenella corrodens, Eubacterium acidaminophilurn, Salmonella typhimurium, Hafnia alvei, Neisseria meningitidis, Thermoplasma acidophilum, Pyrococcus abyssi*, and *Corynebacterium glutamicum*. In view of safety, preferably, those derived from *Escherichia coli* is used.

Lysine decarboxylase can be produced by a known method, for example, in conformity with the description of Japanese Unexamined Patent Publication No. 2004-114 (e.g., paragraphs [0015] to [0042], etc.).

Lysine decarboxylase can be produced, to be more specific, for example, by a method in which recombinant cells (hereinafter internal expression cell) that highly express lysine decarboxylase in cells are cultured in a known medium, and thereafter, the proliferated internal expression cell are collected and disrupted, or a method in which recombinant cells (hereinafter surface expression cell) having lysine decarboxylase localized on the cell surface are cultured in a known medium, and thereafter, the proliferated surface expression cells are collected, and as necessary disrupted.

In such a method, the recombinant cells are not particularly limited, and examples thereof include those derived from microorganisms, animals, plants, or insects.

To be more specific, for example, when animals are used, such examples include mise, rats, and cultured cells thereof; when plants are used, such examples include *Arabidopsis thaliana, Nicotiana tabacum*, and cultured cells thereof; when insects are used, such examples include *Bombyx* and cultured cells thereof; and when microorganisms are used, such examples include *Escherichia coli*.

These recombinant cells may be used singly or in a combination of two or more.

The method for localizing lysine decarboxylase on the recombinant cell surface is not particularly limited, and for example, a known method such as a method in which DNA having a portion of secretion signal sequences, gene sequence that codes a portion of cell surface localized protein, and structural gene sequence of lysine decarboxylase in this order is introduced into *Escherichia coli* can be used.

The portion of secretion signal sequences is not particularly limited, as long as it is a necessary sequence for allowing protein secretion in the host, and for example, in *Escherichia coli*, a portion of lipoprotein sequence, to be more specific, for example, a gene sequence translated into, as an amino acid sequence, MKATKLVLGAVILGSTLLAGCSSNAKIDQ (amino acid represented by one letter).

The gene sequence that codes a portion of cell surface localized protein is not particularly limited, and in *Escherichia coli* for example, a portion of outer membrane fusion protein sequence, to be more specific, for example, the portion of 46th to 159th amino acids of the sequence of OmpA (outer membrane protein A) is used.

The method for cloning lysine decarboxylase gene, lipoprotein gene, and OmpA gene is not particularly limited, and examples include a method in which necessary genetic region is amplified and obtained based on known gene information by PCR (polymerase chain reaction) method, and a method in which cloning is performed using homology or enzyme activity as index from a genomic library or cDNA library based on known gene information.

These genes include mutated genes, for example, by genetic pleomorphism (base sequence of genes is partially changed based on natural spontaneous mutation in genes).

As such a method, to be more specific, for example, from the chromosome DNA of *Escherichia coli* K12, using PCR method, cadA gene or ldc gene, i.e., gene for coding lysine decarboxylase, is cloned. The chromosome DNA is not limited as long as it is derived from *Escherichia coli*, and those derived from an arbitrary strain can be used.

The localization of lysine decarboxylase on the surface of the thus obtained surface expression cell can be confirmed, for example, by immune reactions of the surface expression cell with antibody made from lysine decarboxylase as antigen, and then the surface expression cell is embedded and sliced, and observed with an electron microscope (immunoelectron microscopy).

The surface expression cell is sufficient when lysine decarboxylase is localized on the cell surface, and for example, lysine decarboxylase can be localized on the cell surface, and at the same time can be expressed intracellularly.

Examples of lysine decarboxylase also include those prepared from recombinant cells with elevated activities intracellularly and/or at cell surface of lysine decarboxylase.

The lysine decarboxylase activity can be improved intracellularly and/or at cell surface by, without limitation, for example, a method of increasing an enzyme amount of lysine decarboxylase, and a method that elevates lysine decarboxylase activity intracellularly and/or at cell surface.

The enzyme amount in the cells or the cell surface is increased, for example, by improving the transcriptional regulatory region in genes, increasing the copy number of genes, or efficient translation to protein.

In the improvement in transcriptional regulatory region, modification is added to increase the gene transcription amount, for example, by introducing a mutation in a promoter, the promoter is reinforced, thereby increasing the gene transcription amount in downstream. Other than introducing a mutation in the promoter, a highly expressing promoter in the host can be introduced. Examples of promoters include, to be more specific, in *Escherichia coli*, lac, tac, and trp. Also, an enhancer can be newly introduced to increase the transcription amount of the genes. Introduction of genes such as chromosomal DNA promoter can be performed in conformity with, for example, Japanese Unexamined Patent Publication No. H1-215280.

Increase in the copy number of genes can be achieved, to be specific, by forming recombinant DNAs by connecting genes to a multi-copy vector, and allowing the host cell to hold the recombinant DNA. Vectors include those widely used, including plasmid, phage, etc. and also include, other than those, for example, transposon (Berg, D. E and Berg. C. M. Bio/Technol., vol. 1, P. 417 (1983)) and Muphage (Japanese Unexamined Patent Publication No. H2-109985). Furthermore, the copy number can be increased by introducing genes into chromosomes with a method using a plasmid for homologous recombination.

As a method for increasing protein translation efficiency, examples include, introducing and modifying, in procaryotes, SD sequence (Shine, J. and Dalgarno, L., Proc. Natl. Acad. Sci. USA, 71, 1342-1346 (1974)), in eucaryotes. Kozak consensus sequence (Kozak, M., Nuc. Acids Res. Vol. 15, p. 8125-8148 (1987)), and also optimizing codon to be used (Japanese Unexamined Patent Publication No. S 59-125895). As a method of increasing lysine decarboxylase activity in cells and/or at cell surface, the lysine decarboxylase activity itself can be increased by introducing a mutation in the structural gene itself of lysine decarboxylase.

As a method of causing a mutation in genes, example include site-specific mutagenesis (Kramer, W. and frita, H. J., Methods in Enzymology, vol. 154, P. 350 (1987)), recombinant PCR (PCR Technology, Stockton Press (1989), a method in which a specific portion of DNA is chemically synthesized, a method in which genes are treated with hydroxyamine, a method in which strain having genes are irradiated with ultraviolet ray, and a method in which strain having genes are treated with chemicals such as nitrosoguanidine or nitrous acid.

The method of culturing such a recombinant cell (internal expression cell, surface expression cell, etc.) is not particularly limited, and a known method can be used. To be more specific, for example, when culturing microorganism, as a medium, for example, a medium containing a carbon source, a nitrogen source, and inorganic ions is used.

Examples of carbon sources include saccharides such as glucose, lactose, galactose, fructose, arabinose, maltose, xylose, trehalose, ribose, and hydrolysate of starch; alcohols such as glycerol, mannitol, and sorbitol; and organic acids such as gluconic acid, fumaric acid, citric acid, and succinic acid.

These carbon sources may be used singly or in a combination of two or more.

Examples of nitrogen sources include inorganic ammonium salts such as ammonium sulfate, ammonium chloride, and ammonium phosphate; organic nitrogen such as soybean hydrolysate; ammonia gas; and ammonia water.

These nitrogen sources may be used singly or in a combination of two or more.

Examples of inorganic ions include sodium ions, magnesium ions, potassium ions, calcium ions, chloride ions, manganese ions, iron ions, phosphoric acid ions, and sulfuric acid ions.

These inorganic ions may be used singly or in a combination of two or more.

To the medium, as necessary, other organic components (organic micronutrients) may be added, and examples of such organic components include various amino acids; vitamins such as vitamin $B_1$; required substances of nucleic acids such as RNA; and yeast extracts.

Examples of such a medium include, to be more specific, LB medium.

The cultivation conditions are not particularly limited, and examples thereof include, when cultivating *Escherichia coli* under aerobic conditions, the following: a cultivation temperature of, for example, 30 to 45° C., preferably 30 to 40° C.; a cultivation pH of, for example, 5 to 8, preferably 6.5 to 7.5; and cultivation time of, for example, 16 to 72 hours, preferably 24 to 48 hours. For adjustment of pH, for example, inorganic or organic acidic or alkaline substances, and ammonia gas may be used.

Then, recombinant cells (internal expression cell, surface expression cell) proliferated in such a medium is collected, for example, by centrifugal separation.

Furthermore, in this method, the recovered cell can be used, for example, as resting cell, or as necessary, can be disrupted, and used as a solution of those disrupted cells (bacterial cell-disrupted solution).

For preparation of the cell disrupted solution (bacterial cell-disrupted solution), a known method can be used. To be more specific, for example, first, the obtained internal expression cell and/or surface expression cell are disrupted, for example, by ultrasonic treatment, using Dyno Mill, French Press, etc. and thereafter, cell residues are removed by centrifugal separation.

In this method, as necessary, lysine decarboxylase can be purified from the obtained cell disrupted solution.

The purification method of lysine decarboxylase is not particularly limited, and a known method (e.g., ammonium sulphate fractionation, ion exchange chromatography, hydrophobic chromatography, affinity chromatography, gel filtration chromatography, isoelectric point precipitation, heat treatment, pH treatment, etc.) generally used for enzyme purification can be used in suitable combination, as necessary.

In lysine (or its salt) decarboxylation, the thus obtained resting cell and/or its cell disrupted solution, and an aqueous solution of lysine (or its salt) are blended, and lysine decarboxylase is allowed to act on lysine (or its salt) in water.

The ratio (based on the mass of the dry bacterial cell) of the bacterial cell (cell) used in the reaction relative to a total mass of the lysine (or its salt) used in the reaction is not particularly limited, as long as it is sufficient to convert lysine (or its salt) to pentamethylenediamine (or its salt), and for example, 0.01 or less, preferably 0.007 or less.

The total mass of lysine (or its salt) used in the reaction is the total of the mass of lysine (or its salt) present in the reaction system at the start of the reaction (when lysine (or its salt) is added to the reaction system during the reaction, their total).

The dry bacterial cell-based mass of the bacterial cell is the mass of bacterial cells that are dry and do not contain moisture.

The dry bacterial cell-based mass of bacterial cells can be obtained, for example, by separating bacterial cells from a liquid containing bacterial cells (bacterial cell liquid) by a method such as centrifugal separation or filtration, drying the bacterial cells until the mass is a constant mass, and measuring the mass.

The reaction temperature in the lysine (or its salt) decarboxylation is, for example, 28 to 55° C., preferably 35 to 45° C. and the reaction time is, although it is different depending on the type of lysine decarboxylase used, for example, 1 to 72 hours, preferably 12 to 36 hours. The reaction pH is, for example, 5.0 to 8.0, preferably, 5.5 to 6.5.

Thus, lysine (or its salt) is subjected to decarboxylation, and converted to pentamethylenediamine. And as a result, an aqueous solution (aqueous solution of pentamethylenediamine) containing pentamethylenediamine or its salt is obtained.

Examples of the pentamethylenediamine obtained by a biochemical method include 1,5-pentamethylenediamine, 1,4-pentamethylenediamine, 1,3-pentamethylenediamine, and a mixture thereof. To be specific, when the above-described lysine decarboxylation is used, generally, 1,5-pentamethylenediamine is obtained.

Examples of the salt of pentamethylenediamine include those corresponding to the above-described lysine salts, to be specific, organic salts of pentamethylenediamine including carboxylate (e.g., formate, acetate, adipate, oxalate, 2-ethylhexanoate, stearate, sebacate, succinate, etc.), and sulfonate; and inorganic salt of pentamethylenediamine including nitrate, sulfate, hydrochloride, phosphate, carbonate, and hydrogencarbonate.

To be specific, for example, when lysine•monohydrochloride is used, hydrochloride of pentamethylenediamine, for example, dihydrochloride, monohydrochloride monocarbonate, or monohydrochloride monohydrogencarbonate is obtained.

The reaction yield of pentamethylenediamine or its salt is, based on lysine (or its salt), for example, 10 to 100 mol %, preferably 70 to 100 mol %, more preferably 80 to 100 mol %.

The pentamethylenediamine concentration or its salt concentration (in the case of pentamethylenediamine salt, pentamethylenediamine-based concentration) of the aqueous solution of pentamethylenediamine is, for example, 1 to 70 mass %, preferably 2 to 50 mass %, more preferably 5 to 40 mass %.

In this reaction, the obtained pentamethylenediamine is alkaline, and therefore the pH of the reaction liquid may increase as lysine (or its salt) is converted to pentamethylenediamine (or its salt). In such a case, as necessary, an acidic substance (e.g., organic acid, and inorganic acid such as hydrochloric acid) can be added to adjust the pH.

The aqueous solution of pentamethylenediamine has a pH of, for example, 8 or less, preferably 7 or less, and generally 1 or more.

In this reaction, as necessary, for example, vitamin $B_6$ and/or derivatives thereof can be added to the reaction liquid.

Examples of vitamin $B_6$ and/or its derivatives include pyridoxine, pyridoxamine, pyridoxal, and pyridoxal phosphate.

These examples of vitamin $B_6$ and/or its derivatives may be used singly or in a combination of two or more.

As the vitamin $B_6$ and/or its derivatives, preferably, pyridoxal phosphate is used.

By adding vitamin $B_6$ and/or its derivatives, production rate and reaction yield of pentamethylenediamine can be improved.

In this method, as necessary, a known post treatment such as sterilization, adsorption, and filtering, and moreover, pH adjustment (e.g., when an acidic substance is added as described above, an alkaline substance is added, etc.) can also be performed.

In this method, from the obtained aqueous solution of pentamethylenediamine, as necessary, a portion of water can be distilled off.

To be more specific, for example, the aqueous solution of pentamethylenediamine is heated using a distillation apparatus etc. equipped with a continuous multiple distillation column, a batch multiple distillation column, etc. under 0.1 kPa to normal pressure, thereby performing distillation. The aqueous solution of pentamethylenediamine in which water is partially distilled off can be obtained in this manner.

In this method, preferably, from the obtained aqueous solution of pentamethylenediamine as described above, pentamethylenediamine or its salt is extracted. In the extraction, for example, liquid-liquid extraction method is used.

In the liquid-liquid extraction method, for example, the following methods are used: (1) a method in which by bringing an extractant (described later) into contact with the aqueous solution of pentamethylenediamine batchwise, semi-continuously, or continuously, and mixing and stirring them, pentamethylenediamine or its salt is extracted (partitioned) to the extractant (described later), and pentamethylenediamine or its salt is separated from the extractant (described later); (2) a method in which an aqueous solution of pentamethylenediamine and an extractant (described later) are supplied countercurrently and continuously to a column (spray column, staged extraction column) equipped with a porous plate, or a column (countercurrent differential extraction column, non-mixing staged extraction column: 5th edition, revised, Chemical Engineers Handbook, p 566 to 569, edited by Society of Chemical Engineers. Maruzen (1988)) equipped with filling, a nozzle, an orifice plate, a baffle, an injector and/or a static mixer, pentamethylenediamine or its salt is extracted (partitioned) to the extractant (described later), and thereafter, the extractant (described later) is allowed to flow out continuously, and pentamethylenediamine or its salt is separated from the extractant (described later), (3) a method in which an aqueous solution of pentamethylenediamine and an extractant (described later) are supplied countercurrently and continuously to a column (stirring staged extraction column: 5th edition, revised, Chemical Engineers Handbook, p 569 to 574, edited by Society of Chemical Engineers, Maruzen (1988)) equipped with a baffle plate and a stirring blade, pentamethylenediamine or its salt is extracted (partitioned) to the extractant (described later), thereafter, the extractant (described later) is allowed to flow out continuously, and pentamethylenediamine or its salt is separated from the extractant (described later); and (4) an extractant (described later) is brought into contact with an aqueous solution of pentamethylenediamine using a mixer settler extractor, or a centrifugal extraction apparatus (5th edition, revised, Chemical Engineers Handbook, p 563 to 566, and p 574, edited by Society of Chemical Engineers. Maruzen (1988)), pentamethylenediamine or its salt is extracted (partitioned) to the extractant (described later), and pentamethylenediamine or its salt is separated from the extractant (described later).

These liquid-liquid extraction methods may be used singly or in a combination of two or more.

As the liquid-liquid extraction method, in view of production efficiency, preferably, a method in which pentamethylenediamine or its salt is extracted (partitioned) to the extractant (described later) continuously, to be more specific, for example, the above-described methods of (1) to (3) are used.

The mixing ratio of the aqueous solution of pentamethylenediamine to the extractant (described later) in the liquid-liquid extraction is, relative to 100 parts by mass of the aqueous solution of pentamethylenediamine (when the extraction is continuous, supplied amount per unit time. The same is applied below as well.), for example, 30 to 300 parts by mass of the extractant (described later), and in view of economy and productivity, preferably 50 to 200 parts by mass, more preferably 50 to 150 parts by mass, particularly preferably 80 to 120 parts by mass.

In the liquid-liquid extraction, the aqueous solution of pentamethylenediamine and the extractant (described later) are mixed, for example, using stirring blade. etc. under normal pressure (atmospheric pressure), at, for example, 5 to 60° C., preferably 10 to 60° C. more preferably 15 to 50° C. even more preferably 15 to 40° C., for, for example, 1 to 120 minutes, preferably 5 to 90 minutes, more preferably 5 to 60 minutes.

Examples of stirring blades include, without limitation, for example, propeller, flat blade, flat blade with angles, flat blade with pitch, flat blade disk turbine, blade with tilt disk turbine, bent blade, Pfaudler type stirring blades, blue margin type, dissolver, and anchor.

The number of revolution in the mixing is, for example, 5 to 3000 rpm, preferably 10 to 2000 rpm, more preferably 20 to 1000 rpm.

In this manner, pentamethylenediamine or its salt is extracted into the extractant (described later).

Next, in this method, the mixture of pentamethylenediamine or its salt and the extractant (described later) is allowed to stand for, for example, 5 to 300 minutes, preferably 10 to 240 minutes, more preferably 20 to 180 minutes, and thereafter, the extractant (pentamethylenediamine extract, that is, a mixture of the extractant (described later) and the pentamethylenediamine or its salt) in which pentamethylenediamine or its salt is extracted is taken out by a known method.

When the pentamethylenediamine or its salt cannot be sufficiently extracted by one liquid-liquid extraction, the liquid-liquid extraction can be conducted repeatedly a plurality of times (e.g., 2 to 5 times).

In this manner, the pentamethylenediamine or its salt in the aqueous solution of pentamethylenediamine can be extracted into the extractant (described later).

In the thus obtained extractant (mixture of the extractant (described later) and pentamethylenediamine or its salt), the pentamethylenediamine or its salt concentration is, for example, 0.2 to 40 mass %, preferably 0.3 to 35 mass %, more preferably 0.4 to 30 mass %, particularly preferably 0.8 to 25 mass %.

The yield (extraction rate) of pentamethylenediamine or its salt after the extraction is, based on lysine (or its salt), for example, 65 to 100 mol %, preferably 70 to 100 mol %, more preferably 80 to 100 mol %, particularly preferably 90 to 100 mol %.

In this method, as necessary, for example, pentamethylenediamine or its salt can also be isolated from the mixture of the obtained extractant (described later) and pentamethylenediamine or its salt. The isolation of pentamethylenediamine or its salt is not particularly limited, and for example, the isolation of pentamethylenediamine (or its salt) can be performed by distilling the mixture of the extractant (described later) and pentamethylenediamine or its salt, using a distillation apparatus including a continuous multistage distillation column, a batch multistage distillation column, etc. at, for example, 50 to 182° C., under 0.1 kPa to normal pressure, removing the extractant (described later).

In such an extraction, examples of extractants include non-halogen organic solvents.

The non-halogen organic solvent is an organic solvent that does not contain halogen atoms (fluorine, chlorine, bromine, iodine, etc.) in the molecule, for example, a non-halogen aliphatic organic solvent, a non-halogen alicyclic organic solvent, and a non-halogen aromatic organic solvent.

Examples of non-halogen aliphatic organic solvents include straight chain non-halogen aliphatic organic solvents, and branched non-halogen aliphatic organic solvents.

Examples of straight chain non-halogen aliphatic organic solvents include straight chain non-halogen aliphatic hydrocarbons, straight chain non-halogen aliphatic ethers, and straight chain non-halogen aliphatic alcohols.

Examples of straight chain non-halogen aliphatic hydrocarbons include n-hexane, n-heptane, n-nonane, n-decane, and n-dodecane.

Examples of straight chain non-halogen aliphatic ethers include diethylether, dibutylether, and dihexylether.

Examples of straight chain non-halogen aliphatic alcohols include straight chain monohydric alcohols having 1 to 3 carbon atoms (e.g., methanol, ethanol, n-propanol, isopropanol, etc.), straight chain monohydric alcohols having 4 to 7 carbon atoms (e.g., n-butanol, n-pentanol, n-hexanol, n-heptanol, etc.), and straight chain monohydric alcohols having 8 or more carbon atoms (e.g., n-octanol, n-nonanol, n-decanol, n-undecanol, n-dodecanol, etc.).

Examples of branched non-halogen aliphatic organic solvents include branched non-halogen aliphatic hydrocarbons, branched non-halogen aliphatic ethers, branched non-halogen aliphatic monohydric alcohols, and branched non-halogen aliphatic polyhydric alcohols.

Examples of branched non-halogen aliphatic hydrocarbons include 2-methylpentane, 2,2-dimethylbutane, 2,3-dimethylbutane, 2-methylhexane, 3-methylhexane, 2,3-dimethylpentane, 2,4-dimethylpentane, n-octane, heptane, 3-methylheptane, 4-methylheptane, 3-ethylhexane, 2,2-dimethylhexane, 2,3-dimethylhexane 2,4-dimethylhexane, 2,5-dimethylhexane, 3,3-dimethylhexane, 3,4-dimethylhexane, 2-methyl-3-ethylpentane, 3-methyl-3-ethylpentane, 2,3,3-trimethylpentane, 2,3,4-trimethylpentane, 2,2,3,3-tetramethylbutane, and 2,2,5-trimethylhexane.

Examples of branched non-halogen aliphatic ethers include diisopropylether and diisobutylether.

Examples of branched non-halogen aliphatic monohydric alcohols include branched monohydric alcohol having 4 to 7 carbon atoms (e.g., 2-butanol, isobutanol, tert-butanol, 2-pentanol, 3-pentanol, isopentanol, 2-methyl-1-butanol, 2-methyl-3-butanol, 2,2-dimethyl-1-propanol, tert-pentanol, 2-hexanol, 3-hexanol, isohexanol, 2-methyl-2-pentanol, 2-methyl-1-pentanol, 3-methyl-1-pentanol, 2-ethyl-1-butanol, 3,3-dimethyl-1-butanol, 2-heptanol, 3-heptanol, 4-heptanol, 5-methyl-1-hexanol, 4-methyl-1-hexanol, 3-methyl-1-hexanol, 2-ethyl-2-methyl-1-butanol, etc.); and branched monohydric alcohols having 8 or more carbon atoms (e.g., isooctanol, isononanol, isodecanol, 5-ethyl-2-nonanol, trimethylnonylalcohol, 2-hexyldecanol, 3,9-diethyl-6-tridecanol, 2-isoheptylisoundecanol, 2-octyldodecanol, etc.).

Examples of branched non-halogen aliphatic polyhydric alcohols include 2-ethyl-1,3-hexanediol.

These non-halogen aliphatic organic solvents may be used singly or in a combination of two or more.

As the non-halogen aliphatic organic solvent, preferably, straight chain non-halogen aliphatic organic solvents, more preferably, straight chain non-halogen aliphatic alcohols are used.

When straight chain non-halogen aliphatic alcohols are used, pentamethylenediamine can be extracted in high yield.

As the non-halogen aliphatic organic solvent, preferably, monohydric alcohols having 4 to 7 carbon atoms (straight chain monohydric alcohol having 4 to 7 carbon atoms, branched monohydric alcohol having 4 to 7 carbon atoms).

When monohydric alcohol having 4 to 7 carbon atoms is used, pentamethylenediamine or its salt can be extracted efficiently, and furthermore, impurity (Nitrogen-containing six-membered ring compound having a C=N bond (described later), etc.) content proportion of pentamethylenediamine or its salt can be decreased.

Examples of non-halogen alicyclic organic solvents include non-halogen alicyclic hydrocarbons (e.g., cyclopentane, methylcyclopentane, cyclohexane, methylcyclohexane, ethylcyclohexane, p-menthane, bicyclohexyl, etc.).

These non-halogen alicyclic organic solvents may be used singly or in a combination of two or more.

Examples of non-halogen aromatic organic solvents include non-halogen aromatic hydrocarbons (e.g., benzene, toluene, xylene, ethylbenzene, isopropylbenzene, 1,3,5-trimethylbenzene, 1,2,3,4-tetrahydronaphthalene, n-butylbenzene, sec-butylbenzene, tert-butylbenzene, ethylbenzene, etc.), and phenols (e.g., phenol, cresol, etc.).

These non-halogen aromatic organic solvents may be used singly or in a combination of two or more.

Examples of non-halogen organic solvents also include a mixture of aliphatic hydrocarbons and aromatic hydrocarbons, and examples of such a mixture include petroleum ether, and petroleum benzine.

These non-halogen organic solvents may be used singly or in a combination of two or more.

As the extractant, in the range that does not inhibit excellent effects of the present invention, for example, halogen organic solvents (organic solvents containing halogen atoms in its molecule) can be used.

Examples of halogen organic solvents include halogen aliphatic hydrocarbons (e.g., chloroform, dichloromethane, carbon tetrachloride, tetrachloroethylene, etc.), and halogen aromatic hydrocarbons (e.g., chlorobenzene, dichlorobenzene, chlorotoluene, etc.).

These halogen organic solvents may be used singly or in a combination of two or more.

On the other hand, if the halogen organic solvent is used as the extractant, the nitrogen-containing six-membered ring compound having a C=N bond (described later) may increase relative to a total amount of the obtained pentamethylenediamine or its salt.

In such a case, although it is to be described later, when pentamethylene diisocyanate (described later) is produced by using the pentamethylenediamine or its salt, and then the pentamethylene diisocyanate (described later) is allowed to react to produce an isocyanate modified substance (described later), or a polyurethane resin (described later), productivity and physical property (e.g., yellowing resistance, etc.) of the isocyanate modified substance (described later) may be poor.

Also in the case when a polyurethane resin is produced by allowing such pentamethylene diisocyanate (described later) or an isocyanate modified substance (described later) to react with an active hydrogen compound (described later), physical property (e.g., mechanical strength, chemical resistance, etc.) of the obtained polyurethane resin may be poor.

Therefore, as the extractant, preferably, a non-halogen organic solvent, more preferably, a non-halogen aliphatic organic solvent is used.

When pentamethylenediamine or its salt is extracted by using a non-halogen aliphatic organic solvent, the nitrogen-containing six-membered ring compound having a C=N bond (described later) content in the pentamethylenediamine or its salt can be reduced.

Therefore, when pentamethylene diisocyanate is produced by using such pentamethylenediamine or its salt, pentamethylene diisocyanate that allows efficient production of an isocyanate modified substance having excellent characteristics, or a polyurethane resin having excellent characteristics can be produced.

In the present invention, the boiling point of the extractant is, for example, 60 to 250° C., preferably 80 to 200° C., more preferably 90 to 150° C.

When the boiling point of the extractant is below the above-described lower limit, when obtaining pentamethylenediamine or its salt by extraction from the aqueous solution of pentamethylenediamine, separation from the extractant may become difficult.

On the other hand, when the boiling point of the extractant is more than the above-described upper limit, when obtaining pentamethylenediamine or its salt from a mixture of the extractant and pentamethylenediamine or its salt, consuming energy at the separation process may increase.

The method of obtaining pentamethylenediamine or its salt from the aqueous solution of pentamethylenediamine is not limited to the above-described extraction, and for example, a known isolation and purification method such as distillation can also be used.

The thus obtained pentamethylenediamine or its salt does not contain a nitrogen-containing six-membered ring compound having a C=N bond (hereinafter may be referred to as a C=N six-membered ring compound), or the amount of the C=N six-membered ring compound is reduced.

Examples of the C=N six-membered ring compound include a nitrogen-containing six-membered ring compound having an amino group and a C=N bond (hereinafter may be referred to as an amino group-containing C=N six-membered ring compound), and a nitrogen-containing six-membered ring compound having a C=N bond but no amino group (hereinafter may be referred to as amino group-noncontaining C=N six-membered ring compound).

The amino group-containing C=N six-membered ring compound is, for example, a compound represented by the general formula (3) below:

[Chemical Formula 3]

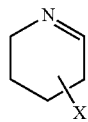

(3)

(where X represents an aminomethyl group)

Examples of the compound represented by general formula (3) above include, to be more specific, for example, 2-(aminomethyl)-3,4,5,6-tetrahydropyridine.

Examples of the amino group-noncontaining C=N six-membered ring compound include 2,3,4,5-tetrahydropyridine.

In the present invention, the amount of those C=N six-membered ring compounds contained (total amount of the amino group-containing C=N six-membered ring compound and the amino group-noncontaining C=N six-membered ring compound) relative to a total amount of pentamethylenediamine or its salt (total amount of pentamethylenediamine or its salt and impurities (including amino group-containing C=N six-membered ring compound and amino group-noncontaining C=N six-membered ring compound)) is, for example, 2 mass % or less, preferably, 1.5 mass % or less, more preferably, 1 mass % or less, particularly preferably 0.5 mass % or less, most preferably 0.3 mass % or less.

When the C=N six-membered ring compound content is more than the above-described upper limit, and when the pentamethylenediamine is used as a resin material, characteristics of the resin to be obtained may be reduced.

To be more specific, in the case when pentamethylenediamine or its salt having the C=N six-membered ring compound content of more than the above-described upper limit is used to produce pentamethylene diisocyanate (described later), and then the pentamethylene diisocyanate (described later) is allowed to react to produce isocyanate modified substance (described later), productivity may be poor, for example, insufficient reaction velocity of the pentamethylene diisocyanate (described later) and requires a large amount of catalyst, and furthermore, physical properties (e.g., storage stability, etc.) of the obtained isocyanate modified substance (described later) may not be ensured sufficiently.

In contrast, when the C=N six-membered ring compound content is the above-described upper limit or less, the pentamethylenediamine is used as a resin material, and a resin with excellent characteristics can be obtained.

To be more specific, for example, when the C=N six-membered ring compound content is the above-described upper limit or less, pentamethylene diisocyanate that allows efficient production of isocyanate modified substance (described later) having excellent characteristics can be produced.

The amino group-containing C=N six-membered ring compound content relative to a total amount of the pentamethylenediamine or its salt is, for example, 1.5 mass % or less, preferably 1.1 mass % or less, more preferably, 0.7 mass % or less, particularly preferably 0.3 mass % or less, and most preferably 0.2 mass % or less.

When the amino group-containing C=N six-membered ring compound content is more than the above-described upper limit as well, when the pentamethylenediamine is used as the resin material, characteristics of the resin to be obtained may be reduced.

To be more specific, in the same manner as described above, when pentamethylene diisocyanate (described later) is produced by using pentamethylenediamine or its salt having an amino group-containing C=N six-membered ring compound content of more than the above-described upper limit, and then the pentamethylene diisocyanate (described later) is allowed to react to produce isocyanate modified substance (described later), productivity may be poor, for example, the reaction velocity of the pentamethylene diisocyanate (described later) insufficient, and a large amount of catalyst is necessary, and also, physical property (e.g., storage stability, etc.) of the obtained isocyanate modified substance (described later) may not be ensured sufficiently.

In contrast, when the amino group-containing C=N six-membered ring compound content is the above-described upper limit or less, a resin with excellent characteristics can be obtained using the pentamethylenediamine as the resin material.

To be more specific, for example, when the amino group-containing C=N six-membered ring compound content is the above-described upper limit or less, pentamethylene diisocyanate that allows efficient production of an isocyanate modified substance having excellent characteristics can be produced.

The amino group-noncontaining C=N six-membered ring compound content relative to a total amount of pentamethylenediamine or its salt is, for example, 0.5 mass % or less, preferably 0.4 mass % or less, more preferably 0.3 mass % or less, more preferably 0.2 mass % or less, and most preferably 0.1 mass % or less.

When the amino group-noncontaining C=N six-membered ring compound content is more than the above-described upper limit, although not to be described in detail, when the pentamethylenediamine is used as the resin material, characteristics of the resin to be obtained may be reduced.

To be more specific, physical properties (e.g., mechanical strength, chemical resistance, etc.) of a polyurethane resin may not be ensured sufficiently, when pentamethylenediamine or its salt having an amino group-noncontaining C=N six-membered ring compound content of more than the above-described upper limit is used to produce the pentamethylene diisocyanate (described later), and when the pentamethylene diisocyanate (described later) is allowed to react to produce isocyanate modified substance (described later), and the produced isocyanate modified substance is allowed to react with an active hydrogen compound to produce the polyurethane resin.

Next, in this method, the obtained pentamethylenediamine or its salt is phosgenated, thereby producing pentamethylene diisocyanate (pentamethylene diisocyanate before heat treatment to be described later. In the following, PDI before heating.).

Pentamethylenediamine or its salt can be phosgenated, to be more specific, by a method (hereinafter may be referred to as cold/hot two-stage phosgenation method) in which pentamethylenediamine is directly allowed to react with phosgene; or a method (hereinafter may be referred to as amine hydrochloride phosgenation method) in which hydrochloride of pentamethylenediamine is suspended in an inactive solvent (described later) to react with phosgene.

In the cold/hot two-stage phosgenation method, for example, first, an inactive solvent is introduced to a reactor capable of stirring and provided with a phosgene inlet tube, and then the pressure in the reaction system is set to, for example, normal pressure to 1.0 MPa, preferably normal pressure to 0.5 MPa, and the temperature is set to, for example, 0 to 80° C. preferably 0 to 60° C.

Examples of inactive solvents include aromatic hydrocarbons such as benzene, toluene, xylene, ethylbenzene, etc.; aliphatic acid esters such as ethyl acetate, butyl acetate, amyl acetate, etc.; aromatic acid esters such as methyl salicylate, dimethyl phthalate, dibutyl phthalate, methyl benzoate, etc.; chlorinated aromatic hydrocarbons such as monodichlorobenzene, orthodichlorobenzene, trichlorobenzene, etc.; and chlorinated hydrocarbons such as chloroform, carbon tetrachloride, etc.

These inactive solvents may be used singly or in a combination of two or more.

The blending amount (total amount) of the inactive solvent relative to 100 parts by mass of pentamethylenediamine as a material is, for example, 400 to 3000 parts by mass, preferably 500 to 2000 parts by mass.

Next, in this method, phosgene is introduced, for example, so that the amount of phosgene is 1 to 10 times mol, preferably 1 to 6 times mol relative to one amino group in pentamethylenediamine; and pentamethylenediamine dissolved in the above-described inactive solvent is added. During this time, the reaction liquid is held at, for example, 0 to 80° C., preferably 0 to 60° C., and at the same time, generated hydrogen chloride is released outside of the reaction system via the reflux condenser (cold phosgenation reaction). The contents of the reactor are thus formed into a slurry.

In the cold phosgenation reaction, pentamethylenedicarbamoyl chloride and amine hydrochloride of pentamethylenediamine are produced.

Next, in this method, the pressure in the reaction system is set to, for example, normal pressure to 1.0 MPa, preferably 0.05 to 0.5 MPa, and the temperature is increased for, for example, 30 min to 5 hours, to a temperature range of, for example, 80 to 180° C. After the temperature increase, for example, the reaction is allowed to continue for 30 min to 8 hours, thereby dissolving the slurry liquid completely (hot phosgenation reaction).

In the hot phosgenation reaction, at the time of temperature increase and the high temperature reaction, the dissolved phosgene is evaporated and escapes outside the reaction system via the reflux condenser, and therefore phosgene is introduced appropriately until the reflux amount from the reflux condenser can be confirmed.

After the termination of the hot phosgenation reaction, an inactive gas such as nitrogen gas is introduced into the reaction system at, for example, 80 to 180° C., preferably 90 to 160° C. thereby purging dissolved excessive phosgene and hydrogen chloride.

In the hot phosgenation reaction, pentamethylenedicarbamoyl chloride produced in the cold phosgenation reaction is thermally decomposed, pentamethylene diisocyanate (PDI before heating) is produced, and furthermore, amine hydrochloride of pentamethylenediamine is phosgenated, thereby producing pentamethylene diisocyanate (PDI before heating).

On the other hand, in the amine hydrochloride phosgenation method, the hydrochloride of pentamethylenediamine is dried sufficiently and finely pulverized, and thereafter, in the same reactor as the reactor of the above-described cold/hot two-stage phosgenation method, hydrochloride of pentamethylenediamine is stirred in the above-described inactive solvent, thereby dispersing the hydrochloride of pentamethylenediamine to form a slurry.

Next, in this method, the reaction temperature is maintained at for example, 80 to 180° C., preferably 90 to 160° C., and the reaction pressure is maintained at, for example, normal pressure to 1.0 MPa, preferably 0.05 to 0.5 MPa, and phosgene is introduced for 1 to 10 hours so that the total phosgene amount is 1 to 10 times the stoichiometric amount.

Pentamethylene diisocyanate (PDI before heating) is synthesized in this manner.

The reaction progress can be assumed based on the amount of the hydrogen chloride gas generated, and when the undissolved slurry in the above-described inactive solvent disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the inactive solvent is distilled off under reduced pressure.

For the method for producing pentamethylene diisocyanate (PDI before heating), in addition to the above-described method in which pentaethylenediamine or its salt is extracted from the aqueous solution thereof and introducing phosgene to the obtained extract, the following method can be used. For example, an organic solvent is added to aqueous solution of pentamethylenediamine and dehydrating the mixture to obtain a slurry of pentamethylenediamine or its salt, and phosgene is introduced into the slurry.

In this method, the organic solvent is not particularly limited, and for example, a water-insoluble organic solvent is used.

The water-insoluble organic solvent is a solvent that is substantially insoluble to water (to be specific, soluble mass of 2 g or less at 20° C. in 1 L of water), and those do not react with the components (pentamethylenediamine and its salt, pentamethylene diisocyanate, phosgene, hydrochloric acid, etc.) in the reaction can be used without specific limitation.

Examples of the water-insoluble organic solvent include, to be specific, hydrocarbons such as benzene, toluene, xylene mixture, o-xylene, m-xylene, p-xylene, cumene, 2,2,5-trimethylhexane, decane, and ethylcyclohexane; halogenated hydrocarbons such as chlorobenzene, o-dichlorobenzene, m-dichlorobenzene, p-dichlorobenzene, and o-dibromobenzene; nitrogen-containing compounds such as nitrobenzene, N,N-dimethylformamide, N,N-dimethylacetamide, and N,N'-dimethylimidazolidinone; ethers such as dibutylether, ethylene glycol dimethylether, ethylene glycol diethylether, diethylene glycol dimethylether, diethylene glycol diethylether, anisole, phenetole, methoxytoluene, benzylether, and diphenyl ether; ketones such as heptanone and diisobutylketone; and esters such as amyl formate, n-amyl acetate, isoamyl acetate, methylisoamyl acetate, n-butyl acetate, isobutyl acetate, 2-ethylbutyl acetate, methoxybutyl acetate, ethoxyethyl acetate, methoxyethyl acetate, methoxypropyl acetate, ethyl acetate, hexyl acetate, 2-ethylhexyl acetate, cyclohexyl acetate, methyl cyclohexaneacetate, benzyl acetate, phenyl acetate, methylcarbitol acetate, ethylene glycol diacetate, ethyl propionate, n-butyl propionate, isoamyl propionate, ethyl butyrate, butyl butyrate, isoamyl butyrate, butyl stearate, butyl lactate, amyl lactate, dimethyl phthalate, methyl benzoate, and ethyl benzoate.

These water-insoluble organic solvents may be used singly or in a combination of two or more.

As the water-insoluble organic solvent, preferably, halogenated hydrocarbons, more preferably chlorobenzene, o-dichlorobenzene, m-dichlorobenzene, or p-dichlorobenzene is used.

The water-insoluble organic solvent is added, relative to 100 parts by mass of pentamethylenediamine in the aqueous solution of pentamethylenediamine (in the case of pentamethylenediamine salt, pentamethylenediamine-based parts by mass), for example, in an amount of 150 to 5000 parts by mass, preferably 400 to 5000 parts by mass.

In dehydration, water is removed from the above-described solution mixture.

The dehydration method is not particularly limited, and for example, methods such as an adsorption method using an adsorbent, a distillation method using a distillation apparatus (flash distillation, etc.) are used. Preferably, distillation method, more preferably, an azeotropic dehydration of water and water-insoluble organic solvent is used.

When an azeotropic dehydration is used, for example, dehydration time can be shortened, and the water content of the slurry containing pentamethylenediamine or its salt (hereinafter referred to as pentamethylenediamine slurry) becomes low, and furthermore, reaction rate of phosgenation improves.

The conditions for azeotropic dehydration are as follows: a pressure of, for example, 1 to 101.3 kPa, preferably 1 to 85 kPa, more preferably 1 to 65 kPa, and a temperature (temperature of solution mixture) of, for example, 30 to 180° C., preferably 30 to 170° C., more preferably 30 to 160° C.

When the pressure and/or the temperature is within the above-described range, particle size of the pentamethylenediamine slurry may easily be reduced, the reaction time for phosgenation is shortened, and furthermore, productivity of pentamethylene diisocyanate improves.

In such a distillation method, when the solution mixture is stirred using a distillation apparatus, the peripheral velocity of the stirring blade is, for example, 0.3 to 5.2 m/s (50 to 1000 rpm), preferably 0.5 to 3.1 m/s (100 to 900 rpm), more preferably 1 to 4.2 m/s (200 to 800 rpm).

The dehydration can be conducted once, and as necessary, can be conducted a plurality of times separately.

The pentamethylenediamine slurry can be obtained in this manner.

The concentration of pentamethylenediamine or its salt in the pentamethylenediamine slurry (in the case of pentamethylenediamine salt, pentamethylenediamine-based concentration) is, for example, 2 to 40 mass %, preferably 2 to 20 mass %.

The water content of the pentamethylenediamine slurry is, for example, 2000 ppm or less, preferably 1500 ppm or less, more preferably 1000 ppm or less, and usually 5 ppm or more.

When the water content of the pentamethylenediamine slurry is the above-described upper limit or less, reaction rate of phosgenation may become high.

The average particle size of the pentamethylenediamine slurry (measurement method: laser diffraction scattering device: MICROTRAC HRA MODEL: 9320-X100 (manufactured by NIKKISO CO., LTD.)) is, for example, 10 to 1000 μm, preferably 50 to 500 μm, more preferably 50 to 300 μm, even more preferably 50 to 200 μm.

When the average particle size of the pentamethylenediamine slurry is within the above-described range, reaction velocity and reaction rate of phosgenation may become high.

Next, in this method, the pentaethylenediamine slurry is introduced into a reactor in which stirring is possible and a phosgene inlet tube is provided. Then, the reaction temperature in the reaction system is set, for example, 80 to 200° C., preferably 90 to 180° C.; the reaction pressure is maintained to a normal pressure to 1.0 MPa, preferably 0.05 to 0.5 Mpa; and phosgene is introduced taking 1 to 10 hours so that the total phosgene amount is 1 to 10 times the stoichiometric amount.

The reaction progress can be assumed based on the amount of the hydrogen chloride gas generated, and when the slurry described above disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the water-insoluble organic solvent is distilled off under reduced pressure.

Pentamethylenediisocyanate (PDI before heating) can be synthesized in this manner as well.

Pentamethylenediisocyanate can be produced, as described above, by preparing a pentamethylenediamine slurry, but preferably, pentamethylenediamine or its salt is extracted, and pentamethylene diisocyanate is produced from the extract.

In this method, preferably, the obtained pentamethylene diisocyanate (PDI before heating) is heated, for example, in the presence of an inactive gas such as nitrogen.

Usually, pentamethylene diisocyanate (PDI before heating contains hydrolyzable chlorine, and furthermore, for example, a compound represented by the general formula (1) below, and a compound represented by the general formula (2) below:

[Chemical Formula 4]

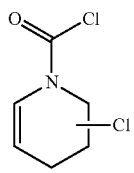

(1)

[Chemical Formula 5]

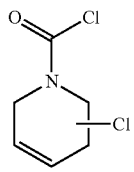

(2)

When the pentamethylene diisocyanate (PDI before heating) has a high concentration of hydrolyzable chlorine (HC), or has a high content of the compound represented by general formula (1) above, and compound represented by general formula (2) above, in modification of pentamethylene diisocyanate (described later), sufficient modification velocity cannot be ensured, and reaction has to be conducted for a long period of time in the presence of a large amount of catalyst, and therefore, costs may increase.

Moreover, a modified substance obtained by using such pentamethylene diisocyanate is, for example, poor in storage stability. To be specific, when the modified substance is exposed to a high temperature environment, side reaction is caused to reduce the isocyanate group content, and furthermore, for example, disadvantages such as a great degree of changes in color and viscosity may be caused.

Furthermore, a polyurethane resin obtained by using such pentamethylene diisocyanate or modified substance thereof may have poor physical properties that are required industrially.

In contrast, by heating and purifying pentamethylene diisocyanate by distillation, HC of pentamethylene diisocyanate (pentamethylene diisocyanate after heating. In the following, PDI after heating.), and the amounts of the compound represented by general formula (1) above and the compound represented by general formula (2) above can be decreased significantly.

The heating conditions are as follows: the heating temperature of, for example, 180° C. or more, preferably 190° C. or more, more preferably 200° C. or more, particularly preferably, 210° C. or more, most preferably, more than 220° C., and for example, 245° C. or less, preferably 240° C. or less, more preferably 235° C. or less, particularly preferably, 230° C. or less, most preferably 225° C. or less; and the heating time of for example, 0.4 to 6 hours, preferably 0.5 to 4 hours, more preferably 0.5 to 2 hours.

In the heating, to stabilize pentamethylene diisocyanate, preferably, pentamethylene diisocyanate (PDI before heating) is heated in the presence of a phosphorus-containing compound.

Examples of the phosphorus-containing compound include organic phosphorous acid esters, to be specific, for example, organic phosphorous acid diester, and organic phosphorous acid triester; to be more specific, for example, monophosphites such as triethylphosphite, tributylphosphite, tris (2-ethylhexyl) phosphite, tridecylphosphite, trilauryl phosphite, tris(tridecyl) phosphite, tristeaiyl phosphite, triphenylphosphite, tris(nonylphenyl) phosphite, tris(2,4-di-t-butylphenyl) phosphite, diphenyldecylphosphite, and diphenyl (tridecyl) phosphite; di, tri, or tetraphosphites derived from polyhydric alcohols such as distearyl•pentaerythrityl•diphosphite, di•dodecyl•pentaerythritol•diphosphite, di•tridecyl•pentaerythritol•diphosphite, dinonylphenyl•pentaerythritol•diphosphite, tetraphenyl•tetra•tridecyl•pentaerythrityl•tetraphosphite• tetraphenyl•dipropylene glycol•diphosphite, and tripentaerythritol•triphosphite; diphosphites derived from bisphenol compounds such as di•alkyl•bisphenol A•diphosphite having 1 to 20 carbons, and 4,4'-butylidenebis(3-methyl-6-t-butylphenyl-di•tridecyl) phosphite; polyphosphites such as hydrogenated bisphenol A phosphite polymers (molecular weight 2400 to 3000); and tris(2,3-dichloropropyl) phosphite.

These phosphorus-containing compounds may be used singly or in a combination of two or more.

As the phosphorus-containing compound, preferably, tris (tridecyl) phosphite is used.

The mixing ratio of the phosphorus-containing compound relative to 100 parts by mass of pentamethylene diisocyanate (PDI before heating) is, for example, 0.001 to 0.2 parts by mass, preferably 0.002 to 0.1 parts by mass, more preferably 0.005 to 500 parts by mass.

Next, in this method, preferably, the heated pentamethylene diisocyanate is purified by distillation.

The purification by distillation is not particularly limited, and for example, a known distillation apparatus equipped with a continuous multiple distillation column, and a batch multiple distillation column may be used.

The distillation conditions are as follows: a pressure of 0.1 kPa to normal pressure, preferably, 0.4 to 6.7 kPa, more preferably 0.5 to 4.0 kPa, most preferably 0.7 to 2.8 kPa; and a distillation temperature of for example, 70 to 245° C., preferably 85 to 150° C., more preferably 90 to 145° C., particularly preferably 95 to 135° C.

Pentamethylenediisocyanate (PDI after heating) can be synthesized in this manner.

The pentamethylene diisocyanate (PDI after heating) has a hydrolyzable chlorine concentration (hereinafter may be referred to as HC) of for example, 100 ppm or less, preferably 80 ppm or less, more preferably 60 ppm or less, and even more preferably, 50 ppm or less, and usually 1 ppm or more.

The hydrolyzable chlorine concentration can be measured, for example, in conformity with the hydrolyzable chlorine testing method described in Annex 3 of JIS K-1556 (2000).

When the hydrolyzable chlorine concentration is more than 100 ppm, in modification of pentamethylene diisocyanate to be described later, the modification velocity decreases, and may require a large amount of catalyst (described later). When a large amount of catalyst (described later) is used, degree of yellowing of the obtained polyisocyanate composition may become high, and the number average molecular weight may become high, which may lead to a high viscosity.

The pentamethylene diisocyanate (PDI after heating) contains a compound represented by general formula (1) above, and a compound represented by general formula (2) above in total of, 5 to 400 ppm, preferably 5 to 350 ppm, more preferably 5 to 300 ppm, particularly preferably 10 to 200 ppm.

When the pentamethylene diisocyanate (PDI after heating) contains a compound represented by general formula (1) above, and a compound represented by general formula (2)

above in total of more than 400 ppm, in modification of pentamethylene diisocyanate to be described later, the modification velocity may decrease and may require a large amount of catalyst (described later). When a large amount of catalyst (described later) is used, degree of yellowing of the obtained polyisocyanate composition (described later) may become high, and the number average molecular weight may become high, which may lead to a high viscosity.

When the pentamethylene diisocyanate (PDI after heating) contains a compound represented by general formula (1) above and a compound represented by general formula (2) above in total of more than 400 ppm, viscosity and color may be significantly changed in the step of storing a polyisocyanate composition (described later), and a step of manufacturing a polyurethane resin (described later).

In contrast, when the pentamethylene diisocyanate (PDI after heating) contains a compound represented by general formula (1) above, and a compound represented by general formula (2) above in total within the above-described range, a polyisocyanate composition having excellent storage stability can be produced, and the amount of catalyst used in the polyisocyanate composition production can be reduced, and therefore low costs can be achieved.

The total amount of the compound represented by general formula (1) above, and the compound represented by general formula (2) above contained can be obtained by, for example, analyzing pentamethylene diisocyanate by gas chromatograph.

The thus obtained pentamethylene diisocyanate generally corresponds to the above-described pentamethylenediamine used as the material component, to be more specific, 1,5-pentamethylene diisocyanate, 1,4-pentamethylene diisocyanate, 1,3-pentamethylene diisocyanate, or a mixture thereof. To be specific, for example, when 1,5-pentamethylenediamine (1,5-pentamethylenediamine obtained by lysine decarboxylation) is used, generally 1,5-pentamethylene diisocyanate is obtained.

The thus obtained pentamethylene diisocyanate has a purity of for example, 95 to 100 mass %, preferably 97 to 100 mass %, more preferably 98 to 100 mass %, particularly preferably 99 to 100 mass %, most preferably 99.5 to 100 mass %.

To pentamethylene diisocyanate, for example, a stabilizer can also be added.

Examples of stabilizers include antioxidants, acid compounds, compounds containing sulfonamide groups, and organic phosphite.

Examples of antioxidants include hindered phenolic antioxidants, and specific examples include 2,6-di(t-butyl)-4-methylphenol, 2,4,6-tri-t-butylphenol, 2,2'-methylenebis-(4-methyl-6-t-butylphenol), 2,2'-thio-bis-(4-methyl-6-t-butylphenol), 4,4'-thio-bis(3-methyl-6-t-butylphenol), 4,4'-butylidene-bis-(6-t-butyl-3-methylphenol), 4,4'-methylidene-bis-(2,6-di-t-butylphenol), 2,2'-methylene-bis[4-methyl-6-(1-methylcyclohexyl)-phenol], tetrakis-[methylene-3-(3,5-di-t-butyl-4-hydroxyphenyl)-propionyl]-methane, 1,3,5-trimethyl-2,4,6-tris-(3,5-di-t-butyl-4-hydroxyphenyl)-propionyl-methane, 1,3,5-trimethyl-2,4,6-tris-(3,5-di-t-butyl-4-hydroxybenzyl)-benzene, N,N'-hexamethylene-bis-(3,5-di-t-butyl-4-hydroxyhydrocinnamic acid amide, 1,3,5-tris-(3,5-di-t-butyl-4-hydroxybenzyl)-isocyanurate, 1,1,3-tris-(5-t-butyl-4-hydroxy-2-methylphenyl)-butane, 1,3,5-tris-(3,5-di-t-butyl-4-hydroxybenzyl)-mesitylene, ethylene glycol-bis-[3,3-bis-(3'-t-butyl-4'-hydroxyphenyl)-butyrate, 2,2'-thiodiethyl-bis-3-(3,5-di-t-butyl-4-hydroxyphenyl)-propionate, di-(3-t-butyl-4'-hydroxy-5-methylphenyl)-dicyclopentadiene, 2,2'-methylene-bis-(4-methyl-6-cyclohexylphenol), 1,6-hexanediol-bis-(3,5-di-t-butyl-4-hydroxyphenyl)-propionate, 2,4-bis-(n-octylthio)-6-(4-hydroxy-3,5-di-t-butylanilino)-1,3,5-triazine, diethyl-3,5-di-t-butyl-4-hydroxybenzylphosphonate, triethylene glycol-bis-3-(t-butyl-4-hydroxy-5-methylphenyl)-propionate, and also include, for example, IRGANOX 1010, IRGANOX 1076, IRGANOX 1098, IRGANOX 1135, IRGANOX 1726, IRGANOX 245, IRGANOX 3114, and IRGANOX 3790 (all manufactured by BASF Japan Ltd., trade name).

These antioxidants may be used singly or in a combination of two or more.

Examples of acid compounds include organic acid compounds, to be specific, phosphate, phosphite, hypophosphite, formic acid, acetic acid, propionic acid, hydroxyacetic acid, oxalic acid, lactic acid, citric acid, malic acid, sulfonic acid, sulfonate, phenol, enol, imide, and oxime.

These acid compounds may be used singly or in a combination of two or more.

Examples of compounds containing sulfonamide groups include aromatic sulfonamides, and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in a combination of two or more.

Examples of the organic phosphite include the above-described phosphorus-containing compounds.

These organic phosphites may be used singly or in a combination of two or more.

As the stabilizer, preferably, antioxidants, acid compounds, or a compound containing a sulfonamide group is used. More preferably, to pentamethylene diisocyanate, an antioxidant and an acid compound and/or a compound containing a sulfonamide group are blended so that pentamethylene diisocyanate contains these.

By adding such a stabilizer, storage stability of the pentamethylene diisocyanate, reactivity with an active hydrogen compound (described later), and reactivity when an isocyanate modified substance (described later) is produced by using pentamethylene diisocyanate; and furthermore, storage stability of the obtained isocyanate modified substance (described later) can be improved.

The mixing ratio of the stabilizer is not particularly limited, and is appropriately selected according to necessity and its application.

The mixing ratio of the antioxidant relative to 100 parts by mass of the pentamethylene diisocyanate is, to be specific, for example, 0.0005 to 0.05 parts by mass.

The mixing ratio of the acid compound and/or the compound containing a sulfonamide group (when used in combination, a total of these) relative to 100 parts by mass of pentamethylene diisocyanate is, for example, 0.0005 to 0.02 parts by mass.

With such pentamethylene diisocyanate, as described above, the amounts of the above-described compounds represented by general formula (1) and general formula (2) contained are reduced, and therefore polyisocyanate composition having excellent storage stability, and a polyurethane resin having various excellent physical properties can be produced at low costs.

In the present invention, the polyisocyanate composition is obtained, to be more specific, by modifying pentamethylene diisocyanate, and contains at least one of the functional groups of (a) to (e) below:
(a) an isocyanurate group,
(b) an allophanate group,
(c) a biuret group,
(d) a urethane group, and
(e) a urea group.

The polyisocyanate composition containing the above-described functional group of (a) (isocyanurate group) is a trimer of pentamethylene diisocyanate, and for example, can be obtained by allowing pentamethylene diisocyanate to react in the presence of a known isocyanurate-forming catalyst, thereby allowing trimerization.

The polyisocyanate composition containing the above-described functional group of (b)(allophanate group) is an allophanate-modified substance of pentamethylene diisocyanate, and for example, can be obtained by allowing pentamethylene diisocyanate and a monoalcohol to react, and then further allowing them to react in the presence of a known allophanate-forming catalyst.

The polyisocyanate composition containing the above-described functional group of (c) (biuret group) is a biuret-modified substance of pentamethylene diisocyanate, and for example, can be obtained by allowing pentamethylene diisocyanate to react with, for example, water, tertiary alcohol (e.g., t-butylalcohol, etc.), or secondary amine dimethylamine, diethylamine, etc.), and then further allowing them to react in the presence of a known biuretizing catalyst.

The polyisocyanate composition containing the above-described functional group of (b) (urethane group) is a polyol modified substance of pentamethylene diisocyanate, and can be obtained, for example, by reaction between pentamethylene diisocyanate and a polyol component (e.g., trimethylolpropane, etc. described later in detail).

The polyisocyanate composition containing the above-described functional group of (e) (urea group) is a polyamine modified substance of pentamethylene diisocyanate, and can be obtained, for example, by reaction between pentamethylene diisocyanate, and water, or a polyamine component (described later).

The polyisocyanate composition containing at least one of the functional groups of the above-described (a) to (e) is sufficient, and can contain two or more of the functional groups of the above-described (a) to (e). Such a polyisocyanate composition is produced by suitably combining the above-described reactions.

As the polyisocyanate composition, preferably, a trimer (polyisocyanate composition containing an isocyanurate group) of pentamethylene diisocyanate is used.

Trimer of pentamethylene diisocyanate further includes polyisocyanate having an iminooxadiazinedione group other than the isocyanurate group.

Pentamethylenediisocyanate is trimerized, for example, by a method in which pentamethylene diisocyanate is allowed to react with alcohols, and then subjected to trimerization reaction in the presence of a trimerization catalyst, and then unreacted pentamethylene diisocyanate is removed; or by a method in which after only pentamethylene diisocyanate is subjected to trimerization reaction, unreacted pentamethylene diisocyanate is removed, and the obtained trimer and alcohols are allowed to react.

Preferably, a polyisocyanate composition (trimer modified substance) is obtained by a method in which pentamethylene diisocyanate and alcohol are allowed to react, and then after being subjected to trimerization reaction in the presence of a trimerization catalyst, unreacted pentamethylene diisocyanate is removed.

In the present invention, examples of alcohols include monohydric alcohol, dihydric alcohol, trihydric alcohol, and an alcohol having four or more OH groups.

Examples of the monohydric alcohol include a straight chain monohydric alcohol, and a branched monohydric alcohol.

Examples of the straight chain monohydric alcohol include methanol, ethanol, n-propanol, n-butanol, n-pentanol, n-hexanol, n-heptanol, n-octanol, n-nonanol, n-decanol, n-undecanol, n-dodecanol (lauryl alcohol), n-tridecanol, n-tetradecanol, n-pentadecanol, n-hexadecanol, n-heptadecanol, n-octadecanol (stearyl alcohol), n-nonadecanol, and eicosanol.

Examples of the branched monohydric alcohol include isopropanol, isobutanol, sec-butanol, tert-butanol, isopentanol, isohexanol, isoheptanol, iso-octanol, 2-ethylhexane-1-ol, isononanol, isodecanol, 5-ethyl-2-nonanol, trimethylnonylalcohol, 2-hexyldecanol, 3,9-diethyl-6-tridecanol, 2-isoheptylisoundecanol, 2-octyldodecanol, and other branched alkanol (C (the number of carbons, the same applied to the following) 5 to 20).

Examples of the dihydric alcohol include straight chain dihydric alcohols such as ethylene glycol, 1,3-propanediol, 1,4-butyleneglycol, 1,5-pentanediol, 1,6-hexanediol, 1,4-dihydroxy-2-butene, diethylene glycol, triethylene glycol, dipropylene glycol, and other straight chain alkane (C7 to 20) diols; branched dihydric alcohols such as 1,2-propanediol, 1,3-butyleneglycol, 1,2-butyleneglycol, neopentyl glycol 3-methyl-1,5-pentanediol, 2,2,2-trimethylpentanediol, 3,3-dimethylolheptane, 2,6-dimethyl-1-octene-3,8-diol, and other branched alkane (C7 to 20) diols; 1,3- or 1,4-cyclohexanedimethanol and a mixture thereof; 1,3- or 1,4-cyclohexanediol and a mixture thereof; hydrogenated bisphenol A; and bisphenol A.

Examples of the trihydric alcohol include glycerin, and trimethylolpropane.

Examples of the alcohol having four or more OH groups include tetramethylolmethane, D-sorbitol, xylitol, and D-mannitol.

These alcohols contain one or more hydroxy group in its molecule, and the molecular structure other than that is not particularly limited, as long as it does not hinder excellent effects of the present invention. For example, an ester group, an ether group, a cyclohexane ring, and an aromatic ring may be contained in its molecule. Examples of such alcohols include an ether group-containing monohydric alcohol obtained by addition polymerization of the above-described monohydric alcohol and alkylene oxide (e.g., ethylene oxide, propylene oxide, etc.) (random and/or block polymer of two or more alkylene oxides); and the ester group-containing monohydric alcohol obtained by addition polymerization of the above-described monohydric alcohol and lactone (e.g., ε-polycaprolactone, δ-valerolactone, etc.).

These alcohols may be used singly or in a combination of two or more.

As alcohols, preferably, mono and dihydric alcohols are used, and as the mono and dihydric alcohols, preferably mono and dihydric alcohol having 1 to 20 carbon atoms, and more preferably mono and dihydric alcohol having 1 to 15 carbon atoms, and more preferably mono and dihydric alcohol having 1 to 10 carbon atoms, and particularly preferably mono and dihydric alcohol having 2 to 6 carbon atoms are used.

As the mono and dihydric alcohol, preferably, branched mono and dihydric alcohols are used.

To further decrease the viscosity of the polyisocyanate composition, most preferably, monohydric alcohols are used.

Alcohols are used so that the average functionality in the obtained polyisocyanate composition is 2 or more, and the mixing ratio of the alcohols relative to 100 parts by mass of pentamethylene diisocyanate is, 0.1 to 5 parts by mass, preferably 0.2 to 3 parts by mass.

In the trimerization reaction of pentamethylene diisocyanate, as necessary, with the above-described alcohols, an active hydrogen compound such as, for example, thiols, oximes, lactams, phenols, and β diketones may be used in combination within the range that does not hinders excellent effects of the present invention.

In the present invention, pentamethylene diisocyanate and alcohols are allowed to react so that the isocyanate group concentration in the obtained polyisocyanate composition is, for example, 10 to 28 mass %.

To allow reaction between pentamethylene diisocyanate and alcohols so that the isocyanate group concentration is within the above-described range, after allowing pentamethylene diisocyanate and alcohols to react, in the presence of a trimerization catalyst, they are subjected to trimerization reaction under predetermined reaction conditions.

The trimerization catalyst is not particularly limited, as long as the catalyst is effective in trimerization, and examples thereof include hydroxide of tetraalkylammonium or its organic salt of weak acid such as tetramethyl ammonium, tetraethyl ammonium, tetrabutyl ammonium, trimethylbenzyl ammonium; trialkylhydroxyalkyl ammonium hydroxide or its organic salt of weak acid such as trimethylhydroxypropyl ammonium, trimethylhydroxyethyl ammonium, triethylhydroxypropyl ammonium, and tri ethylhydroxyethyl ammonium; alkali metal salt of alkylcarboxylic acid such as acetic acid, caproic acid, octylic acid, and myristic acid; metal salts of tin, zinc, and lead of the above-described alkylcarboxylic acid; metal chelate compounds of β-diketone such as aluminum acetylacetone, and lithium acetylacetone; Friedel-Crafts catalysts such as aluminum chloride, and boron trifluoride; various organic metal compounds such as titaniumtetrabutyrate, and tributyl antimony oxide; aminosilyl group-containing compounds such as hexamethylsilazane.

To be specific, for example, Zwitter ionic hydroxyalkyl quaternary ammonium compounds are used, to be more specific, for example, N-(2-hydroxypropyl)-N,N,N-trimethylammonium-2-ethylhexanoate, N,N-dimethyl-N-hydroxyethyl-N-2-hydroxypropylammonium•hexanoate, triethyl-N-2-hydroxypropylammonium hexadecanoate•trimethyl-N-2-hydroxypropylammonium•phenylcarbonate, and trimethyl-N-2-hydroxypropylammonium•formate.

These trimerization catalysts may be used singly or in a combination of two or more.

As the trimerization catalyst, preferably, N-(2-hydroxypropyl)-N,N,N-trimethylammonium-2-ethylhexanoate is used.

The trimerization catalyst is added, relative to 100 parts by mass of pentamethylene diisocyanate, for example, 0.0005 to 0.3 parts by mass, preferably 0.001 to 0.1 parts by mass, more preferably 0.001 to 0.05 parts by mass.

To adjust trimerization, for example, organic phosphite such as the ones shown in Japanese Unexamined Patent Publication No. Sho 61-129173 may be used as a promoter.

Examples of the organic phosphite include organic phosphorous acid diester and organic phosphorous acid triester, to be more specific, for example, monophosphites such as triethylphosphite, tributylphosphite, tris(2-ethylhexyl) phosphite, tridecylphosphite, trilaurylphosphite, tris(tridecyl) phosphite, tristearylphosphite, triphenylphosphite, tris(nonylphenyl) phosphite, tris(2,4-di-t-butylphenyl) phosphite, diphenyldecylphosphite, diphenyl (tridecyl) phosphite; di, tri, or tetraphosphites derived from polyhydric alcohols such as distearyl•pentaerythrityl•diphosphite, di•dodecyl•pentaerythritol•diphosphite, di•tridecyl•pentaerythritol•diphosphite, dinonylphenyl•pentaerythritol•diphosphite•tetraphenyl• tetra•tridecyl•pentaerythrityl•tetraphosphite•tetraphenyl• dipropylene glycol•diphosphite, and tripentaerythritol•triphosphite; diphosphites derived from bisphenol compounds such as di•alkyl•bisphenol A•diphosphite having 1 to 20 carbon atoms, and 4,4'-butylidene-bis(3-methyl-6-t-butylphenyl-di•tridecyl) phosphite; polyphosphites such as hydrogenated bisphenol A phosphite polymer (molecular weight 2400 to 3000); and tris(2,3-dichloropropyl) phosphite.

In this reaction, a stabilizer including a hindered phenol antioxidant such as, for example, 2,6-di(tert-butyl)-4-methylphenol, IRGANOX 1010, IRGANOX 1076. IRGANOX 1135, IRGANOX 245 (all manufactured by Ciba Japan, K.K. trade name) can also be added.

The predetermined reaction conditions are, for example, under an atmosphere of inactive gas such as nitrogen gas, and under a normal pressure (atmospheric pressure) and a reaction temperature of, for example, 30 to 100° C., preferably 40 to 80° C., and a reaction time of, for example, 0.5 to 10 hours, preferably 1 to 5 hours.

In this reaction, pentamethylene diisocyanate and alcohols are blended at a mixing ratio so that the equivalent ratio (NCO/OH) of the isocyanate group of pentamethylene diisocyanate relative to the hydroxy group of alcohols is, for example, 20 or more, preferably 30 or more, more preferably 40 or more, particularly preferably 60 or more, and usually 1000 or less.

After reaching a predetermined isocyanate group concentration the above-described trimerization catalyst is added to conduct trimerization reaction.

The conversion rate of the isocyanate group in this reaction is, for example, 5 to 35 mass %, preferably 5 to 30 mass %, more preferably 5 to 25 mass %.

When the conversion rate is more than 35 mass %, the number average molecular weight of the obtained polyisocyanate composition becomes high, and its solubility, compatibility, and NCO content (isocyanate group concentration) may decrease, and viscosity may become high. In contrast, when the conversion rate is below 5 mass %, productivity of the polyisocyanate composition may not be sufficient.

The conversion rate of the isocyanate group can be measured, for example, based on high-performance GPC, NMR, the isocyanate group concentration, refractive index, density, and infrared spectrum.

In this reaction, as necessary, a known reaction solvent may be blended, and furthermore, at an arbitrary timing, a known catalyst deactivation agent (e.g., phosphoric acid, monochloroacetic acid, dodecylbenzenesulfonic acid, p-toluenesulfonic acid, benzoyl chloride, etc.) can be added.

Then, after the termination of reaction, unreacted pentamethylene diisocyanate is, as necessary, removed by a known removal method such as distillation.

As a method to obtain a polyisocyanate composition, when a method is used in which after only pentamethylene diisocyanate is subjected to trimerization unreacted pentamethylene diisocyanate is removed, and the obtained trimer and alcohols are allowed to react (the latter method of the above), the reaction between trimer and alcohols is a general urethane-forming reaction. The reaction conditions for such a urethane-forming reaction are, for example, a room temperature to 100° C., preferably 40 to 90° C.

In the above-described urethane-forming reaction, as necessary, for example, a known urethanizing catalyst such as amines and organic metal compounds can be added.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organic metal compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as copper octenate; organic bismuth compounds such as bismuth octylate and bismuth neodecanoate.

Examples of urethanizing catalysts also include potassium salts such as potassium carbonate, potassium acetate, and potassium octoate.

These urethanizing catalysts may be used singly or in a combination of two or more.

The method for obtaining the polyisocyanate composition is not limited to the above-described methods, and for example, pentamethylene diisocyanate can also be subjected to, in the same manner as described above, trimerization reaction without using alcohols in the presence of the above-described trimerization catalyst.

The above-described polyisocyanate composition can contain, for example, a compound containing a sulfonamide group.

In the present invention, examples of the compound containing sulfonamide groups include aromatic sulfonamides, and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in a combination of two or more.

As the compound containing a sulfonamide group, preferably, aromatic sulfonamides are used, more preferably, o- or p-toluene sulfonamides are used.

When the polyisocyanate composition contains a compound containing a sulfonamide group, for example, 10 to 5000 ppm, preferably 50 to 4000 ppm, more preferably 100 to 3000 ppm of the compound containing a sulfonamide group is contained, relative to the polyisocyanate composition.

When more than 5000 ppm of the compound containing a sulfonamide group is contained, the isocyanate group concentration may change in the polyisocyanate composition storage step, and in the polyurethane resin production step. In contrast, when below 10 ppm of the compound containing a sulfonamide group is contained, viscosity and color may be significantly changed in the polyisocyanate composition storage step, and in the polyurethane resin production step.

The method for allowing the polyisocyanate composition to contain the compound containing a sulfonamide group is not particularly limited, and for example, in the trimerization reaction of pentamethylene diisocyanate, the compound containing a sulfonamide group can be added along with pentamethylene diisocyanate and alcohols, or the compound containing a sulfonamide group can be added to the polyisocyanate composition obtained by the trimerization reaction of pentamethylene diisocyanate.

The thus obtained polyisocyanate composition has an isocyanate group concentration of for example, 10 to 28 mass %, preferably 15 to 28 mass %, more preferably, 20 to 28 mass %.

The thus obtained polyisocyanate composition (trimer modified substance), has an isocyanate trimer (isocyanate modified substance having an isocyanurate group (and, sometimes iminooxadiazinedione group) and having a molecular weight of triple the isocyanate monomer) concentration (concentration excluding impurities such as unreacted pentamethylene diisocyanate) of for example, 35 to 95 mass %, preferably 40 to 85 mass %, more preferably 50 to 75 mass %.

When the isocyanate trimer concentration is below 35 mass %, disadvantages such as the following may be caused: the viscosity of the polyisocyanate composition increases, and crosslinking effects is reduced.

The thus obtained polyisocyanate composition contains an isocyanate monomer concentration (unreacted pentamethylene diisocyanate concentration) of, for example, 3 mass % or less, preferably 1.5 mass % or less, more preferably 1 mass % or less.

The thus obtained polyisocyanate composition may contain, in addition to the isocyanurate bond and/or iminooxadiazinedione bond, an allophanate bond. In such a case, the molar ratio ((isocyanurate group (number of moles)+iminooxadiazinedione group (number of moles))/allophanate group (number of moles)) of the isocyanurate group and the iminooxadiazinedione group relative to the allophanate group in the polyisocyanate composition is for example, 1 to 3500, preferably 1 to 3000, more preferably 1 to 1000.

The molar ratio of the isocyanurate group and the iminooxadiazinedione group relative to the allophanate group in the polyisocyanate composition can be measured by a known method, to be more specific, for example, can be calculated by determining peak ratio (area ratio) in the chromatogram (chart) of gel permeation chromatograph (GPC) equipped with a refractive index detector (RID), or by NMR method.

The thus obtained polyisocyanate composition has a viscosity at 25° C. of, for example, 100 to 8000 mPa·s, preferably 200 to 6000 mPa·s, more preferably 300 to 4000 mPa·s, even more preferably 500 to 2000 mPa·s.

The above-described polyisocyanate composition (trimer modified substance) can be obtained by subjecting the above-described pentamethylene diisocyanate to trimerization. Thus, the above-described polyisocyanate composition is produced efficiently, and has excellent storage stability.

Furthermore, the thus obtained polyisocyanate composition can be applied to various industrial use such as, for example, coating, adhesive, and others without diluting with a solvent. As necessary, the thus obtained polyisocyanate composition can also be dissolved in various organic solvents and used.

Examples of organic solvents include ketones such as acetone, methyl ethyl ketone, methylisobutylketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethylether acetate, propylene glycol methylether acetate, 3-methyl-3-methoxybutyl acetate, and ethyl-3-ethoxypropionate; ethers such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotic solvents such as N-methylpyrrolidone, dimethylformamide, N,N'-dimethylacetamide, dimethyl sulfoxide, and hexamethyl phosphoramide.

Examples of organic solvents include nonpolar solvents (nonpolar organic solvent), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetal oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.), Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also turpentine oils such as methylcyclohexane (aniline point 40° C.), ethylcyclohexane (aniline point 44° C.), and gum turpentine N (manufactured by YASUHARA CHEMICAL CO., LTD., aniline point 27° C.).

The polyisocyanate composition of the present intention can be mixed with these organic solvents at an arbitrary proportion.

Furthermore, the polyisocyanate composition of the present invention can also be used as a blocked isocyanate in which free isocyanate groups contained in the molecule are blocked by blockers.

The blocked isocyanate can be produced, for example, by allowing the polyisocyanate composition to react with the blocker.

Examples of blockers include blockers of oxime, phenol, alcohol, imine, amine, carbamic acid, urea, imidazole, imide, mercaptan, active methylene, acid amide (lactam), and bisulfites.

Examples of the oxime blocker include formaldoxime, acetaldoxime, methyl ethyl ketone oxime, cyclohexanoneoxime, acetoxime, diacetyl monoxime, benzophenone oxime, 2,2,6,6-tetramethylcyclohexanoneoxime, diisopropylketoneoxime, methyltert-butylketoneoxime, diisobutylketoneoxime, methylisobutylketoneoxime, methylisopropylketoneoxime, methyl 2,4-dimethylpentylketoneoxime, methyl 3-ethylheptylketoneoxime, methyl isoamyl ketoneoxime, n-amylketoneoxime, 2,2,4,4-tetramethyl-1,3-cyclobutanedionemonoxime, 4,4'-dimethoxybenzophenoneoxime and 2-heptanoneoxime.

Examples of phenol blockers include phenol, cresol, ethylphenol, n-propylphenol, isopropylphenol, n-butylphenol, sec-butylphenol, tert-butylphenol, n-hexylphenol, 2-ethylhexylphenol, n-octylphenol, n-nonylphenol, di-n-propylphenol, diisopropylphenol, isopropylcresol, di-n-butylphenol, di-sec-butylphenol, di-tert-butylphenol, di-n-octylphenol, di-2-ethylhexylphenol, di-n-nonylphenol, nitrophenol, bromophenol, chlorophenol, fluorophenol, dimethylphenol, styrenated phenol, methylsalicylate, 4-hydroxybenzoic acid methyl ester, 4-hydroxybenzoic acid benzyl ester, hydroxybenzoic acid 2-ethylhexyl ester, 4-[(dimethylamino) methyl] phenol, 4-[(dimethylamino) methyl]nonylphenol, bis(4-hydroxyphenyl) acetic acid, pyridinol, 2- or 8-hydroxyquinoline, 2-chloro-3-pyridinol, and pyridine-2-thiol.

Examples of the alcohol blocker include, for example, methanol, ethanol, 2-propanol, n-butanol, sec-butanol, 2-ethylhexylalcohol, 1- or 2-octanol, cyclohexylalcohol, ethylene glycol, benzylalcohol, 2,2,2-trifluoroethanol, 2,2,2-trichloroethanol, 2-(hydroxymethyl) furan, 2-methoxyethanol, methoxypropanol, 2-ethoxyethanol, n-propoxyethanol, 2-butoxyethanol, 2-ethoxyethoxyethanol, 2-ethoxybutoxyethanol, butoxyethoxyethanol, 2-ethylhexyloxyethanol, 2-butoxyethanol, 2-butoxyethoxyethanol, N,N-dibutyl-2-hydroxyacetamido, N-hydroxysuccinimide, N-morpholine ethanol, 2,2-dimethyl-1,3-dioxolane-4-methanol, 3-oxazolidine ethanol, 2-hydroxymethylpyridine, furfuryl alcohol, 12-hydroxystearic acid, triphenylsilanol, and methacrylic acid 2-hydroxyethyl ester.

Examples of the imine blocker include ethyleneimine, polyethyleneimine, 1,4,5,6-tetrahydropyrimidine, and guanidine.

Examples of the amine blocker include dibutylamine, diphenylamine, aniline, N-methylaniline, carbazole, bis(2,2,6,6-tetramethylpiperidinyl)amine, di-n-propylamine, diisopropylamine, isopropylethylamine, 2,2,4-, or 2,2,5-trimethylhexamethyleneamine, N-isopropylcyclohexylamine, dicyclohexylamine, bis(3,5,5-trimethylcyclohexyl)amine, piperidine, 2,6-dimethylpiperidine, 2,2,6,6-tetramethylpiperidine, (dimethylamino)-2,2,6,6-tetramethylpiperidine, 2,2,6,6-tetramethyl-4-piperidine, 6-methyl-2-piperidine, and 6-aminocaproic acid.

Examples of the carbamic acid blocker include N-phenylcarbamate phenyl.

Examples of the urea blocker include urea, thiourea, and ethyleneurea.

Examples of the imidazole blocker include imidazole, 2-methylimidazole, 2-ethyl-4-methylimidazole, 2-isopropyl imidazole, 2,4-dimethylimidazole, 4-methylimidazole, 2-phenylimidazole, 4-methyl-2-phenylimidazole, pyrazole, 3-methylpyrazole, 3,5-dimethylpyrazole, 1,2,4-triazole, and benzotriazole.

Examples of the imide blocker include succinic acidimide, maleic acidimide, and phthal imide.

Examples of the mercaptan blocker include butylmercaptan, dodecylmercaptan, and hexylmercaptan.

Examples of the active methylene blocker include Meldrum's acid, malonic acid dimethyl ester, methyl acetoacetate, ethyl acetoacetate, malonic acid di-tert-butyl ester, malonic acid 1-tert-butyl 3-methyl ester, malonic acid diethyl ester, acetoacetic acid tert-butyl ester, 2-acetylacetoxyethylmethacrylate, acetylacetone, and cyanoethyl acetate.

Examples of the acid amide (lactam) blocker include acetanilide, N-methylacetamide, acetic acidamide, ε-caprolactam, δ-valerolactam, γ-butyrolactam, pyrrolidone, 2,5-piperazine dione, and laurolactam.

The blocker is not limited to the above, and for example, other blockers such as benzoxazolone, isatoic acid anhydride, and tetrabutylphosphonium•acetate can be used.

These blockers may be used singly or in a combination of two or more.

As the blocker, those blockers that dissociate at preferably 200° C. or less, preferably 100 to 180° C. are used. To be more specific, for example, active methylene compounds such as ethyl acetoacetate, or oximes such as methyl ethyl ketone oxime are used.

The blocked isocyanate can be obtained by blending a polyisocyanate composition with a blocker at a proportion such that the blocker is excessive relative to the isocyanate group in the polyisocyanate composition, and then allowing the mixture to react under known conditions.

The polyisocyanate composition of the present invention can be used as an aqueous blocked isocyanate in which free isocyanate groups contained in the molecule are blocked by a blocker, and which is dispersed or dissolved in water.

The method for producing aqueous blocked isocyanate is not particularly limited, and for example, can be produced by the following method: first, a polyisocyanate composition (hereinafter partly blocked isocyanate) in which a portion of the free isocyanate groups in the polyisocyanate composition is blocked with a blocker is produced, and thereafter, the free isocyanate groups (remained isocyanate groups without being blocked by a blocker) in the partly blocked isocyanate is allowed to react with a compound (hereinafter hydrophilic group-containing active hydrogen compound) having both of a hydrophilic group and an active hydrogen group.

In this method, first, a portion of the free isocyanate groups in the polyisocyanate composition is allowed to react with a blocker to produce a partly blocked isocyanate.

Examples of the blocker include those blockers described above.

The partly blocked isocyanate can be obtained by blending a polyisocyanate composition with a blocker at a proportion such that the isocyanate group in the polyisocyanate composition is excessive relative to the blocker, and then allowing the mixture to react under known conditions.

Next, in this method, the free isocyanate group (the remaining portion of the isocyanate group) of the partly blocked isocyanate is allowed to react with a hydrophilic group-containing active hydrogen compound.

The hydrophilic group-containing active hydrogen compound is a compound having both of at least one hydrophilic group and at least one active hydrogen group, and examples of the hydrophilic group include an anionic group, a cationic group, and a nonionic group. Examples of the active hydrogen group include those groups that react with isocyanate groups, such as a hydroxyl group, an amino group, a carboxyl group, and an epoxy group.

Examples of the hydrophilic group-containing active hydrogen compound include, to be more specific, a carboxylic acid group-containing active hydrogen compound, a sulfonic acid group-containing active hydrogen compound, a hydroxyl group-containing active hydrogen compound, a hydrophilic group-containing polybasic acid, and a polyoxyethylene group-containing active hydrogen compound.

Examples of the carboxylic acid group-containing active hydrogen compound include dihydroxyl carboxylic acid such as 2,2-dimethylol acetic acid, 2,2-dimethylol lactic acid, 2,2-dimethylol propionic acid (DMPA), 2,2-dimethylolbutanoic acid (DMBA), 2,2-dimethylol butyric acid, 2,2-dimethylol valeric acid; diaminocarboxylic acid such as lysine and arginine; and their metal salts and ammonium salts. Preferably, 2,2-dimethylolpropionic acid (DMPA), or 2,2-dimethylolbutanoic acid (DMBA) is used.

Examples of the sulfonic acid group-containing active hydrogen compound include dihydroxybutane sulfonic acid and dihydroxypropane sulfonic acid that are obtained from synthesis reaction between an epoxy group-containing compound and acid sulfite. Examples also include N,N-bis(2-hydroxyethyl)-2-aminoethanesulfonic acid, N,N-bis(2-hydroxyethyl)-2-aminobutanesulfonic acid, 1,3-phenylenediamine-4,6-disulfonic acid, diaminobutanesulfonic acid, diaminopropane sulfonic acid, 3,6-diamino-2-toluenesulfonic acid, 2,4-diamino-5-toluenesulfonic acid, N-(2-aminoethyl)-2-aminoethanesulfonic acid, 2-aminoethanesulfonic acid, N-(2-aminoethyl)-2-aminobutanesulfonic acid, and metal salts and ammonium salts of those sulfonic acids.

Examples of the hydroxyl group-containing active hydrogen compound include N-(2-aminoethyl)ethanolamine.

Examples of the hydrophilic group-containing polybasic acid include polybasic acid containing sulfonic acid, to be more specific, 5-sulfoisophthalic acid, sulfoterephthalic acid, 4-sulfophthalic acid, 5-(p-sulfophenoxy) isophthalic acid, 5-(sulfopropoxy) isophthalic acid, 4-sulfonaphthalene-2,7-dicarboxylic acid, sulfopropylmalonic acid, sulfosuccinic acid, 2-sulfobenzoic acid, 2,3-sulfobenzoic acid, 5-sulfosalicylic acid, alkyl ester of those carboxylic acids, and also metal salts and ammonium salts of those sulfonic acids. Preferably, sodium salts of 5-sulfoisophthalic acid, or sodium salts of 5-sulfoisophthalic acid dimethyl ester are used.

The polyoxyethylene group-containing active hydrogen compound is a compound containing a polyoxyethylene group in the main chain or side chain, and having at least one active hydrogen group.

As the polyoxyethylene group-containing active hydrogen compound, for example, polyethylene glycol (e.g., number average molecular weight 200 to 6000, preferably 300 to 3000), or a polyoxyethylene side chain-containing polyol is used.

The polyoxyethylene side chain-containing polyol contains a polyoxyethylene group in its side chain, and is a compound having two or more active hydrogen groups. The polyoxyethylene side chain-containing polyol can be synthesized in the following manner.

That is, first, diisocyanate (described later) and a one-end-terminated polyoxyethylene glycol (e.g., alkoxyethylene glycol with its one end capped with an alkyl group having 1 to 4 carbon atoms, number average molecular weight 200 to 6000, preferably 300 to 3000) are subjected to urethane-forming reaction at such a proportion that the isocyanate group of diisocyanate (described later) is excessive relative to the hydroxyl group of the one-end-terminated polyoxyethylene glycol, and as necessary, unreacted diisocyanate (described later) is removed, thereby producing a polyoxyethylene chain-containing monoisocyanate.

Then, the polyoxyethylene chain-containing monoisocyanate and dialkanolamine (e.g., diethanolamine, etc.) are subjected to urea reaction at such a proportion that the isocyanate group of the polyoxyethylene group-containing monoisocyanate is substantially equal with the secondary amino group of dialkanolamine.

The diisocyanate for obtaining the polyoxyethylene side chain-containing polyol is not particularly limited, and a known diisocyanate may be used. As the diisocyanate, to be more specific, for example, aliphatic diisocyanates such as pentamethylene diisocyanate (PDI) (including pentamethylene diisocyanate of the present invention), and hexamethylenediisocyanate (HDI); and alicyclic diisocyanates such as 1,4- or 1,3-bis(isocyanatomethyl)cyclohexane (H6XDI), 3-isocyanatomethyl-3,5,5-trimethylcyclohexyl isocyanate (also called: isophorone diisocyanate (IPDI), 4,4'-methylenebis(cyclohexyl isocyanate)(H12MDI), and 2,6-bis(isocyanatomethyl) norbornane (NBDI) are used.

As the polyoxyethylene group-containing active hydrogen compound, furthermore, for example, monohydric alcohol (e.g., polyoxyethylenelaurylether, polyoxyethyleneoleylether, polyoxyethylenestearylether, etc.) to which ethylene oxide is added, polyoxyethylene-containing sorbitan esters (e.g., polyoxyethylene sorbitan oleate, polyoxyethylene sorbitan ricinoleate, polyoxyethylene sorbitan oleate, etc.), polyoxyethylene-containing alkylphenols (e.g., polyoxyethyleneoctylphenolether, polyoxyethylenenonylphenolether, etc.), polyethylene glycol-containing higher fatty acid esters (e.g., polyethylene glycollaurate, polyethylene glycol oleate, polyethylene glycolstearate, etc.) are also used.

The aqueous blocked isocyanate can be obtained by blending the partly blocked isocyanate and a hydrophilic group-containing active hydrogen compound at such a proportion that the hydrophilic group-containing active hydrogen compound is excessive relative to the free isocyanate group of the partly blocked isocyanate, and are subjected to reaction under known conditions.

Then, the polyurethane resin of the present invention can be obtained by allowing the above-described pentamethylene diisocyanate, and/or the above-described polyisocyanate composition (hereinafter may be generally referred to as a polyisocyanate component), and an active hydrogen compound to react.

Examples of active hydrogen compounds include a polyol component (component containing mainly polyol having two or more hydroxyl groups), and a polyamine component (compound containing mainly polyamine having two or more amino groups).

The active hydrogen compound contains, as an essential component, a polyol component, and the polyurethane resin at least has a urethane bond formed by reaction between the isocyanate group in the polyisocyanate component and the hydroxyl group in the polyol component.

Examples of polyol component in the present invention include low-molecular-weight polyols and high-molecular weight polyols.

Low-molecular-weight polyols are compounds having two or more hydroxyl groups and a number average molecular weight of below 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C7 to 20) diol, 1,3- or 1,4-cyclohexanedimethanol and a mixture thereof 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, and dipropylene glycol; trihydric alcohols such as glycerin, and trimethylolpropane; tetrahydric alcohols such as tetramethylolmethane (pentaerythritol), and diglycerol; pentahydric alcohol such as xylitol; hexahydric alcohols such as sorbitol, mannitol, allitol, iditol, dulcitol, altritol, inositol, and dipentaerythritol; heptahydric alcohol such as perseitol; and octahydric alcohols such as sucrose.

These low-molecular-weight polyols may be used singly or in a combination of two or more.

High-molecular weight polyols are compounds having two or more hydroxyl groups and having a number average molecular weight of 400 or more, and examples thereof include polyetherpolyol, polyester polyol, polycarbonate polyol, polyurethane polyol, epoxy polyol, vegetable oil polyol, polyolefin polyol, acrylic polyol, and vinyl monomer-modified polyol.

Examples of polyetherpolyols include polypropylene glycol, and polytetramethylene ether glycol.

Examples of polypropylene glycols include addition polymerized product (including random and/or block copolymer of two or more alkylene oxides) of alkylene oxides such as ethylene oxide and propylene oxide using the above-described low-molecular-weight polyol or the aromatic/aliphatic polyamine as an initiator.

Examples of polytetramethylene ether glycols include ring-opening polymerized product obtained by cation polymerization of tetrahydrofuran, and noncrystalline polytetramethylene ether glycol obtained by copolymerizing polymerization unit of tetrahydrofuran and the above-described dihydric alcohol.

Examples of polyester polyols include a polycondensation product obtained by allowing the above-described low-molecular-weight polyol and polybasic acid to react under known conditions.

Examples of polybasic acids include saturated aliphatic dicarboxylic acids (C11 to 13) such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, sebacic acid, etc.; unsaturated aliphatic dicarboxylic acids such as maleic acid, fumaric acid, itaconic acid, etc.; aromatic dicarboxylic acids such as orthophthalic acid, isophthalic acid, terephthalic acid, toluenedicarboxylic acid, naphthalenedicarboxylic acid, etc.; alicyclic dicarboxylic acids such as hexahydrophthalic acid, etc.; other carboxylic acids such as dimer acid, hydrogenated dimer acid, het acid, etc. and acid anhydrides derived from these carboxylic acids such as oxalic anhydride, succinic anhydride, maleic anhydride, phthalic anhydride, 2-alkyl (C12 to C18) succinic anhydride, tetrahydrophthalic anhydride, trimellitic anhydride, and hallides derived from carboxylic acids thereof such as oxalyl dichloride, adipoyl dichloride, and sebacoyl dichloride.

Examples of polyester polyols include plants derived polyester polyol, to be specific, vegetable oil polyester polyols obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, lactic acid, etc.) using the above-described low-molecular-weight polyol as an initiator under known conditions.

Examples of polyester polyols include polycaprolactone polyol, and polyvalerolactone polyol obtained by ring-opening polymerization of lactones such as ε-caprolactone, γ-valerolactone, etc. and lactides such as L-lactide, D-lactide using the above-described low-molecular-weight polyols (preferably, dihydric alcohol) as an initiator; and further lactone-based polyester polyols obtained by copolymerizing such a polycaprolactone polyol or polyvalerolactone polyol with the above-described dihydric alcohol.

Examples of polycarbonate polyols include ring-opening polymerization product of ethylene carbonate using the above-described low-molecular-weight polyols (preferably, dihydric alcohol) as an initiator, and noncrystalline polycarbonate polyols obtained by copolymerization of dihydric alcohols such as 1,4-butanediol, 1,5-pentanediol, 3-methyl-1,5-pentanediol, and 1,6-hexanediol with ring-opening polymerization product.

Polyurethane polyols can be obtained as polyester polyurethane polyol, polyether polyurethane polyol, polycarbonate polyurethane polyol, or polyester polyether polyurethane polyol, by allowing polyester polyol, polyetherpolyol and/or polycarbonate polyol obtained as described above to react with polyisocyanate at an equivalent ratio (OH/NCO) of hydroxyl group (OH) to isocyanate group (NCO) of more than 1.

Examples of epoxy polyols include epoxy polyols obtained by reaction of the above-described low-molecular-weight polyols with polyfunctional halohydrin such as epichlorohydrin, β-methylepichlorohydrin, etc.

Examples of vegetable oil polyols include hydroxyl group-containing vegetable oil such as castor oil, palm oil, etc. Examples thereof include ester-modified castor oil polyol obtained by reaction of castor oil polyol or castor oil fatty acid with polypropylene polyol.

Examples of polyolefin polyols include polybutadiene polyol, and a partially saponified ethylene-vinyl acetate copolymer.

Examples of acrylic polyol include copolymers obtained by copolymerizing hydroxyl group-containing acrylate with a copolymerizable vinyl monomer that is copolymerizable with hydroxyl group-containing acrylate.

Examples of hydroxyl group-containing acrylates include 2-hydroxyethyl (meth)acrylate, hydroxypropyl (meth)acrylate, hydroxybutyl (meth)acrylate, 2,2-dihydroxymethylbutyl (meth)acrylate, polyhydroxyalkylmaleate, and polyhydroxyalkylfumarate. Preferably, 2-hydroxyethyl (meth) acrylate is used.

Examples of copolymerizable vinyl monomers include alkyl (meth)acrylate (1 to 15 carbon atoms) such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, isopentyl (meth)acrylate, hexyl (meth)acrylate, isononyl (meth)acrylate, 2-ethylhexyl (meth) acrylate, cyclohexylacrylate, and isobornyl (meth)acrylate; aromatic vinyls such as styrene, vinyltoluene, and α-methylstyrene; vinyl cyanide such as (meth)acrylonitrile; vinyl monomers containing carboxyl groups such as (meth)acrylic acid, fumaric acid, maleic acid, and itaconic acid or their alkyl esters; alkanepolyol poly (meth)acrylate such as ethylene glycol di(meth)acrylate, butyleneglycol di(meth)acrylate, hexanediol di(meth)acrylate, oligoethylene glycol di(meth) acrylate, trimethylolpropane di(meth)acrylate, and trimethylolpropane tri(meth)acrylate; and vinyl monomers containing isocyanate groups such as 3-(2-isocyanato-2-propyl)-α-methylstyrene.

Acrylic polyol can be obtained by copolymerizing these hydroxyl group-containing acrylate, and copolymerizable vinyl monomers in the presence of an appropriate solvent and a polymerization initiator.

Examples of acrylic polyol include silicone polyol and fluorine polyol.

Examples of silicone polyols include acrylic polyol in which as the copolymerizable vinyl monomer, for example, a silicone compound containing a vinyl group such as γ-methacryloxypropyltrimethoxysilane is blended in the above-described copolymerization of acrylic polyol.

Fluorinepolyol is a copolymer of fluoroolefin and a monomer containing a double bond that is copolymerizable with fluoroolefin. The fluorinepolyol is a weak solvent soluble fluorine-containing copolymer, containing 10 mass % or more fluorine based on fluoroolefin, containing 5 to 30 mol % of a hydroxyl group in the double bond-containing monomer, and containing 10 to 50 mol % of branched alkyl group having three or more carbons.

The fluoroolefin is, in view of weather resistance, a fluoroolefin preferably having a fluorine addition number of 2 or more, more preferably 3 to 4. To be specific, for example, tetrafluoroethylene, chlorotrifluoroethylene, vinylidene fluoride, hexafluoropropylene are used, and preferably, tetrafluoroethylene, or chlorotrifluoroethylene is used. These fluoroolefins may be used singly or in a combination of two or more.

The double bond-containing monomer is copolymerizable with fluoroolefin, and preferably a vinyl monomer other than fluoroolefin is used. The vinyl monomer is a compound having a carbon-carbon double bond represented by CH2=CH—. Examples of the vinyl monomer include alkylvinylether and alkylvinyl ester having a straight chain, branched, or cyclic alkyl group.

The double bond monomer includes both a double bond-containing monomer (hereinafter referred to as a hydroxyl group-containing monomer) containing a hydroxyl group and a double bond-containing monomer (hereinafter referred to as a branched alkyl group-containing monomer) containing branched alkyl group having 3 or more carbons. The hydroxyl group-containing monomer may contain a branched alkyl group having 3 or more carbons, or the branched alkyl group-containing monomer may contain a hydroxyl group.

Of the double bond-containing monomer, 5 to 30 mol % contains a hydroxyl group. When the hydroxyl group-containing monomer content is 5 mol % or more, a coating with a high hardness can be produced, and when the hydroxyl group-containing monomer content is 30 mol % or less, sufficient solubility can be maintained in a weak solvent.

The number of carbons in the hydroxyl group-containing monomer is not particularly limited, and for example, 2 to 10, preferably 2 to 6, more preferably, 2 to 4.

Examples of such hydroxyl group-containing monomers include hydroxyalkylvinylethers such as 4-hydroxybutylvinyl ether (HBVE), 2-hydroxyethylvinyl ether, and cyclohexanedimethanol monovinyl ether; hydroxyalkylallylethers such as hydroxyethylallylether, and cyclohexanedimethanol monoallyl ether; and (meth)acrylic acid hydroxyalkyl esters such as hydroxyethyl (meth)acrylate.

In view of excellent copolymerizability, and improvement in weather resistance of the coating to be formed, preferably, hydroxyalkylvinylethers are used. In particular, in view of excellent solubility in weak solvent, preferably, hydroxyalkylvinylether having 2 to 4 carbon atoms, more preferably, HBVE is used. These hydroxyl group-containing monomer may be used singly or in a combination of two or more.

Of the double bond-containing monomer, 10 to 50 mol % contains a branched alkyl group having 3 or more carbon atoms. When the branched alkyl group-containing monomer is contained in the range of 10 to 50 mol %, even if the hydroxyl group-containing monomer is blended at the above-described proportion, solubility in the weak solvent can be ensured.

The carbon number of the branched alkyl group in the branched alkyl group-containing monomer is not particularly limited, as long as 3 or more carbon atoms are contained, and preferably 4 to 15, more preferably 4 to 10 are contained.

Examples of such branched alkyl group-containing monomers include vinyl ethers, or allylethers or (meth)acrylates containing a branched alkyl group. Examples of the branched alkyl group include an isopropyl group, isobutyl group, sec-butyl group, tert-butyl group, 2-ethylhexyl group, and 2-methylhexyl group. As the branched alkyl group-containing monomer, in view of excellent copolymerizability, vinyl ethers such as preferably, 2-ethylhexylvinyl ether (2-EHVE), and tert-butylvinyl ether are used, and more preferably, 2-HIVE is used. These branched alkyl group-containing monomer may be used singly or in a combination of two or more.

The double bond-containing monomer may contain, furthermore, other double bond-containing monomer other than the hydroxyl group-containing monomer and the branched alkyl group-containing monomer.

Examples of such other double bond-containing monomer is, preferably, a monomer containing an alkyl group, and examples of such alkyl groups include a straight chain, branched, or cyclic alkyl group. The alkyl group has carbon atoms of, for example, 2 to 8, preferably 2 to 6. In particular, when the double bond-containing monomer containing a cyclic alkyl group is blended, the glass transition temperature (Tg) of the fluorine-containing copolymer can be increased, and the coating hardness can further be increased.

Examples of such double bond-containing monomers containing a cyclic alkyl group include cyclic alkylvinylethers such as cyclohexylvinyl ether, and cyclohexylmethylvinyl ether; and (meth)acrylic acid cyclic alkyl esters such as cyclohexyl (meth)acrylate, and 3,3,5-trimethylcyclohexyl (meth)acrylate. These other double bond-containing monomers may be used singly or in a combination of two or more. The proportion of the other double bond-containing monomer relative to the total amount of the double bond-containing monomer is, preferably, 70 mol % or less, more preferably 30 to 60 mol %.

In the proportion of the polymerization unit based on the fluoroolefin relative to the polymerization unit of the double bond-containing monomer, the polymerization unit based on the fluoroolefin is preferably 30 to 70 mol %, more preferably 40 to 60 mol %, and the polymerization unit based on the double bond-containing monomer is preferably 70 to 30 mol %, more preferably 60 to 40 mol %. When the proportion of the polymerization unit based on the fluoroolefin is 70 mol % or less, solubility of the fluorine-containing copolymer in a weak solvent is sufficient, and when the proportion of the polymerization unit based on fluoroolefin is 30 mol % or more, sufficient weather resistance can be ensured. The fluorine-containing copolymer is preferably completely dissolved in the weak solvent in an amount blended in the coating composition, but it may be partially undissolved in the weak solvent.

Then, the fluorine-containing copolymer can be obtained by blending the fluoroolefin with a double bond-containing monomer containing a hydroxyl group-containing monomer and a branched alkyl group-containing monomer, and copolymerizing by adding a polymerization initiating source such as a polymerization initiator or an ionizing radiation in the presence of or in the absence of a polymerization medium. The copolymerization reaction is a known radical copolymerization reaction, and reactions conditions such as a reaction temperature, reaction time, and reaction pressure are suitably selected.

The fluorine-containing copolymer may further contain a carboxyl group. By containing a carboxyl group, for example, the pigment's dispersion improves when used as a coating. The fluorine-containing copolymer has a carboxyl group content relative to the fluorine-containing copolymer of for example, 1 to 5 mgKOH/g, preferably 2 to 5 mgKOH/g.

The carboxyl group can also be introduced, for example, by allowing the hydroxyl group of the fluorine-containing copolymer to react with polycarboxylic acid or its anhydride after polymerization reaction between fluoroolefin and the double bond-containing monomer. The carboxyl group can also be introduced by direct polymerization of the double bond-containing monomer having a carboxyl group.

The fluorine-containing copolymer contains 10 mass % or more, preferably 20 to 30 mass % of fluoroolefin-based fluorine relative to a total amount of the fluorine-containing copolymer. When the fluorine content is 10 mass % or more, weather resistance of the coating can be improved.

The fluorine-containing copolymer contains a hydroxyl group for allowing reaction with the isocyanate group of the polyisocyanate component, and its hydroxyl group value (hereinafter referred to as OHV) is, for example, 30 to 55 mgKOH/g, preferably 35 to 50 mgKOH/g. When the OHV is 30 mgKOH/g or more, the coating hardness can be increased. When the OHV is 55 mgKOH/g or less, the fluorine-containing copolymer can be sufficiently dissolved in a weak solvent.

The vinyl monomer-modified polyol can be obtained by allowing the above-described high-molecular weight polyol to react with a vinyl monomer.

As the high-molecular weight polyol, preferably, a high-molecular weight polyol selected from polyetherpolyol, polyester polyol, and polycarbonate polyol.

Examples of vinyl monomers include the above-described alkyl (meth)acrylate, vinyl cyanide, and vinylidene cyanide. These vinyl monomers may be used singly or in a combination of two or more. Of these vinyl monomers, preferably, alkyl (meth)acrylate is used.

The vinyl monomer-modified polyol can be obtained by allowing these high-molecular weight polyols to react with vinyl monomers in the presence of for example, a radical polymerization initiator (e.g., persulfate, organic peroxide, azo compound, etc.).

These high-molecular weight polyols may be used singly or in a combination of two or more.

As the high-molecular weight polyol, preferably, polyester polyol, or acrylic polyol is used, more preferably, polyester polyol is used, even more preferably, plant derived polyester polyol is used.

Examples of the polyol component include, furthermore, a naturally derived polyol component, to be specific, saccharide.

Examples of the saccharide include monosaccharides such as dihydroxyacetone, glyceraldehyde, erythrulose, erythrose, threose, ribulose, xylulose, ribose, arabinose, xylose, lyxose, deoxyribose, psicose, fructose, sorbose, tagatose, allose, altrose, glucose, mannose, gulose, idose, galactose, talose, fucose, fuculose, rhamnose, sedoheptulose, and digitoxose; disaccharides such as sucrose, lactose, maltose, trehalose, isotrehalose, isosaccharose, turanose, cellobiose, palatinose, gentiobiose, melibiose, and sophorose; trisaccharides such as raffinose, melezitose, gentianose, planteose, maltotriose, cellobiose, manninotriose, and panose; tetrasaccharides such as acarbose, stachyose, cellotetraose, and scorodose; polysaccharides such as glycogen, starch, amylose, amylopectin, cellulose, dextrin, dextran, glucan, fructose, N-acetylglucosamine, chitin, chitosan, charonin, laminaran, inulin, levan, ivory nut mannan, xylan, actinospectinoic acid, alginic acid, guaran, mannan, heparin, chondroitin sulfuric acid, hyaluronic acid, and pullulan; sugar alcohol such as erythritol, erythritol, maltitol, and sucrose; and oligosaccharides such as cyclodextrin. Examples of the sugar alcohol include the above-described glycerin, the above-described sorbitol, the above-described xylitol, the above-described mannitol, and the above-described mannite.

These saccharides may be used singly or in a combination of two or more.

These polyol components may be used singly or in a combination of two or more.

Examples of polyamine components include aromatic polyamine, aralkyl polyamine, alicyclic polyamine, aliphatic polyamine, amino alcohol, an alkoxysilyl compound having a primary amino group, or a primary amino group and a secondary amino group, and polyoxyethylene group-containing polyamine.

Examples of aromatic polyamines include 4,4'-diphenylmethanediamine, and tolylenediamine.

Examples of aralkyl polyamine include 1,3- or 1,4-xylylene diamine and mixtures thereof.

Examples of alicyclic polyamines include 3-aminomethyl-3,5,5-trimethylcyclohexylamine (also called: isophoronediamine), 4,4'-dicyclohexylmethanediamine, 2,5(2,6)-bis(aminomethyl) bicyclo[2.2.1]heptane, 1,4-cyclohexanediamine, 1-amino-3-aminomethyl-3,5,5-trimethylcyclohexane, bis-(4-aminocyclohexyl) methane, diaminocyclohexane, 3,9-bis-aminopropyl)-2,4,8,10-tetraoxaspiro[5.5]undecane, 1,3- and 1,4-bis(aminomethyl)cyclohexane and mixtures thereof.

Examples of the aliphatic polyamine include ethylenediamine, propylene diamine, 1,3-trimethylenediamine, 1,4-tetramethylenediamine, 1,5-pentamethylenediamine (including the above-described pentamethylenediamine), 1,6-hexamethylenediamine, hydrazine (including hydrate), diethylenetriamine, triethylenetetramine, tetraethylenepentamine, 1,2-diaminoethane, 1,2-diaminopropan and 1,3-diaminopentane.

Examples of aminoalcohol include N-(2-aminoethyl)ethanolamine.

Examples of alkoxysilyl compound having a primary amino group, or a primary amino group and a secondary amino group include alkoxysilyl group-containing monoamine such as Γ-aminopropyltriethoxysilane, and N-phenyl-γ-aminopropyltrimethoxysilane; N-β (aminoethyl) γ-aminopropyltrimethoxysilane; and N-β (aminoethyl) γ-aminopropylmethyldimethoxysilane.

Examples of polyoxyethylene group-containing polyamines include polyoxyalkylene ether diamine such as polyoxyethylene ether diamine. To be more specific, examples thereof include PEG#1000 diamine manufactured by NOF Corporation, Jeffamine ED-2003, EDR-148, and XTJ-512 manufactured by Huntsman Inc.

These polyamine components may be used singly or in a combination of two or more.

Examples of the active hydrogen compound include, furthermore, naturally-derived hydroxyl group-amino group-containing component, to be specific, amino acid.

Examples of amino acids include alanine, arginine, asparagine, aspartic acid, cystein, cystine, methionine, glutamine, glutamic acid, glycin, histidine, isoleucine, leucine, lysine, hydroxylysine, phenylalanine, proline, serine, threonin, tryptophan, proline, oxyproline, hydroxyproline, tyrosine, valine, glucosamine, monatin, taurine, β-alanine, β-aminopropionic acid, γ-aminobutyric acid, anthranilic acid, aminobenzoic acid, thyroxine, phosphoserine, desmosine, ornithine, creatine, and theanine.

These hydroxyl group-amino group-containing components may be used singly or in a combination of two or more. The hydroxyl group-amino group-containing component can also be used, for example, for adjusting the molecular weight of polyurethane resin.

Examples of the active hydrogen compound also include, in addition to the above-described ones, phenol resins typically represented by novolak and cresol phenol resins; polyphenols; polylactic acid, polyglycolic acid, and lactic acid, and a glycolic acid copolymer.

Examples of the active hydrogen compound further include, as a naturally derived active hydrogen compound component, urushiol, curcumine, lignin, cardanol, cardol, 2-methylcardol, 5-hydroxymethylfurfural, resorcinol, catechol, pyrogallol, terpene, laccol, thitsiol, phenol, naphthol, acetyl-CoA (acetyl coenzyme A), acetoacetyl-CoA (acetoacetyl coenzyme A), D-(−)-3-hydroxybutyryl-CoA, succinyl-CoA, (R)-3-hydroxybutyrate, isoeugenol, polybutylene succinate adipate, polyhydroxybutyrate, sophorolipid, and emulsan.

Examples of the naturally derived active hydrogen compound also include acids such as fatty acids.

Examples of the fatty acids include sebacic acid, azelaic acid, fumaric acid, succinic acid, oxalacetic acid, itaconic acid, mesaconic acid, citraconic acid, malic acid, citric acid, isocitric acid, gluconic acid, gallic acid, tartaric acid, malic acid, undecylenic acid, 11-aminoundecanoic acid, hepthylic acid, 12-hydroxystearic acid, 12-hydroxydodecanoic acid, linolenic acid, linoleic acid, ricinoleic acid, oleic acid, crotonic acid, myristoleic acid, palmitoleic acid, elaidic acid, vaccenic acid, gadoleic acid, eicosene acid, erucic acid, nervonic acid, 3-hydroxybutyric acid, levulinic acid, abietic acid, neoabietic acid, palustric acid, pimaric acid, isopimaric acid, dehydroabietic acid, anacardic acid, palmitic acid, 3-hydroxypropionic acid, 3-hydroxyhexanoic acid, 3-hydroxyvaleric acid, 3-hydroxybutanoic acid, 4-hydroxybutanoic acid, pyruvic acid, phosphoenolpyruvic acid, glyoxalic acid, oxoglutaric acid, dihydroxyacetonephosphoric acid, and spiculisporic acid.

Examples of the active hydrogen compound further include, when the molecular weight of the polyurethane resin is to be adjusted, monol and/or monoamine can also be used in combination.

Examples of the monol include methanol, ethanol, propanol, isopropanol, butanol, 2-ethylhexylalcohol, other alkanols (C5 to 38), and aliphatic unsaturated alcohols (C9 to 24), alkenylalcohol, 2-propene-1-ol, alkadienols (C6 to 8), and 3,7-dimethyl-1,6-octadiene-3-ol.

These monols may be used singly or in a combination of one or more.

Examples of the monoamine include dimethylamine, diethylamine, di-n-propylamine, diisopropylamine, di-n-butylamine, diisobutylamine, di-t-butylamine, dihexylamine, 2-ethylhexylamine, 3-methoxypropylamine, 3-ethoxypropylamine, 3-(2-ethylhexyloxypropylamine), 3-(dodecyloxy) propylamine, and morpholine.

These monoamines may be used singly or in a combination of two or more.

These active hydrogen compounds may be used singly or in a combination of two or more.

In the present invention, as necessary, known additives, for example, silane coupling agents, plasticizers, antiblocking agents, heat-resistant stabilizers, light-resistant stabilizer, antioxidants, release agents, catalysts, as well as pigments, dyes, lubricants, fillers, and hydrolysis inhibitor may be added. These additives may be added at the time of synthesizing components, or may be added at the time of mixing and dissolving components, or may be added after the synthesis.

The silane coupling agent that may be used is represented, for example, by the structural formula: $R-Si\equiv(X)_3$ or $R-S\equiv(R')(X)_2$ (wherein R represents an organic group having a vinyl, epoxy, amino, imino, isocyanate, or mercapto group; R' represents a lower alkyl group; and X represents a methoxy or ethoxy group, or chlorine atom.)

Specific examples of the silane coupling agent include chlorosilanes such as vinyl trichlorosilane; aminosilanes such as N-β-(aminoethyl)-γ-aminopropyltrimethoxysilane, γ-aminopropyltriethoxysilane, N-β-(aminoethyl)-γ-propylmethyldimethoxysilane, n-(dimethoxymethylsilylpropyl)ethylenediamine, n-(triethoxysilylpropyl)ethylenediamine, and N-phenyl-γ-aminopropyl trimethoxysilane; epoxysilanes such as γ-glycidoxypropyltrimetoxysilane, γ-glycidoxypropyltriethoxysilane, β-(3,4-epoxycyclohexyl)ethyltrimethoxysilane, and di(γ-glycidoxypropyl)dimethoxysilane; vinyl silanes such as vinyltriethoxysilane; and isocyanate silanes such as 3-isocyanatopropyltrimethoxysilane and 3-isocyanatepropyltriethoxysilane.

The silane coupling agents may be used singly or in a combination of two or more. The mixing ratio of the silane coupling agent is, for example, relative to 100 parts by mass of the polyisocyanate component (pentamethylene diisocyanate and/or polyisocyanate composition) and the active hydrogen compound, 0.001 to 10 parts by mass, preferably, 0.01 to 6 parts by mass.

The polyurethane resin of the present invention can be produced, for example, by polymerization methods such as bulk polymerization and solution polymerization.

In bulk polymerization, for example, under a nitrogen stream, while stirring pentamethylene diisocyanate and/or polyisocyanate composition, an active hydrogen compound is added thereto, and the mixture is allowed to react at a reaction temperature of 50 to 250° C., more preferably at 50 to 200° C., for about 0.5 to 15 hours.

In solution polymerization, pentamethylene diisocyanate and/or polyisocyanate composition, and an active hydrogen compound are added to an organic solvent, and the mixture is allowed to react at a reaction temperature of 50 to 120° C., more preferably at 50 to 100° C., for about 0.5 to 15 hours.

Examples of organic solvents include ketones such as acetone, methyl ethyl ketone, methylisobutylketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethylether acetate, propylene glycol methylether acetate, 3-methyl-3-methoxybutyl acetate, and ethyl-3-ethoxypropionate; ethers such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotic solvents such as N-methylpyrrolidone, dimethylformamide, N,N'-dimethylacetamide, dimethyl sulfoxide, and hexamethyl phosphoramide.

Examples of organic solvents also include nonpolar solvents (nonpolar organic solvents), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetal oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.), Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also turpentine oils such as methylcyclohexane (aniline point 40° C.), ethylcyclohexane (aniline point 44° C.), and gum turpentine N (manufactured by YASUHARA CHEMICAL CO., LTD., aniline point 27° C.).

Furthermore, in the above-described polymerization reaction, as necessary, for example, a urethanizing catalyst can be added.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organic metal compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as octenate copper; organic bismuth compounds such as bismuth octylate and bismuth neodecanoate.

Examples of urethanizing catalysts also include potassium salts such as potassium carbonate, potassium acetate, and potassium octoate.

These urethanizing catalysts may be used singly or in a combination of two or more.

In the above-described polymerization reaction, an (unreacted) pentamethylene diisocyanate and/or polyisocyanate composition can be removed, for example, by known removing methods such as distillation and extraction.

In bulk polymerization and solution polymerization, for example, pentamethylene diisocyanate and/or a polyisocyanate composition, and an active hydrogen compound are blended so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.6 to 2.5, preferably 0.75 to 1.3, more preferably 0.9 to 1.1.

When the above-described polymerization reaction is to be conducted more industrially, the polyurethane resin can be obtained by known methods such as, for example, one-shot method and prepolymer method according to its application.

In one-shot method, for example, pentamethylene diisocyanate and/or a polyisocyanate composition, and an active hydrogen compound are formulated (mixed) so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.6 to 2.5, preferably 0.75 to 1.3, more preferably 0.9 to 1.1, and then thereafter, the mixture is allowed to react (curing reaction), for example, at room temperature to 250° C., preferably at room temperature to 200° C., for, for example, 5 minutes to 72 hours, preferably 4 to 24 hours. The curing temperature may be a constant temperature, or may be increased/decreased stepwise.

In prepolymer method, for example, first, pentamethylene diisocyanate and/or a polyisocyanate composition, and a portion of an active hydrogen compound (preferably, high-molecular weight polyol) are allowed to react, thereby synthesizing an isocyanate group-terminated prepolymer having isocyanate groups at its molecular terminals. Then, the obtained isocyanate group-terminated prepolymer is allowed to react with the remaining portion of the active hydrogen compound (preferably, low-molecular-weight polyol and/or polyamine component), thereby causing curing reaction. In the prepolymer method, the remaining portion of the active hydrogen compound is used as a chain extender.

To synthesize the isocyanate group-terminated prepolymer, pentamethylene diisocyanate and/or polyisocyanate composition, and a portion of the active hydrogen compound are formulated (mixed) so that the equivalent ratio (NCO/active hydrogen group) of the isocyanate group in the pentamethylene diisocyanate and/or polyisocyanate composition relative to the active hydrogen group in the portion of the active hydrogen compound is for example, 1.1 to 20, preferably 1.3 to 10, more preferably 1.3 to 6, and then the mixture is allowed to react in the reaction vessel, for example, at room temperature to 150° C., preferably at 50 to 120° C., for, for example, 0.5 to 18 hours, preferably 2 to 10 hours. In this reaction, as necessary, the above-described urethanizing catalyst may be added, and after the completion of reaction, as necessary, the unreacted pentamethylene diisocyanate and/or polyisocyanate composition can be removed, for example, by a known removal method such as distillation or extraction.

Then, to cause the reaction between the obtained isocyanate group-terminated prepolymer and the remaining portion of the active hydrogen compound, the isocyanate group-terminated prepolymer and the remaining portion of the active hydrogen compound are formulated (mixed) so that the equivalent ratio (NCO/active hydrogen group) of the isocyanate group in the isocyanate group-terminated prepolymer relative to the active hydrogen group in the remaining portion of the active hydrogen compound is, for example, 0.6 to 2.5, preferably 0.75 to 1.3 and more preferably 0.9 to 1.1, and the mixture is allowed to react (curing reaction), for example, at room temperature to 250° C., preferably at room temperature to 200° C., for, for example, 5 minutes to 72 hours, preferably 1 to 24 hours.

The production method of the polyurethane resin is not limited to the above-described ones, and the polyurethane resin can be produced by other methods, as, for example, a coating material, adhesive, sealant, elastomer, or soft, hard, semi-hard foam. To be specific, the polyurethane resin can be produced, for example, in the form of a polyurethane solution that can be suitably used as a laminating adhesive, a aqueous polyurethane dispersion (PUD), low hardness elastomers such as a thermosetting elastomer, and a thermoplastic elastomer, and furthermore, elastic fiber and leather materials.

To be more specific, for example, the polyurethane resin can be obtained as an adhesive, by blending a polyisocyanate component (pentamethylene diisocyanate and/or polyisocyanate composition) and an active hydrogen compound.

In this case, the mixing ratio of the polyisocyanate component to the active hydrogen compound is adjusted such that the equivalent ratio (NCO/active hydrogen group) of the isocyanate group in the polyisocyanate component relative to the active hydrogen group of the active hydrogen compound is, for example, 0.4 to 10, preferably 0.5 to 5.

Stabilizers such as epoxy resin, curing catalyst, coating improving agent, leveling agent, antifoaming agent, antioxidant, and ultraviolet absorber, and additives such as plasticizer, surfactant, pigment, filler, organic or inorganic microparticles, antifungal agent, and a silane coupling agent can be added, as necessary, to one or both of the polyisocyanate component and the active hydrogen compound. The mixing ratio of these additives are suitably decided based on the purposes and use.

Such an adhesive is used, for example, lamination of composite films, to be specific, used for adhesion between films of a composite film.

That is, in lamination, for example, the following methods are used. A polyisocyanate component and an active hydrogen compound are blended by being diluted with a known organic solvent to prepare a laminating adhesive, and then the adhesive is applied on the surfaces of the films by a solvent type laminator. After the solvent is volatilized, the surfaces to which the adhesive was applied were bonded together, and thereafter, the adhesive was matured to be cured at normal temperature or while heated. In another method, for example, when the viscosity of the blended polyisocyanate component and active hydrogen compound is about 100 to 10000 mPa·s, preferably about 100 to 5000 mPa·s at normal temperature to 100° C., for example, the polyisocyanate component and the active hydrogen compound are blended as is to prepare a laminating adhesive, and then thereafter the adhesive is applied on the surfaces of the films by a solventless type laminator, and the surfaces to which the adhesive are applied are bonded together, and thereafter, the adhesive was matured to be cured at normal temperature or while heated.

Generally, the application amount is, for example, when the adhesive is a solvent type, based on the grammage (solid content) after volatilizing the solvent, about 2.0 to 5.0 g/m$^2$, and when the adhesive is a solventless type, about 1.0 to 3.0 g/m$^2$.

The films to be bonded are not particularly limited, as long as the film can be laminating processed into a composite film, and examples thereof include metal foil and plastic film.

Examples of metals for the metal foil include aluminum, stainless steel, iron, copper, and lead. The metal foil has a thickness of, generally, 5 to 100 μm, preferably 7 to 50 μm.

Examples of plastic for the plastic film include olefinic polymer (e.g., polyethylene, polypropylene, polystyrene, etc.), acrylic polymer (e.g., polymethylmethacrylate, polyacrylonitrile, ethylene-methacrylic acid copolymer, and ionomer resin in which molecules of an ethylene-methacrylic acid copolymer are crosslinked with a metal ion, etc.), polyester polymer (e.g., polyalkylene terephthalate such as polyethyleneterephthalate (PET) and polybutyleneterephthalate, polyalkylene naphthalate, and copolyester mainly composed of their polyalkylene arylate unit, etc.), polyamide polymer (e.g., nylon 6, nylon 66, polym-phenyleneisophthalamide, polyp-phenyleneterephthalamide, etc.), vinyl polymer (e.g., polyvinyl chloride, ethylene-vinyl acetate copolymer, ethylene-vinylalcohol copolymer, etc.), fluorine polymer (e.g., polytetrafluoroethylene, etc.), and also polyoxymethylene, polycarbonate, polyphenylene oxide, and polyesterurethane.

On the plastic film, an inorganic layer can be formed on at least one of its surfaces. The inorganic layer can be formed, for example, by vapor deposition, sputtering, or sol-gel method. Examples of the inorganic substance that forms inorganic layer include simple substances such as titanium, aluminum, and silicon, and an inorganic compound (oxide, etc.) containing these elements. To be specific, examples thereof include an alumina deposited film and a silica deposited film.

The plastic film has a thickness of generally, 5 to 200 μm, preferably 10 to 150 μm.

The surfaces of the metal foil and the plastic film can also be subjected to surface treatments such as a corona discharge treatment, and a primer treatment using an anchor coating material. The metal foil and the plastic film can also be printed suitably.

The composite film formed by applying an adhesive between the films has an adhesive strength of for example, 5.0N/15 mm or more, preferably 6.0N/15 mm or more, more preferably 8.0N/15 mm or more, and generally 15.0N/15 mm or less, the adhesive strength being measured after heat sealing the end of the composite film, filling the film with a mixture of, for example, water, fatty acid, natural oil, and an organic solvent as contents, and then subjecting the film to boiling water sterilization at 100° C. for 30 minutes.

The pentamethylene diisocyanate and/or polyisocyanate composition, and/or polyurethane resin of the present invention can be used as an adhesive and/or a coating material for one or both surfaces of a protection sheet for solar cell modules.

These adhesives and coating materials are excellent in adhesiveness with base material films, and also exhibit higher water vapor barrier properties, weather resistance, solvent resistance, and durability.

A coating material for protection sheets for solar cell modules can be obtained by allowing a polyisocyanate component (pentamethylene diisocyanate and/or a polyisocyanate composition), and an active hydrogen compound. These coating materials for protection sheets for solar cell modules modifies the surface of the base material film, and impart water and oil repellency, and antifouling properties.

The polyisocyanate component can be used as a blocked isocyanate, in which free isocyanate groups contained in the molecule is blocked by a blocker.

Examples of the active hydrogen compound include polycarbonate polyol, epoxy polyol, polyolefin polyol, acrylic polyol, and fluorine polyol, and preferably, polycarbonate polyol, acrylic polyol, or fluorine polyol is used.

These active hydrogen compounds may be used singly, or may be used in a combination of two or more.

The coating material for protection sheets for solar cell modules can be applied on a base material film by a known method. Usually, the coating material for protection sheets for solar cell modules are dispersed in an organic solvent or water to be diluted, and then allowed to attach on the surface of the base material film by a known method such as impregnation application, spray application, and foam application, and thereafter dried. Furthermore, a surface treatment agent (e.g., water repellent and oil repellent), insect repellent, softener, antibacterial agent, fire retardant, antistatic agent, coating fixer, or antiwrinkle agent may be used singly, or may be used in combination.

To obtain a polyurethane resin as an aqueous polyurethane dispersion, for example, first, pentamethylene diisocyanate and/or polyisocyanate composition is allowed to react with an active hydrogen compound including an active hydrogen compound containing a hydrophilic group (hereinafter abbreviated as a hydrophilic group-containing active hydrogen compound) to be described later, thereby producing an isocyanate group-terminated prepolymer.

Then, the produced isocyanate group-terminated prepolymer and a chain extender are allowed to react with each other to be dispersed in water. In this manner, an aqueous polyurethane resin in which chains of an isocyanate group-terminated prepolymer are extended by a chain extender can be obtained as an internally emulsified aqueous polyurethane dispersion.

To cause the isocyanate group-terminated prepolymer to react with the chain extender in water, for example, first, the isocyanate group-terminated prepolymer is added to water, thereby dispersing the isocyanate group-terminated prepolymer. Thereafter, a chain extender is added thereto, thereby causing chains of the isocyanate group-terminated prepolymer to extend.

The hydrophilic group-containing active hydrogen compound is a compound having both of a hydrophilic group and an active hydrogen group, and examples of hydrophilic groups include anionic groups (e.g., carboxyl group, etc.), cationic groups, and nonionic group (e.g., polyoxyethylene group, etc.). Examples of hydrophilic group-containing active hydrogen compounds include, to be more specific, carboxylic acid group-containing active hydrogen compounds, and polyoxyethylene group-containing active hydrogen compounds.

Examples of carboxylic acid group-containing active hydrogen compounds include dihydroxylcarboxylic acids such as 2,2-dimethylolacetic acid, 2,2-dimethylollactic acid, 2,2-dimethylol propionic acid, 2,2-dimethylolbutanoic acid, 2,2-dimethylolbutyric acid, and 2,2-dimethylolvaleric acid; diaminocarboxylic acids such as lysine, and arginine; metal salts thereof; and ammonium salts thereof.

The polyoxyethylene group-containing active hydrogen compound is a compound containing a polyoxyethylene group at its main chain or a side chain and having two or more active hydrogen groups, and examples thereof include polyethylene glycol, and polyoxyethylene side chain-containing polyol (a compound containing a polyoxyethylene group at its side chain, and having two or more active hydrogen groups).

These hydrophilic group-containing active hydrogen compounds may be used singly or in a combination of two or more.

As the chain extender, for example, low-molecular-weight polyols such as the above-described dihydric alcohol, and the above-described trihydric alcohol; and diamines such as alicyclic diamines and aliphatic diamines may be used.

These chain extenders may be used singly or in a combination of two or more.

When an active hydrogen compound containing a hydrophilic group-containing active hydrogen compound is used as described above, as necessary, the hydrophilic group is neutralized by a known neutralizing agent.

When the hydrophilic group-containing active hydrogen compound is not used as the active hydrogen compound, the polyurethane resin can be obtained as an externally emulsified aqueous polyurethane dispersion by emulsification, for example, using a known surfactant.

To obtain the polyurethane resin as a low hardness elastomer, a polyisocyanate component (pentamethylene diisocyanate and/or polyisocyanate composition) is mixed with an active hydrogen compound so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.2 to 1.0, preferably 0.3 to 0.7, more preferably 0.5 to 0.6, and then thereafter, the mixture is allowed to react (curing reaction), for example, at room temperature to 250° C., preferably room temperature to 200° C., for, for example, 1 min to 72 hours, preferably 4 to 24 hours. The curing temperature may be a constant temperature, or may be increased/decreased stepwise. In this reaction, as necessary, the above-described urethanizing catalyst may be added.

Examples of the active hydrogen compound include polyether polyol such as polyethylene glycol, polypropylene glycol, and polyethylene polypropylene glycol (including random and/or block copolymer of two types of alkylene oxides) obtained by addition reaction of alkylene oxides such as ethylene oxide and/or propylene oxide, using a low-molecular-weight polyol or an aromatic/aliphatic polyamine as an initiator. Furthermore, for example, polytetramethylene ether glycol obtained by ring-opening polymerization of tetrahydrofuran, to be specific, for example, PTXG (manufactured by Asahi Kasei Fibers Corporation. Hereinafter referred to as PTXG) in which neopentyl glycol is copolymerized with tetrahydrofuran, and PTG-L (manufactured by Hodogaya Chemical Co., LTD. hereinafter referred to as PTG-L) in which 3-methyltetrahydrofuran is copolymerized with tetrahydrofuran. Preferably, polyoxypropylene glycol produced by addition polymerization of propylene oxide with dipropylene glycol using a phosphazenium compound as a catalyst according to the method described in Example 2 of Japanese Patent 3905638, and/or PTXG, and/or PTG-L are suitably used.

The thus obtained low hardness elastomer has a hardness measured by type C hardness test (hereinafter may be referred to as hardness) of, for example, 0 to 50, preferably 0 to 40, more preferably 0 to 25; a total luminous transmittance of, for example, 90% or more, preferably 92% or more, more preferably 93% or more, and usually 99% or less; and a haze of for example, 40% or less, preferably 30% or less, more preferably 10% or less, and usually 1% or more.

The thus obtained low hardness elastomer has a tensile strength of, for example, 0.2 MPa or more, preferably 0.5 MPa or more, more preferably 0.7 MPa or more; an elongation at break of for example, 300% or more, preferably 600% or more, more preferably 800% or more; a tear strength of, for example, 1.5 kN/m or more, preferably 2.0 kN/m or more; and a compression set of when measured at 23° C., 1.5% or less, preferably 0.8% or less, usually 0.1% or more, and when measured at 70° C., for example, 2.0% or less, preferably 1.2% or less, and usually 0.1% or more.

Such a low hardness elastomer is non-yellowing, and even if adjusted to give a super low hardness, is less tacky; has excellent transparency, tear strength, tensile strength, elongation at break, and heat resistance (softening temperature); and furthermore, has a low compression set. Furthermore, such a low hardness elastomer is less tacky, and therefore after it is thermally cured, demolding is easy, leading to excellent productivity. Furthermore, such a low hardness elastomer can be applied, because of its excellent non-yellowing and transparency, for example, for a sealant for high brightness LEDs; and because of its soft touch and elasticity, for example, sporting goods, leisure products, medical products, nursing care goods, housing materials, acoustic material, sealing material, packing, vibration proofing and damping/base isolation members, sound insulation material, daily use articles, miscellaneous goods, automotive products, optical components, members for OA devices, surface protection member for goods, semiconductor sealing material, and self-repair coating material.

Furthermore, such a low hardness elastomer can be used as a flexible electrode material, by adding, for example, 0.001 to 60 mass %, preferably 0.01 to 50 mass %, more preferably 0.1 to 40 mass % of a conductive material such as piezoelectric ceramic, titanium dioxide, barium titanate, quartz, lead titanate-zirconium, carbon black, graphite, single-layer or multilayer carbon nanotube, phthalocyanine, polythiophene, polyaniline, and polypyrrole. Particularly, with its piezoelectric properties and electromechanical transducing properties, such a low hardness elastomer can be used as various operation device, sensor, generator, artificial muscle, and an actuator.

The thus obtained polyisocyanate composition obtained by using pentamethylene diisocyanate of the present invention is excellent in storage stability, and a polyurethane resin obtained by using the pentamethylene diisocyanate or polyisocyanate composition is excellent in various physical properties.

Therefore, such a polyurethane resin can be used widely in various industrial fields.

Pentamethylenediamine or its salt obtained by such a method can be suitably used, for example, as a material for production (monomer material for polymerization) of, for example, polyimide, polyimide, and polyamide-imide, and as a curing agent such as polyurethane, and an epoxy resin.

Pentamethylene diisocyanate and/or its derivative used in such a method can be suitably used as, for example, a material for carbodiimide derivative, uretone imine derivative, uretdione derivative, urea derivative, biuret derivative, and allophanate derivatives.

Furthermore, by using the pentamethylene diisocyanate and/or its derivative in production of, for example, coating, overprint varnish (OP varnish), industrial or packaging use adhesive, thermoplastic and thermosetting or millable elastomer, sealant, aqueous resin, thermosetting resin, binder resin (to be specific, a binder resin used for various materials such as rubber chip, granular natural stone, paper, woods, various plastic chips, various metals, toner, and magnetic record material in use for ink, screen printing, and concrete), resin for lens, activation energy setting resin, liquid crystal resin, flexible foam, and rigid foam, their heat resistance, water resistance, chemical resistance, mechanical properties, and electrical properties can be improved.

Furthermore, such pentamethylene diisocyanate and/or its derivative, and pentamethylenediamine or its salt can be used, for example, as the above-described active hydrogen group-containing compound component, in particular, as cross-linking agents and modifiers such as the above-described naturally-derived saccharide, amino acid, and fatty acid.

The above-described pentamethylene diisocyanate can also be allowed to react with polyamine to produce polyurea resin.

Examples of polyamine include, for example, the above-described polyamine component, preferably, aliphatic polyamine, alicyclic polyamine, and in view of polyurea resin's transparency and non-yellowing characteristics, more preferably, aliphatic diamine having about 3 to 20 carbons, isophorone diamine, 4,4'-dicyclohexylmethanediamine, 2,5 (2,6)-bis(aminomethyl) bicyclo[2.2.1]heptane, 1,3- and 1,4-bis(aminomethyl)cyclohexane, and alicyclic diamine of a mixture of these.

In view of polyurea resin's piezoelectricity, particularly preferably, the above-described pentamethylenediamine (pentamethylenediamine used for production of pentamethylene diisocyanate of the present invention).

Such a polyurea resin can be produced, for example, as described in Japanese Unexamined Patent Publication No. H2-284485, by a method in which diamine and diisocyanate are evaporated in vacuum, and they are subjected to vapor deposition polymerization on the substrate; or a method in which diisocyanate or polyamine is allowed to react in a solvent, coating is performed, and subjected to polymerization reaction.

Examples of the solvent include N,N'-dimethylformamide, N,N'-dimethylacetamide, tetrahydrofuran, acetone, methyl ethyl ketone, ethyl acetate, butyl acetate, chloroform, toluene, and xylene.

The reaction temperature of pentamethylene diisocyanate and polyamine is, although it depends on chemical properties of the polyamine used, for example, 10 to 200° C., preferably 30 to 150° C., more preferably 40 to 130° C.

The pressure in the case of vapor deposition polymerization is preferably a pressure that allows pentamethylene diisocyanate and polyamine to evaporate, for example, 1 to 100 Pa, more preferably about 10 to 80 Pa. When using the coating reaction method, in view of productivity, it is preferable to conduct polymerization reaction under normal pressure.

The thus obtained polyurea resin can be used, for example, as, in addition to a coating material, an adhesive, a waterproofing material, a film, and a sheet, for speakers and sensors, and furthermore, piezoelectric material or pyroelectric material that can be used for converting heat and mechanical stimuli to electric energy.

To be more specific, such a polyurea resin can be used, for example, as organic piezoelectric and pyroelectric material, in acoustic materials in the fields of diaphragms such as microphones, and speakers, measuring devices such as ultrasonic sensor, various heat and pressure sensors, and infrared detectors, ultrasonic probe, vibration sensor that detects mutation of genes and proteins highly sensitively.

EXAMPLES

In the following, the present invention will be described in more detail with reference to Examples and Comparative Examples, but the present invention is not limited thereto. In the description below, "parts" and "%" are mass-based unless otherwise specified. The measurement methods used in Production Examples are described below.

<Reaction Yield of Pentamethylenediamine (Unit: Mol %)>

Using L-lysine monohydrochloride (manufactured by Wako Pure Chemical Industries, Ltd.), and purified pentamethylenediamine obtained in (Distillation of Pentamethylenediamine) to be described later, the pentamethylenediamine concentration was calculated based on the calibration curve made from the area value of the chromatogram obtained under the HPLC (high-performance liquid chromatograph) analysis conditions below, and the ratio of the pentamethylenediamine concentration relative to the total concentration of L-lysine monohydrochloride and pentamethylenediamine was regarded as reaction yield of pentamethylenediamine.
Column; Asahipak ODP-50 4E (manufactured by Showa Denko K.K.)
Column Temperature; 40° C.
Eluent; 0.2 mol/L sodium phosphate (pH7.7)+2.3 mmol/L sodium 1-octanesulfonate
Flow Rate; 0.5 mL/min
For detection of L-lysine monohydrochloride and pentamethylenediamine, postcolumn derivatization [J. Chromatogr., 83, 353-355 (1973)] using o-phthalaldehyde is used.

<Purity of Pentamethylenediamine (Unit: Mass %)>

Using the purified pentamethylenediamine obtained in (Distillation of Pentamethylenediamine) to be described later, pentamethylenediamine purity was calculated based on the calibration curve made from the area value of the chromatogram obtained under the gas chromatograph (GC) analysis conditions below.
Apparatus; GC-6890 (manufactured by Agilent)
Column; WCOT FUSED SILICA CP-SIL 8CB FOR AMINES (manufactured by VARIAN)
Oven temperature; held at 40° C. for 3 minutes, temperature increased at 10° C./min from 40° C. to 300° C., and held at 300° C. for 11 minutes
Injection Temperature; 250° C.
Detector temperature; 280° C.
Carrier Gas; helium
Detection Method; FID <Extraction Rate (Unit: Mass %)>

To obtain extraction rate of pentamethylenediamine using an extractant, the above-described measurement (Purity of Pentamethylenediamine) was conducted, and the pentamethylenediamine concentration in the aqueous solution of pentamethylenediamine before the extraction operation, and the pentamethylenediamine concentration in the extractant after the extraction operation were measured.

Then, the extraction rate was calculated based on the following formula.

(a) mass of pentamethylenediamine in extractant=pentamethylenediamine concentration in extractant×mass of extractant/100

(b) mass of pentamethylenediamine in charged aqueous solution of pentamethylenediamine=diaminopentane concentration in aqueous solution of pentamethylenediamine before extraction operation×mass of charged aqueous solution of pentamethylenediamine/100 extraction rate (mass %)=$(a)/(b)\times 100$

<Total Amount Contained of Compound Having Cyclic Structure Having C=N Bond (Unit: Mass %)>

The total amount contained of a compound having a cyclic structure having C=N bond was obtained from a total value of (2,3,4,5-tetrahydropyridine concentration) and (2-(aminomethyl)-3,4,5,6-tetrahydropyridine concentration) to be described later.

<2,3,4,5-Tetrahydropyridine Concentration (Unit: Mass %)>

2,3,4,5-tetrahydropyridine concentration was calculated using 2,3,4,5-tetrahydropyridine obtained in (Structure Analysis of Unknown Substance) to be described later based on the calibration curve made from the area value of the gas chromatogram obtained by measurement under the same conditions described in (Purity of Pentamethylenediamine).

<2-(Aminomethyl)-3,4,5,6-Tetrahydropyridine Concentration (Unit: Mass %)>

2-(aminomethyl)-3,4,5,6-tetrahydropyridine concentration was calculated using 2-(aminomethyl)-3,4,5,6-tetrahydropyridine obtained in (Structure Analysis of Unknown Substance) to be described later based on the calibration curve made from the area value of the gas chromatogram obtained by measurement under the same conditions described in (Purity of Pentamethylenediamine).

<Purity of Pentamethylene Diisocyanate (Unit: Mass %)>

The purity of pentamethylene diisocyanate was measured by a method of [1] or [2] below.

[1] Using pentamethylene diisocyanate (a) obtained in Example 1 to be described later, a calibration curve was made from the area value of the chromatogram obtained under the GC analysis conditions below, and the purity of pentamethylene diisocyanate was calculated.
Apparatus; GC-6890 (manufactured by Agilent)
Column; UADX-30 (manufactured by Frontier Laboratories Ltd.) 0.25 mmϕ×30 in, film thickness 0.15 μm
Oven Temperature; held at 50° C. for 5 minutes, the temperature increased at a rate of 10° C./min from 50° C. to 200° C., and the temperature increased at a rate of 20° C./min from 200° C. to 350° C., and held at 350° C. for 7.5 minutes
Injection Temperature: 250° C.
Detector temperature; 250° C.
He Flow Rate; 1.2 mL/min
Injection Mode; Split
Detection Method; FID

[2] Using a potential difference titrator, purity of pentamethylene diisocyanate was calculated from the isocyanate group concentration measured by n-dibutylamine method in conformity with JIS K-1556.

<Yield of Pentamethylene Diisocyanate in Heat Treatment (Unit: Mass %)>

The yield of pentamethylene diisocyanate in heat treatment was calculated from formulas below.

$(c)\times(d)/((a)\times(b))\times 100$ (a): parts by mass of pentamethylene diisocyanate before heat treatment
(b): purity of pentamethylene diisocyanate before heat treatment
(c): parts by mass of pentamethylene diisocyanate after heat treatment
(d): purity of pentamethylene diisocyanate after heat treatment <Hydrolyzable Chlorine Concentration (Unit: %)>

The hydrolyzable chlorine concentration (HC) of isocyanate was measured in conformity with hydrolyzable chlorine testing method of JIS K-1556 (2000), Annex 3.

<Total Amount of Compound Represented by Formula (1) and Compound Represented by Formula (2) Contained (Unit: ppm>

The total amount of the compound represented by the general formula (1) below, and the compound represented by the general formula (2) below contained was regarded as the area value of gas chromatogram obtained by the measurement under the same conditions for [1] of (purity of pentamethylene diisocyanate).

[Chemical Formula 6]

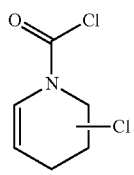

(1)

[Chemical Formula 7]

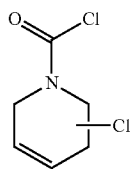

(2)

<Pentamethylenediisocyanate Concentration (Unit: Mass %)>

Using pentamethylene diisocyanate (a) obtained in Example 1 to be described later, the pentamethylene diisocyanate concentration in polyisocyanate composition was calculated based on the calibration curve made from the area value of chromatogram obtained under the HPLC analysis conditions below.
Apparatus; Prominence (manufactured by Shimadzu Corporation)
 1) Pump LC-20AT
 2) Degasser DGU-20A 3
 3) Autosampler SIL-20A
 4) Column constant temperature bath COT-20A
 5) Detector SPD-20A
Column; SHISEIDO SILICA SG-120
Column Temperature; 40° C.
Eluent; n-hexane/methanol/1,2-dichloroethane=90/5/5 (Volume Ratio)
Flow Rate; 0.2 mL/min
Detection method; UV 225 nm <Conversion Rate of Isocyanate Group (Unit: %)>

The conversion rate of isocyanate group is determined as follows: in the chromatogram obtained under the following GPC measurement conditions, the proportion of the peak area on the high-molecular weight-side than the peak of pentamethylene diisocyanate relative to the total peak area was regarded as the conversion rate of the isocyanate group.
Apparatus; HLC-8020 manufactured by Tosoh Corporation)
Column; G 1000HXL, G 2000HXL and G 3000HXL (all manufactured by TOSOH CORPORATION, trade names) are connected in series
Column Temperature; 40° C.
Eluent; tetrahydrofuran
Flow Rate; 0.8 mL/min
Detection method; differential refractive index
Standard Substance; polyethylene oxide (manufactured by Tosoh Corporation, trade name: TSK standard polyethylene oxide)<

Isocyanate Trimer Concentration (Unit: Mass %)>

The measurement described above of (conversion rate of isocyanate group) was conducted, and the peak area proportion corresponding to three times the molecular weight of pentamethylene diisocyanate was regarded as the isocyanate trimer concentration.

<Isocyanate Group Concentration (Unit: Mass %)>

The isocyanate group concentration of the polyisocyanate composition was measured by n-dibutylamine method in conformity with JIS K-1556 using a potential difference titrator.

<Viscosity (Unit: mPa·s)>

Using an E-type viscometer TV-30 manufactured by TOKI Sangyo Co., Ltd., the viscosity of the polyisocyanate composition at 25° C. was measured.

<Color (Unit: APHA)>

The color of the polyisocyanate composition was measured by the method in conformity with JIS K-0071.

(Distillation of Pentamethylenediamine)

A four-neck flask equipped with a thermometer, a distillation column, a condenser tube, and a nitrogen inlet tube was charged with pentamethylenediamine (manufactured by Tokyo Chemical Industry Co., Ltd.), and under conditions of a column top temperature of 111 to 115° C. and 10 KPa, the pentamethylenediamine was rectified while further being refluxed, thereby producing a purified pentamethylenediamine. The pentamethylenediamine subjected to the purification by distillation had an area proportion in gas chromatography of 100%.

Preparation Example 1

Preparation of Bacterial Cell-Disrupted Solution (Cloning of Lysine Decarboxylase Gene (cadA))

A genomic DNA prepared from *Escherichia coli* W 3110 strain (ATCC 27325) in accordance with a common procedure was used as a template for PCR.

As the primer for PCR, oligonucleotide (synthesized by Invitrogen Corporation by request) having a base sequence shown in sequence ID Nos. 1 and 2 designed based on the base sequence of lysine decarboxylase gene (cadA)(GenBank Accession No. AP 009048) was used. These primers have restriction enzyme recognition sequences of KpnI and XbaI in the proximity of 5'-end.

Using 25 µL of a PCR reaction liquid containing 1 ng/µL of the genomic DNA and 0.5 pmol/µL each of the primers, a PCR was conducted for 30 cycles under the following conditions: a reaction cycle of denaturation: 94° C. 30 seconds, annealing: 55° C. 30 minutes, and extension reaction: 68° C., 2 minutes.

PCR reaction product and plasmid pUC18 (manufactured by Takara Shuzo Co., Ltd.) were digested with KpnI and XbaI, and ligated using Ligation high (manufactured by TOYOBO CO., LTD.). Thereafter, using the obtained recombinant plasmid, *Escherichia coli* DH5α (manufactured by TOYOBO CO., LTD.) was transformed. The transformant was cultured in LB agar medium containing ampicillin (Am) 100 μg/mLb and X-Gal (5-bromo-4-chloro-3-indolyl-β-D-galactoside), thereby producing an Am-resistant, white colony transformant. The plasmid was extracted from the thus obtained transformant.

It was confirmed that the base sequence of the DNA fragment inserted into the plasmid was the base sequence shown in sequence ID No. 3 according to a common base sequence determination method.

The obtained plasmid having a DNA that codes lysine decarboxylase was named pCADA. By culturing *Escherichia coli* transformed using pCADA, lysine decarboxylase having amino acid sequence shown in sequence ID No. 4 could be produced.

(Production of Transformant)

*Escherichia coli* W 3110 strain was transformed by a usual method using pCADA, and the obtained transformant was named W/pCADA.

The transformant was inoculated into 500 ml of LB medium containing Am 100 μg/mL in a Erlenmeyer flask having a baffle, and cultured with shaking at 30° C. until OD (660 nm) reached 0.5; thereafter, IPTG (isopropyl-(3-thiogalactopyranoside) was added thereto so that the IPTG was 0.1 mmol/L therein, and shaking culture was conducted for further 14 hours. The culture solution was subjected to centrifugal separation at 8000 rpm for 20 min, thereby collecting bacterial cells. The bacterial cells were suspended in a 20 mmol/L sodium phosphate buffer solution (pH6.0), and subjected to ultrasonic disruption, thereby preparing a bacterial cell-disrupted solution.

Preparation Example 2

Production of Aqueous Solution of Pentamethylenediamine

To a flask, 120 parts by mass of a substrate solution was added: the substrate solution was prepared so that the final concentration of L-lysine monohydrochloride (manufactured by Wako Pure Chemical Industries, Ltd.) was 45 mass %, and the final concentration of pyridoxal phosphate (manufactured by Wako Pure Chemical Industries, Ltd.) was 0.15 mmol/L. Then, the above-described W/pCADA bacterial cell-disrupted solution (charged dry bacterial cell-based weight 0.3 g) were added, thereby allowing the reaction to start. The reaction conditions were as follows: 37° C. and 200 rpm. The pH of the reaction liquid was adjusted to pH6 with a 6 mol/L hydrochloric acid. The reaction yield of pentamethylenediamine after 24 hours reached 99%. The pH of the above-described reaction liquid after a reaction of 24 hours was adjusted to pH2 with a 6 mol/L hydrochloric acid, and 0.6 parts by mass of activated carbon (manufactured by Mikura Kasei Kabushiki Kaisha powder activated carbon PM-SX) was added thereto. The mixture was stirred at 25° C. for 1 hour, and filtered through a filter paper (manufactured by ADVANTEC, 5C). Then, the filtrate was adjusted to pH12 with sodium hydroxide, thereby producing an aqueous solution of pentamethylenediamine (17.0 mass % aqueous solution).

Production Example 1

Preparation of Pentamethylenediamine (a)

To a separatory funnel, 100 parts by mass of an aqueous solution of pentamethylenediamine and 100 parts by mass of n-butanol were charged, and the mixture was stirred for 10 minutes. Thereafter, the mixture was allowed to stand for 30 minutes. The lower layer, i.e., the aqueous layer, was discharged, and then the upper layer, i.e., the organic layer (n-butanol containing pentamethylenediamine), was discharged. The extraction rate measured was 91.6%. Then, a four-neck flask equipped with a thermometer, a distillation column, a condenser tube, and a nitrogen inlet tube was charged with 80 parts by mass of the extract of the organic layer, and with an oil bath temperature of 120° C. and under a reduced pressure of 10 kPa, n-butanol was distilled off. Then, the oil bath temperature was set to 140° C., and pentamethylenediamine was distilled off under a reduced pressure of 10 kPa, thereby producing pentamethylenediamine (a) having a purity of 99.9 mass %.

The obtained pentamethylenediamine (a) contained impurities including 2,3,4,5-tetrahydropyridine.

Production Example 2

Preparation of Pentamethylenediamine (b)

The solvent was extracted in the same manner as in Production Example 1 above except that 100 parts by mass of isobutanol was charged instead of 100 parts by mass of n-butanol. The extraction rate measured was 86.0%.

Then, isobutanol was distilled off in the same manner as in Production Example 1, thereby producing pentamethylenediamine (b) having a purity of 99.8 mass %.

The obtained pentamethylenediamine (b) contained impurities including 2,3,4,5-tetrahydropyridine.

Production Example 3

Preparation of Pentamethylenediamine (c)

A four-neck flask equipped with a mixer, a thermometer, a reflux pipe, and a nitrogen inlet tube was charged with 200 parts by mass of an aqueous solution of pentamethylenediamine obtained in Preparation Example 2, water was distilled off under 38 kPa, at 80° C., thereby producing 19.7 mass % of an aqueous solution of pentamethylenediamine.

A separatory funnel was charged with 100 parts by mass of the above-described aqueous solution of pentamethylenediamine and 100 parts by mass of n-butanol (extractant), and the mixture was stirred for 10 minutes. Thereafter, the mixture was allowed to stand for 30 minutes. Then, the organic layer was discharged, and the extraction rate was measured. As a result, the extraction rate was 93.5%.

Then, in the same manner as in Production Example 1, pentamethylenediamine (c) having a purity of 99.7 mass % was obtained.

The obtained pentamethylenediamine (c) contained impurities including 2,3,4,5-tetrahydropyridine.

Production Example 4

Preparation of Pentamethylenediamine (d)

To a separatory funnel, 100 parts by mass of an aqueous solution of pentamethylenediamine and 100 parts by mass of chloroform were charged, and the mixture was stirred for 10 minutes. Thereafter, the mixture was allowed to stand for 30 minutes. The lower layer, i.e., the aqueous layer, was discharged, and then the upper layer, i.e., the organic layer, was discharged. The extraction rate measured was 61.7%. Then, a four-neck flask equipped with a thermometer, a distillation column, a condenser tube, and a nitrogen inlet tube was charged with 80 parts by mass of the extract of the organic layer, and with an oil bath temperature of 120° C. and under a reduced pressure of 10 kPa, chloroform was distilled off, thereby producing pentamethylenediamine (d*). Then, the oil bath temperature was set to 140° C., and under a reduced pressure of 10 kPa, pentamethylenediamine was distilled off, thereby producing pentamethylenediamine (d) having a purity of 99.2 mass %.

The obtained pentamethylenediamine (d) contained impurities including 2,3,4,5-tetrahydropyridine and unknown substance.

Testing Example 1

Structure Analysis of Unknown Substance Contained in Pentamethylenediamine

Using a solid phase extraction cartridge (manufactured by VARIAN, Model 1225-6067), impurities contained in pentamethylenediamine were fractionated, and structural analysis was performed by GC-MS analysis and NMR analysis.

For conditioning the solid phase extraction cartridge, a solution mixture of 50 mL of methanol and 450 mL of chloroform were passed through. After dissolving 500 mg of pentamethylenediamine (d*) in the solution mixture of 50 mL of methanol and 450 mL of chloroform, the mixture was passed through the solid phase extraction cartridge, and effluent was obtained. Then, a solution mixture of methanol and chloroform having the proportion below was passed through to a total of five times, and the effluent from the solid phase extraction cartridge was fractionated.

First; solution mixture of 100 mL of methanol and 900 mL of chloroform
Second; solution mixture of 50 mL of methanol and 450 mL of chloroform
Third; solution mixture of 100 mL of methanol and 400 mL of chloroform
Fourth; solution mixture of 100 mL of methanol and 400 mL of chloroform
Fifth; solution mixture of 100 mL of methanol and 400 mL of chloroform The solvent was removed from the effluents of the first and second time by nitrogen purge, and the obtained compounds were subjected to measurements under conditions of GC-MS analysis 1 below. As a result, no pentamethylenediamine was detected, and 2,3,4,5-tetrahydropyridine having an area proportion of 99% was detected.

The compound obtained from the third time in the same manner as in the effluent of the first and second times was subjected to measurement by GC-MS analysis 1. As a result, no pentamethylenediamine was detected, and 2,3,4,5-tetrahydropyridine and unknown substance were detected.

The compound obtained from the fourth and fifth time in the same manner as in the effluent of the first and second time was subjected to measurement by GC-MS analysis 1. As a result, pentamethylenediamine and 2,3,4,5-tetrahydropyridine were not detected, and unknown substance having an area proportion of 99% was detected.

The chromatogram of the GC-MS analysis 1 of compounds of fourth and fifth times is shown in FIG. 1.

In FIG. 1, the peak at 4:08 corresponds to chloroform, and the peak at 13:26 corresponds to the unknown substance.

Figure 2:
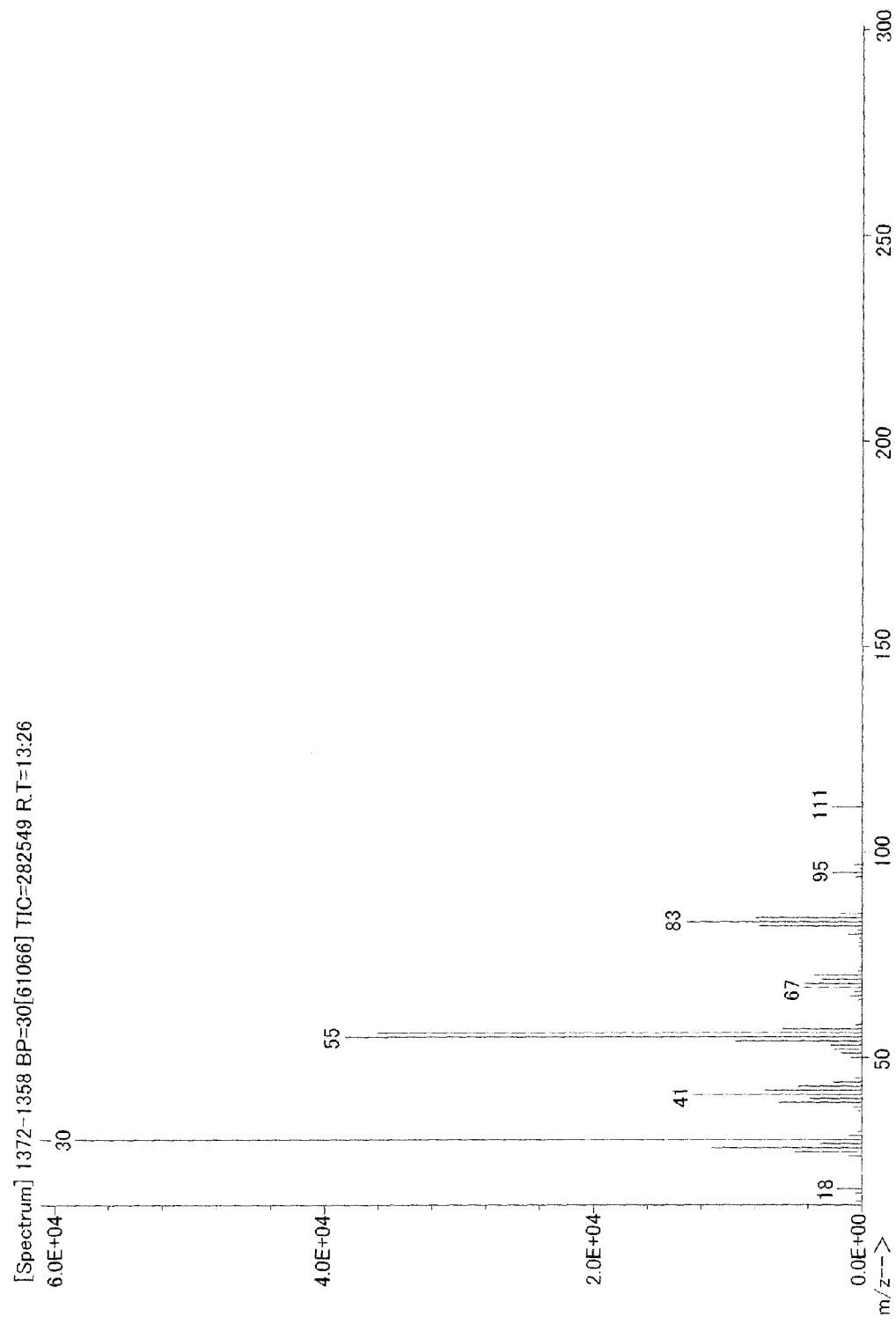
FIG. 2 shows a spectrum of GC-MS analysis 1 in structural analysis of an unknown substance.

The spectrum of the GC-MS analysis 1 of the compound of fourth and fifth times is shown in FIG. 2.

Then, to determine the chemical formula of the unknown substance, pentamethylenediamine subjected to purification by distillation obtained in the above-described (Distillation of Pentamethylenediamine) as a standard substance was added to the compound of fourth and fifth times, and the mixture was measured under conditions for GC-MS analysis 2 below. The obtained chromatogram is shown in FIG. 3.

Figure 3:
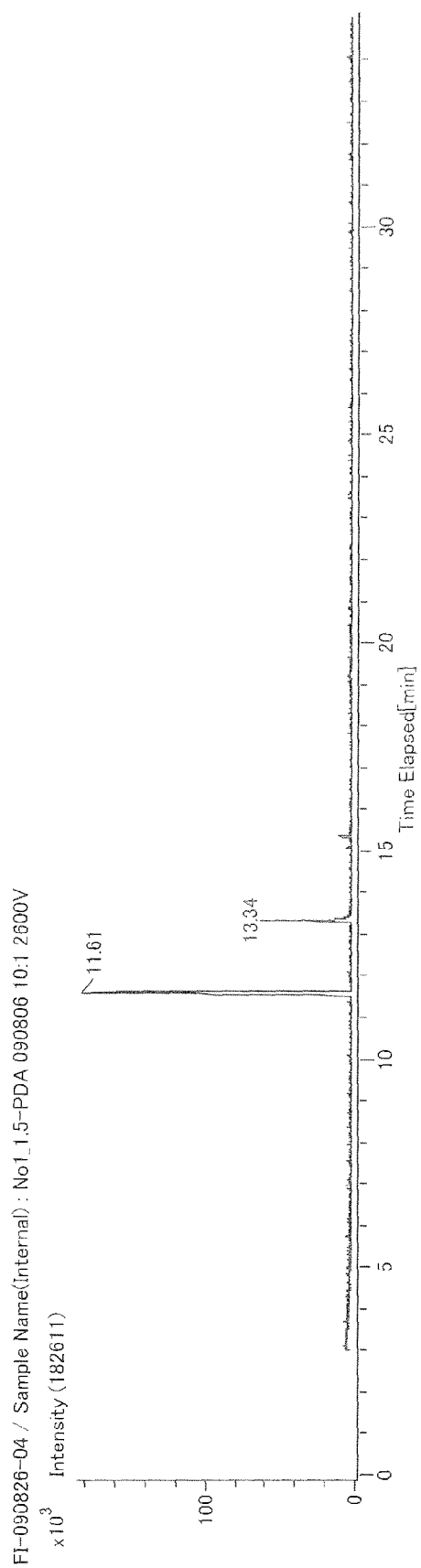
FIG. 3 shows a chromatogram of GC-MS analysis 2 in structural analysis of an unknown substance.

In FIG. 3, the peak at 11:61 corresponds to pentamethylenediamine, and the peak at 13:34 corresponds to the unknown substance.

From the results of GC-MS analysis was confirmed that the chemical formula of the unknown substance was $C_6H_{12}N_2$.

Then, to conduct Structure Analysis of Unknown Substance, the compound of the fourth and fifth times were subjected to measurement under conditions for the NMR analysis below.

Figure 4:
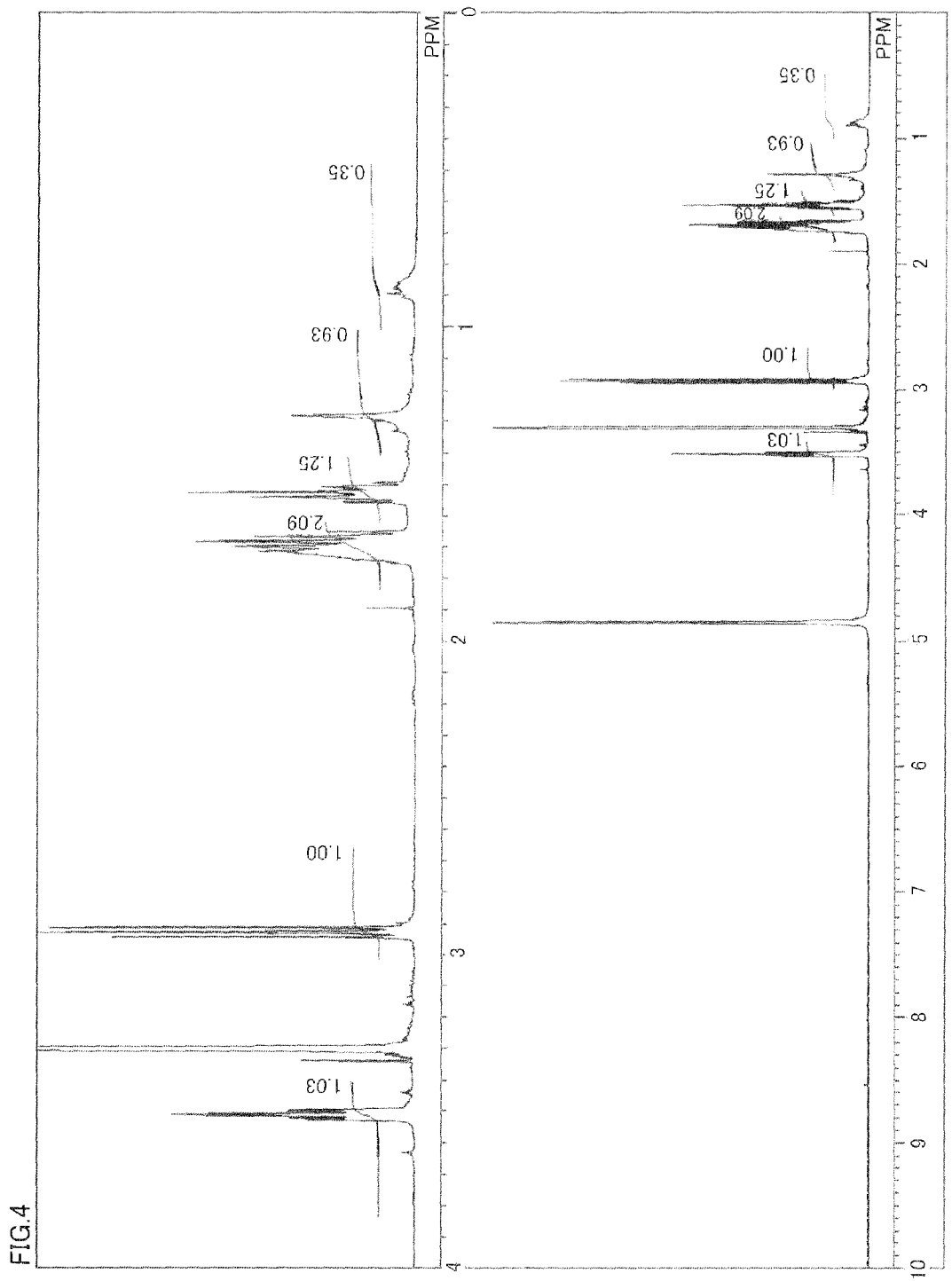
FIG. 4 shows a result of $^1$H-NMR in structural analysis of an unknown substance.
Figure 5:
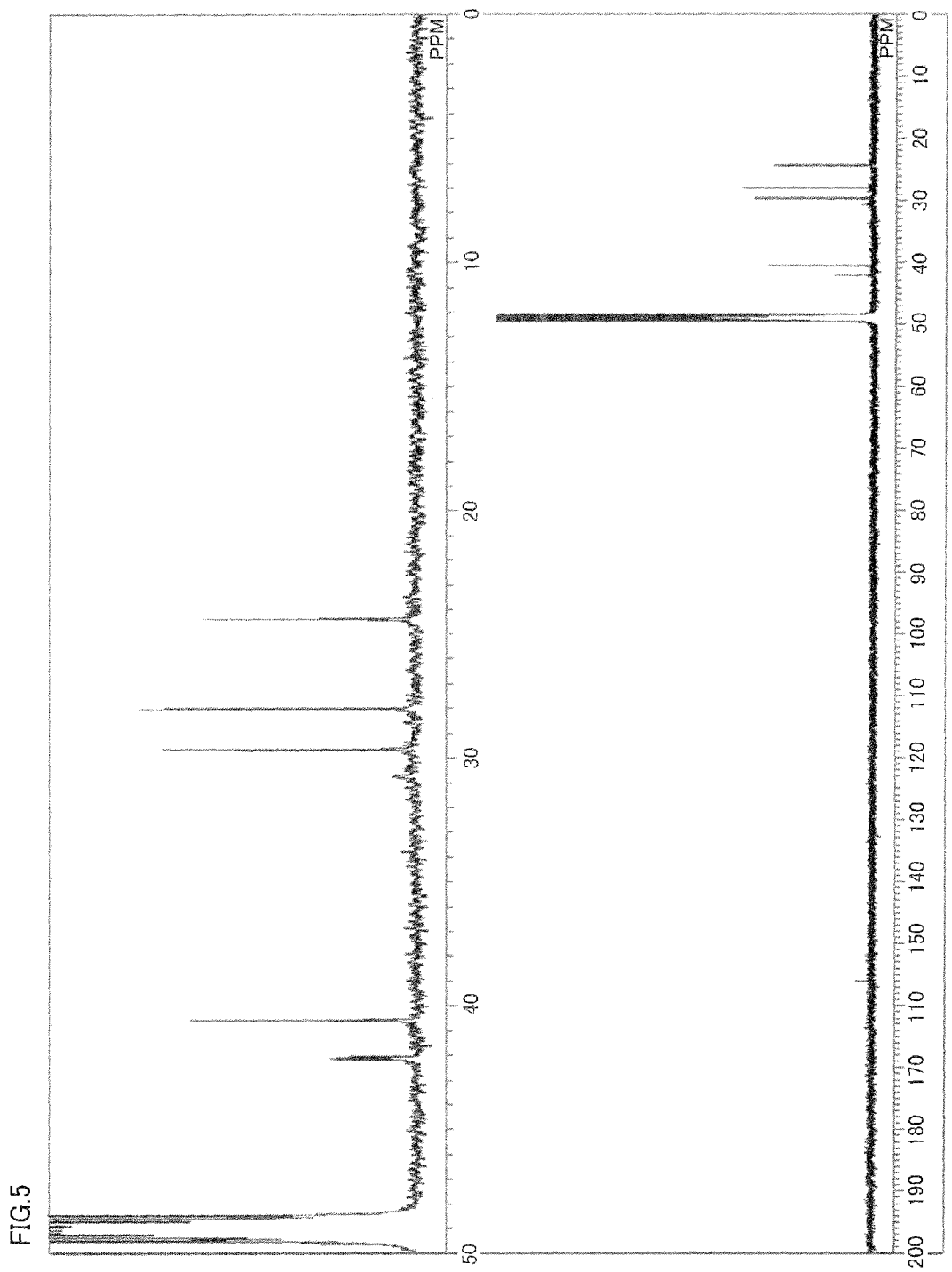
FIG. 5 shows a result of $^{13}$C-NMR in structural analysis of an unknown substance.
Figure 6:
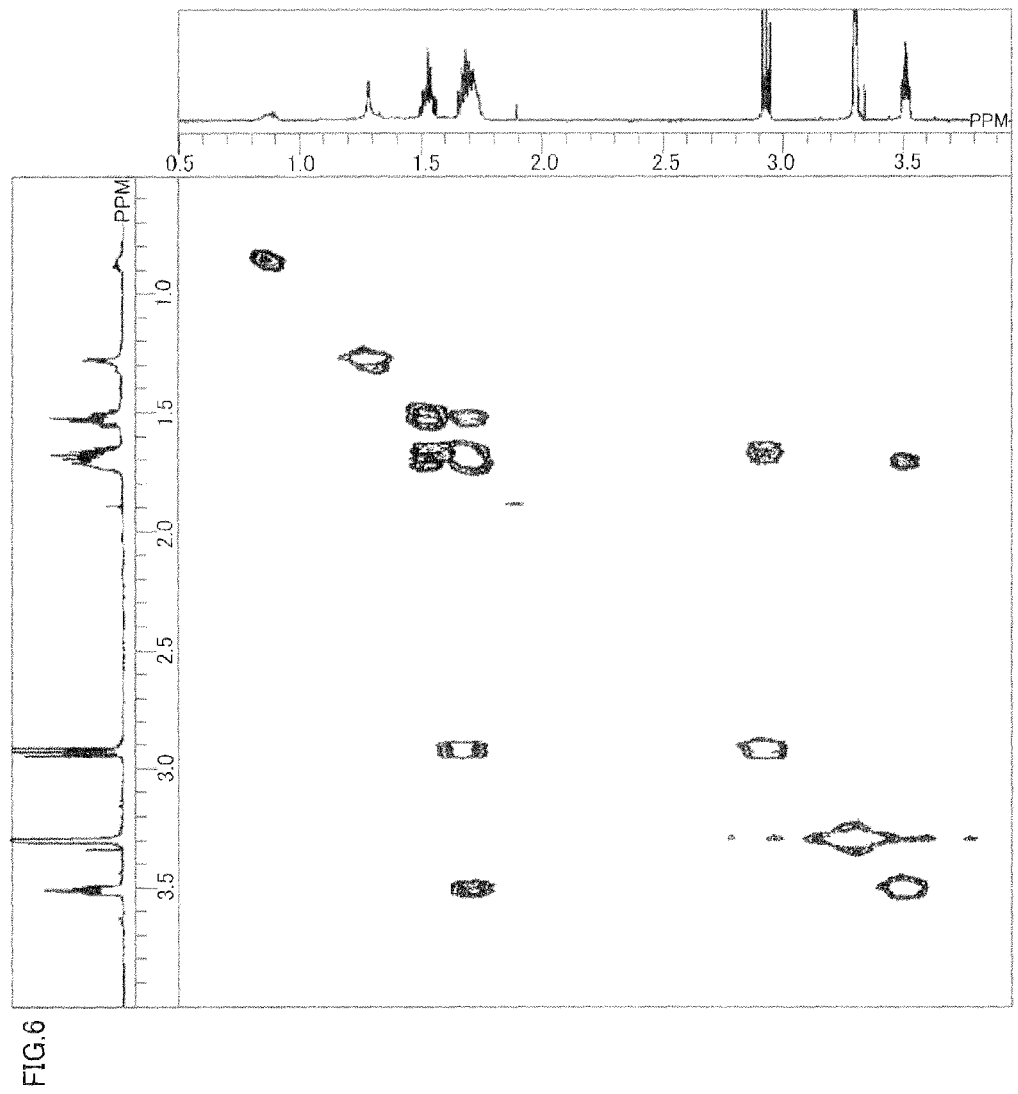
FIG. 6 shows a result of COSY in structural analysis of an unknown substance.
Figure 7:
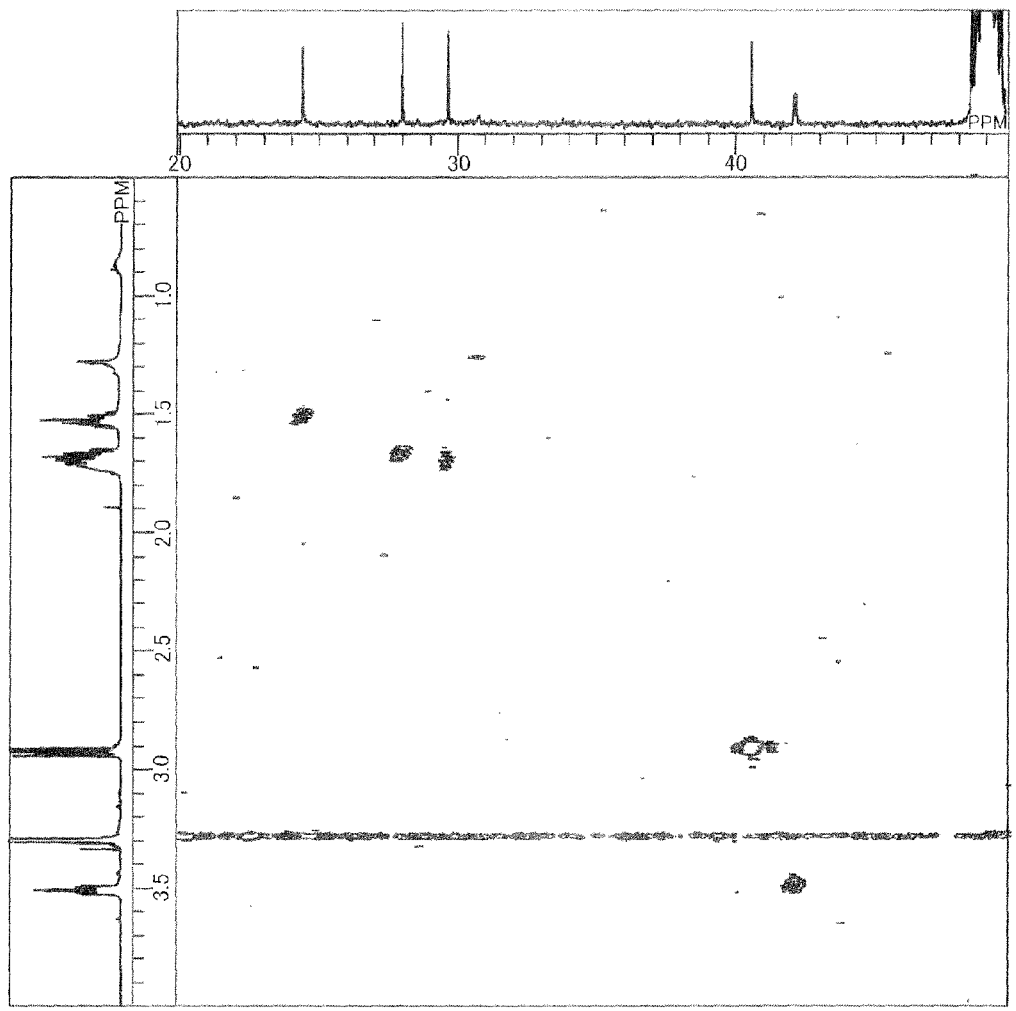
FIG. 7 shows a result of HMQC in structural analysis of an unknown substance.
Figure 8:
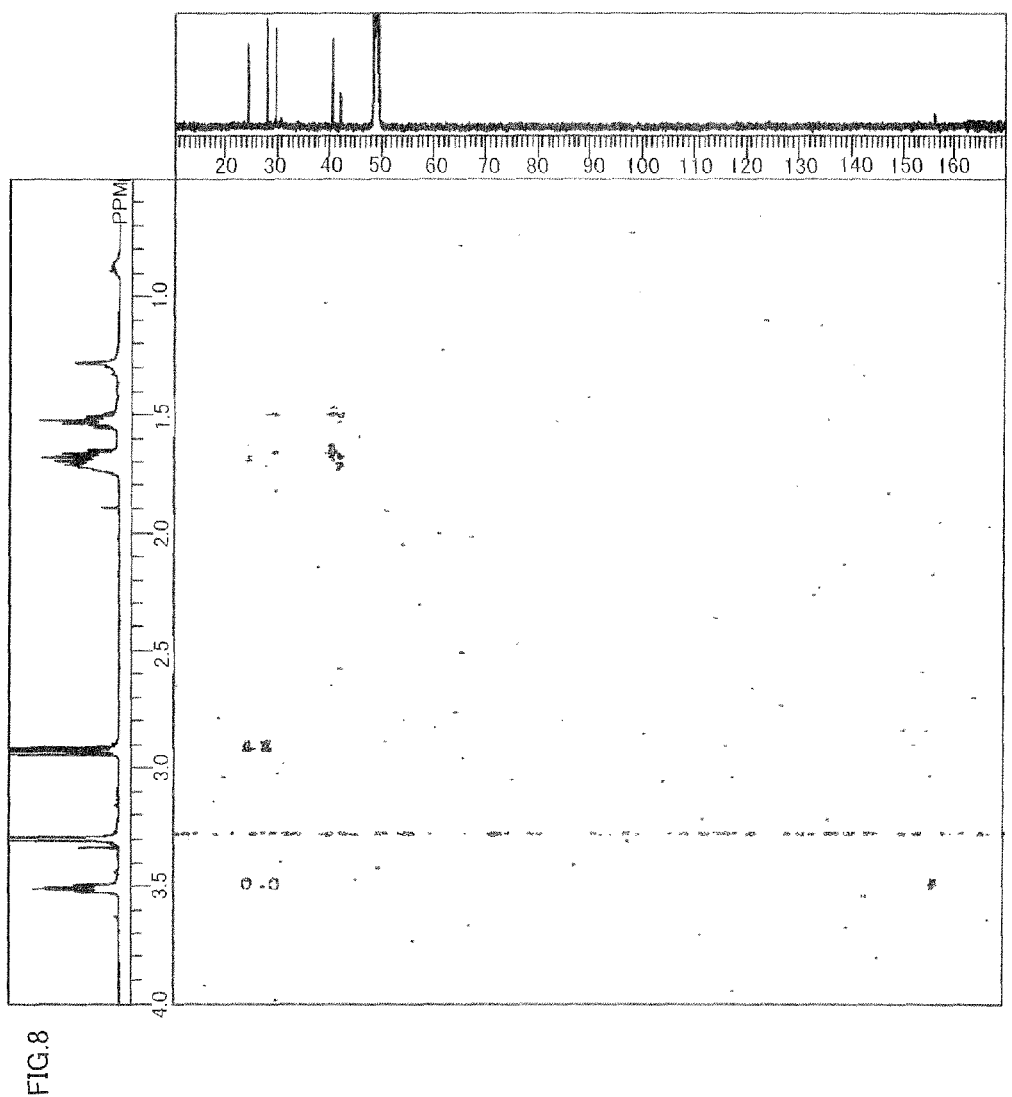
FIG. 8 shows a result of HMBC in structural analysis of an unknown substance.
Figure 9:
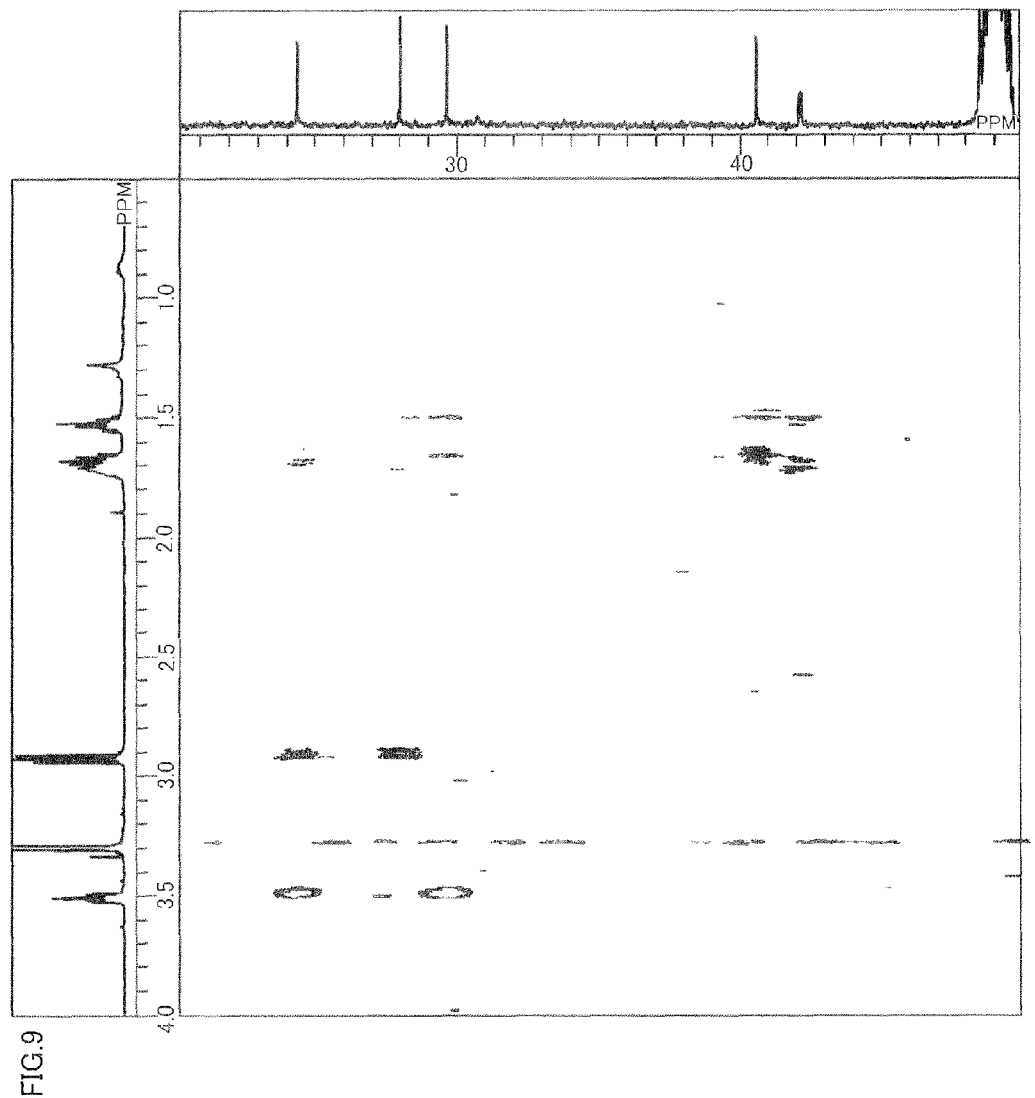
FIG. 9 shows a result (enlarged view) of HMBC in structural analysis of an unknown substance.

The $^1$H-NMR results for the unknown substance is shown in FIG. 4, and the $^{13}$C-NMR results are shown in FIG. 5, the COSY results are shown in FIG. 6, the HMQC results are shown in FIG. 7, and the HMBC results are shown in FIG. 8 and FIG. 9. FIG. 9 shows an enlarged view of the results shown in FIG. 8.

The results of GC-MS analysis and NMR analysis showed that the unknown substance was 2-(aminomethyl)-3,4,5,6-tetrahydropyridine.

The devices and conditions for GC-MS analysis and NMR analysis are shown below.
<GC-MS Analysis 1>
Device; Q1000GCK9 (manufactured by JEOL Ltd.)
Ionization Method; EI
Column; WCOT FUSED SILICA CP-SIL 8CB FOR AMINES (manufactured by VARIAN), 0.25 mmφ×30 m
Oven temperature; held at 40° C. for 3 minutes, temperature increased at 10° C./min from 40° C. to 300° C., and held at 300° C. for 11 minutes
Injection Temperature; 250° C.
He flow rate; 0.7 mL/min
Injection Mode; Split
<GC-MS Analysis 2>
Device; JMS-T100GC (manufactured by JEOL Ltd.)
Ionization Method; FI
Column; WCOT FUSED SILICA CP-SIL 8CB FOR AMINES (manufactured by VARIAN), 0.25 mmφ×30 in
Oven temperature; held at 40° C. for 3 minutes, temperature increased at 10° C./min from 40° C. to 300° C., and held at 300° C. for 11 minutes
Injection Temperature; 250° C.
He Flow Rate; 0.7 mL/min
Injection Mode; Split
<NMR Analysis>
Device; Nuclear Magnetic Resonance Device ECA500 (manufactured by JEOL Ltd.)
Measurement Method; $^1$H-NMR, $^{13}$C-NMR, COSY, HMQC, HMBC Testing Example 2

Measurement of Impurity Concentration

The concentrations of the impurities (2,3,4,5-tetrahydropyridine, and 2-(aminomethyl)-3,4,5,6-tetrahydropyridine) contained in the pentamethylenediamine of Production Examples were calculated by the method below.

That is, the purified pentamethylenediamine obtained in the above-described (Distillation of Pentamethylenediamine) and 2,3,4,5-tetrahydropyridine obtained in Testing Example 1 were mixed so that 2,3,4,5-tetrahydropyridine concentration was 2 mass %, 0.5 mass %, and 0.05 mass %. Then, a predetermined amount of o-dichlorobenzene (hereinafter may be referred to as ODCB) as an internal standard substance, and methanol as a solvent were added to the solution; the solution was subjected to measurement three times, under the same conditions as described in (Purity of Pentamethylenediamine); and a calibration curve was made setting the horizontal axis to area proportion of 2,3,4,5-tetrahydropyridine to ODCB, and setting the vertical axis to the concentration proportion of 2,3,4,5-tetrahydropyridine to ODCB.

To the pentamethylenediamine obtained in Production Examples, a predetermined amount of ODCB, and methanol as a solvent were added; the mixture was subjected to measurement under the same conditions as described in (Purity of Pentamethylenediamine); and the 2,3,4,5-tetrahydropyridine concentration was calculated from the calibration curve.

The 2-(aminomethyl)-3,4,5,6-tetrahydropyridine concentration was calculated in the same manner as in the calculation method of 2,3,4,5-tetrahydropyridine concentration.

As a result, the 2,3,4,5-tetrahydropyridine concentration of pentamethylenediamine (a) was 0.1 mass %, and the 2-(aminomethyl)-3,4,5,6-tetrahydropyridine concentration was below detection limit (detection limit 0.0006 mass %), and the total amount (total amount in the detectionable range) was 0.1 mass %.

The 2,3,4,5-tetrahydropyridine concentration of pentamethylenediamine (b) was 0.1 mass %, the 2-(aminomethyl)-3,4,5,6-tetrahydropyridine concentration was below the detection limit, and their total amount was 0.1 mass %.

The 2,3,4,5-tetrahydropyridine concentration of pentamethylenediamine (c) was 0.3 mass %, the 2-(aminomethyl)-3,4,5,6-tetrahydropyridine concentration was below the detection limit, and their total amount was 0.3 mass %.

The 2,3,4,5-tetrahydropyridine concentration of pentamethylenediamine (d) was 0.6 mass %, the 2-(aminomethyl)-3,4,5,6-tetrahydropyridine concentration was 0.5 mass %, and their total amount was 1.1 mass %.

The concentrations of impurities in those pentamethylenediamines are shown in Table 1.

TABLE 1

| | | Production Example No. | | | |
|---|---|---|---|---|---|
| | | Production Example 1 | Production Example 2 | Production Example 3 | Production Example 4 |
| Pentamethylenediamine | | a | b | c | d |
| Extractant | | n-butanol | isobutanol | n-butanol | Chloroform |
| Extraction Rate | | 91.6 | 86.0 | 93.5 | 61.7 |
| Impurity Concentration (mass %) | 2,3,4,5-tetrahydropyridine | 0.1 | 0.1 | 0.3 | 0.6 |
| | 2-(aminomethyl)-3,4,5,6-tetrahydropyridine | Below Detection Limit | Below Detection Limit | Below Detection Limit | 0.5 |
| | Total Amount of 2,3,4,5-tetrahydropyridine and 2-(aminomethyl)-3,4,5,6-tetrahydropyridine | 0.1 | 0.1 | 0.3 | 1.1 |

Example 1

Production of Pentamethylenediisocyanate (a)

A pressurized reactor with jacket equipped with an electromagnetic induction stirrer, an automatic pressure regulating valve, a thermometer, a nitrogen inlet line, a phosgene inlet line, a condenser, and a material feed pump was charged with 2000 parts by mass of o-dichlorobenzene. Then, 2300 parts by mass of phosgene was added from the phosgene inlet line, and stirring was started. Cold water was allowed to go through the reactor jacket so that the internal temperature was kept to about 10° C. Then, a solution of 400 parts by mass of pentamethylenediamine (a) dissolved in 2600 parts by mass of o-dichlorobenzene was fed through the feed pump taking 60 minutes, and cold phosgenation was started at 30° C. or less and under normal pressure. After the completion of the feed, a light-brown white slurry was formed in the pressurized reactor.

Then, while the temperature of the internal liquid of the reactor was gradually increased to 160° C., the pressure was increased to 0.25 MPa, and further hot phosgenation was performed under a pressure of 0.25 MPa, and at a reaction temperature of 160° C. for 90 minutes. During the hot phosgenation, 1100 parts by mass of phosgene was further added. In the process of the hot phosgenation, the internal liquid of the pressurized reactor became light-brown clear solution. After completion of hot phosgenation, at 100 to 140° C., nitrogen gas was allowed to pass through at 100 L/hour, and degassing was performed.

Thereafter, o-dichlorobenzene was distilled off under reduced pressure, and then pentamethylene diisocyanate was distilled off also under reduced pressure, thereby producing 558 parts by mass of pentamethylene diisocyanate ($a_0$) having a purity of 98.7%.

Then, a four-neck flask equipped with a mixer, a thermometer, a reflux pipe, and a nitrogen inlet tube was charged with 558 parts by mass of pentamethylene diisocyanate ($a_0$), and 0.02 parts by mass of tris(tridecyl) phosphite (manufactured by Johoku Chemical Co., Ltd, trade name: JP-333E) relative to 100 parts by mass of pentamethylene diisocyanate, and while introducing nitrogen, heat treatment was performed under normal pressure, at 210° C., for 2 hours, thereby producing 553 parts by mass of pentamethylene diisocyanate ($a_1$) having a purity of 98.3%. The yield of pentamethylene diisocyanate in heat treatment was 99.6%.

Then, pentamethylene diisocyanate after heat treatment was introduced to a glass-made flask, and using a distillation apparatus equipped with a distillation pipe charged with four elements of packing materials (manufactured by Sumitomo Heavy Industries, Ltd., trade name: Sumitomo/Sulzer Laboratory packing EX type), a distillation column (manufactured by SIBATA SCIENTIFIC TECHNOLOGY LTD., trade name: distillation column K type) having a reflux ratio adjusting timer, and a condenser, the pentamethylene diisocyanate was rectified while further being refluxed under the conditions of 127 to 132° C. and 2.7 KPa, thereby producing pentamethylene diisocyanate (a) having a purity of 99.9 mass %.

As a result of measurement of pentamethylene diisocyanate (a) under the GC-MS analysis conditions below, a compound having two chlorine atoms in one molecule was detected, the compound having the peaks appeared as MS spectrum fragment ion, m/z: 53, 63, 75, 80, 89, 101, 108, 116, 136, 144, 146, 179, 181, 183; the intensity ratio of 144 to 146 being about 3:1; and the intensity ratio between 179, 181, and 183 being 9:6:1. It was assumed that it was the compound represented by formula (1) or (2).

<GC-MS Analysis>
Device; Q1000GCK9 (Manufactured by JEOL Ltd.)
Ionization Method; EI
Column; DB-5MS+DG (manufactured by Agilent) 0.25 mm$\phi$×30 m, film thickness 0.25 µm
Oven temperature; held at 40° C. for 3 minutes, temperature increased at 10° C./min from 40° C. to 300° C., and held at 300° C. for 11 minutes
Injection Temperature; 200° C.
He Flow Rate; 0.7 mL/min
Injection Mode; Split The pentamethylene diisocyanate (a) contained 25 ppm in total of compound represented by formula (1) and compound represented by formula (2).

Example 2

Production of Pentamethylenediisocyanate (b)

In the same conditions and manner as in Example 1, 557 parts by mass of pentamethylene diisocyanate ($b_0$) having a purity of 98.9 mass % was produced.

Then, 557 parts by mass of pentamethylene diisocyanate ($b_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, while introducing nitrogen, heat treatment was conducted at 222° C. for 2 hours under normal pressure, thereby producing 552 parts by mass of pentamethylene diisocyanate ($b_1$) having a purity of 98.5%. The yield of pentamethylene diisocyanate in heat treatment was 99.6%.

Thereafter, rectification was performed in the same conditions and manner as in Example 1, thereby producing pentamethylene diisocyanate (b) having a purity of 99.9 mass %. Pentamethylene diisocyanate (b) contained compound represented by formula (1) and compound represented by formula (2) in total of 16 ppm.

Example 3

Production of Pentamethylenediisocyanate (c)

In the same conditions and manner as in Example 1, 557 parts by mass of pentamethylene diisocyanate ($c_0$) having a purity of 98.8 mass % was produced.

Then, 557 parts by mass of pentamethylene diisocyanate ($c_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, while introducing nitrogen, heat treatment was conducted at 236° C. for 2 hours under normal pressure, thereby producing 552 parts by mass of pentamethylene diisocyanate ($c_1$) having a purity of 98.4%. The yield of pentamethylene diisocyanate in heat treatment was 99.6%.

Thereafter, rectification was performed in the same conditions and manner as in Example 1, thereby producing pentamethylene diisocyanate (c) having a purity of 99.9 mass %. Pentamethylenediisocyanate (c) contained compound represented by formula (1) and compound represented by formula (2) in total of 7 ppm.

Example 4

Production of Pentamethylenediisocyanate (d)

In the same conditions and manner as in Example 1, 558 parts by mass of pentamethylene diisocyanate ($d_0$) having a purity of 98.7 mass % was produced.

Then, 558 parts by mass of pentamethylene diisocyanate ($d_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 180° C. for 2 hours under normal pressure, thereby producing 554 parts by mass of pentamethylene diisocyanate ($d_1$) having a purity of 98.5%. The yield of pentamethylene diisocyanate in heat treatment was 99.8%.

Thereafter, rectification was performed in the same conditions and manner as in Example 1, thereby producing pentamethylene diisocyanate (d) having a purity of 99.9 mass %. Pentamethylenediisocyanate (d) contained compound represented by formula (1) and compound represented by formula (2) in total of 190 ppm.

Example 5

Production of Pentamethylenediisocyanate (e)

552 parts by mass of pentamethylene diisocyanate ($e_0$) having a purity of 98.4 mass % was produced in the same conditions and manner as in Example 1, except that instead of pentamethylenediamine (a), pentamethylenediamine (c) was used.

Then, 552 parts by mass of pentamethylene diisocyanate ($e_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 180° C. for 2 hours under normal pressure, thereby producing 548 parts by mass of pentamethylene diisocyanate ($e_1$) having a purity of 98.1%. The yield of pentamethylene diisocyanate in heat treatment was 99.7%.

Thereafter, rectification was performed in the same conditions and manner as in Example 1, thereby producing pentamethylene diisocyanate (e) having a purity of 99.9 mass %. Pentamethylenediisocyanate (e) contained 0.008% of HC, and compound represented by formula (1) and compound represented by formula (2) in total of 280 ppm.

Example 6

Production of Pentamethylenediisocyanate (f)

In the same conditions and manner as in Example 1, 558 parts by mass of pentamethylene diisocyanate ($f_0$) having a purity of 98.7 mass % was produced.

Then, 558 parts by mass of pentamethylene diisocyanate ($f_0$) was put into a four-neck flask equipped with a mixer, a thermometer, a reflux pipe, and a nitrogen inlet tube, and while introducing nitrogen, heat treatment was conducted at 180° C. for 2 hours under normal pressure, thereby producing 554 parts by mass of pentamethylene diisocyanate ($f_r$) having a purity of 93.1%. The yield of pentamethylene diisocyanate in heat treatment was 94.3%.

Thereafter, rectification was performed in the same conditions and manner as in Example 1, thereby producing pentamethylene diisocyanate (f) having a purity of 99.8 mass %. Pentamethylenediisocyanate (f) contained compound represented by formula (1) and compound represented by formula (2) in total of 340 ppm.

Comparative Example 1

Production of Pentamethylenediisocyanate (g)

In the same conditions and manner as in Example 1, 559 parts by mass of pentamethylene diisocyanate ($g_0$) having a purity of 98.6 mass % was produced.

Then, 559 parts by mass of pentamethylene diisocyanate ($g_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 160° C. for 2 hours under normal pressure, thereby producing 555 parts by mass of pentamethylene diisocyanate ($g_1$) having a purity of 98.4%. The yield of pentamethylene diisocyanate in heat treatment was 99.8%.

Thereafter, rectification was performed in the same conditions and manner as in Example 1, thereby producing pentamethylene diisocyanate (g) having a purity of 99.6 mass %. Pentamethylenediisocyanate (g) had 0.008% of HC, and compound represented by formula (1) and compound represented by formula (2) in total of 410 ppm.

Comparative Example 2

Production of Pentamethylenediisocyanate (h)

552 parts by mass of pentamethylene diisocyanate ($h_0$) having a purity of 98.4 mass % was produced in the same conditions and manner as in Example 1, except that pentamethylenediamine (c) was used instead of pentamethylenediamine (a).

Then, 552 parts by mass of pentamethylene diisocyanate ($h_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 160° C. for 2 hours under normal pressure, thereby producing 549 parts by mass of pentamethylene diisocyanate ($h_1$) having a purity of 98.2%. The yield of pentamethylene diisocyanate in heat treatment was 99.8%.

Thereafter, rectification was performed in the same conditions and manner as in Example 1, thereby producing pentamethylene diisocyanate (h) having a purity of 99.5 mass %. Pentamethylene diisocyanate (h) contained compound represented by formula (1) and compound represented by formula (2) in total of 505 ppm.

Comparative Example 3

Production of Pentamethylenediisocyanate (i)

In the same conditions and manner as in Example 1, 558 parts by mass of pentamethylene diisocyanate ($i_0$) having a purity of 98.7 mass % was produced.

Then, 558 parts by mass of pentamethylene diisocyanate ($i_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 247° C. for 2 hours under normal pressure, thereby producing 552 parts by mass of pentamethylene diisocyanate ($i_1$) having a purity of 91.7%. The yield of pentamethylene diisocyanate in heat treatment was 92.9%.

Thereafter, rectification was performed in the same conditions and manner as in Example 1, thereby producing pentamethylene diisocyanate (i) having a purity of 99.9 mass %. Pentamethylene diisocyanate (i) contained 0.001% of HC, and compound represented by formula (1) and compound represented by formula (2) in total of 2 ppm.

Comparative Example 4

Production of Pentamethylenediisocyanate (j)

561 parts by mass of pentamethylene diisocyanate ($j_0$) having a purity of 92.1 mass % was produced in the same conditions and manner as in Example 1, except that pentamethylenediamine (d) was used instead of pentamethylenediamine (a).

Then, 561 parts by mass of pentamethylene diisocyanate ($j_0$), and 0.02 parts by mass of tris(tridecyl) phosphite relative to 100 parts by mass of pentamethylene diisocyanate were put into a four-neck flask equipped with a mixer, a thermometer, a reflux pipe, and a nitrogen inlet tube, and while introducing nitrogen, heat treatment was conducted at 210° C. for 2 hours under normal pressure, thereby producing 555 parts by mass of pentamethylene diisocyanate ($j_1$) having a purity of 90.2%. The yield of pentamethylene diisocyanate in heat treatment was 97.9%.

Thereafter, rectification was performed in the same conditions and manner as in Example 1, thereby producing pentamethylene diisocyanate (j) having a purity of 99.1 mass %. Pentamethylene diisocyanate (j) contained compound represented by formula (1) and compound represented by formula (2) in total of 830 ppm.

TABLE 2

|  | Example No. | | |
| --- | --- | --- | --- |
|  | Example 1 | Example 2 | Example 3 |
| Pentamethylenediisocyanate | a | b | c |
| Material Pentamethylenediamine | a | a | a |
| Heat Treatment Temperature (° C.) | 210 | 212 | 236 |
| Phosphorus-containing compound (stabilizer) | JP-333E | JP-333E | JP-333E |
| Yield of Pentamethylenediisocyanate in Heat Treatment (mass %) | 99.6 | 99.6 | 99.6 |

TABLE 2-continued

|  |  |  |  |
|---|---|---|---|
| Concentration of (ppm) of Compounds of Formulas (1) and (2) | 25 | 16 | 7 |
| Purity of Pentamethylenediisocyanate (mass %) | 99.9 | 99.9 | 99.9 |

|  | Example No. | | |
|---|---|---|---|
|  | Example 4 | Example 5 | Example 6 |
| Pentamethylenediisocyanate | d | e | f |
| Material Pentamethylenediamine | a | c | a |
| Heat Treatment Temperature (° C.) | 180 | 180 | 180 |
| Phosphorus-containing compound (stabilizer) | JP-333E | JP-333E | Not Contained |
| Yield of Pentamethylenediisocyanate in Heat Treatment (mass %) | 99.8 | 99.7 | 94.3 |
| Concentration of (ppm) of Compounds of Formula (1) and (2) | 190 | 280 | 340 |
| Purity of Pentamethylenediisocyanate (mass %) | 99.9 | 99.9 | 99.8 |

|  | Comparative Example No. | | | |
|---|---|---|---|---|
|  | Comparative Example 1 | Comparative Example 2 | Comparative Example 3 | Comparative Example 4 |
| Pentamethylenediisocyanate | g | h | i | j |
| Material Pentamethylenediamine | a | c | a | d |
| Heat Treatment Temperature (° C.) | 160 | 160 | 247 | 210 |
| Phosphorus-containing compound (stabilizer) | JP-333E | JP-333E | JP-333E | JP-333E |
| Yield of Pentamethylenediisocyanate in Heat Treatment (mass %) | 99.8 | 99.8 | 92.9 | 97.9 |
| Concentration of (ppm) of Compounds of Formula (1) and (2) | 410 | 505 | 2 | 830 |
| Purity of Pentamethylenediisocyanate (mass %) | 99.6 | 99.5 | 99.9 | 99.1 |

Example 7

Production of Polyisocyanate Composition (A)

Pentamethylenediisocyanate (a) was transferred to a metal container, and 0.005 parts by mass of 2,6-di(tert-butyl)-4-methylphenol thereinafter may be referred to as BHT) relative to 100 parts by mass of pentamethylene diisocyanate was added thereto. After nitrogen purge, the mixture was allowed to stand in a 50° C. oven for 14 days, and storage stability test was performed. Pentamethylenediisocyanate (a) had a purity of 99.8% after the storage stability test.

A four-neck flask equipped with a mixer, a thermometer, a reflux pipe, and a nitrogen inlet tube was charged with 500 parts by mass of pentamethylene diisocyanate (a) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and reaction was continued until reaching a predetermined reaction rate. The reaction rate reached a predetermined reaction rate after 50 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (A).

The polyisocyanate composition (A) had a pentamethylene diisocyanate concentration of 0.3 mass %, an isocyanate trimer concentration of 58 mass %, an isocyanate group concentration 1 of 24.4 mass %, a viscosity 1 at 25° C. of 1660 mPa·s, and a color 1 of APHA 20. These values measured are shown in Table 3 as measured values before heat acceleration test.

Then, polyisocyanate composition (A) was transferred to a metal-made container. After nitrogen purge, the mixture was allowed to stand in a 40° C. oven for 14 days, thereby carrying out heat acceleration test. The polyisocyanate composition after the test had an isocyanate group concentration 2 of 24.0 mass %, viscosity 2 at 25° C. of 1860 mPa·s, and a color 2 of APHA20. The measured values are shown as measured values after heat acceleration test in Table 3.

Example 8

Production of Polyisocyanate Composition (B)

Pentamethylenediisocyanate (b) was transferred to a metal container, and 0.005 parts by mass of 2,6-di(tert-butyl)-4-methylphenol (hereinafter may be referred to as BHT) relative to 100 parts by mass of pentamethylene diisocyanate was added thereto. After nitrogen purge, the mixture was allowed to stand in a 50° C. oven for 14 days, and storage stability test was performed. Pentamethylenediisocyanate (b) had a purity of 99.8% after the storage stability test.

A four-neck flask equipped with a mixer, a thermometer, a reflux pipe, and a nitrogen inlet tube was charged with 500 parts by mass of pentamethylene diisocyanate (b) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and reaction was continued until reaching a predetermined reaction rate. The reaction rate reached a predetermined reaction rate after 40 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (B).

The polyisocyanate composition (B) had a pentamethylene diisocyanate concentration of 0.3 mass %, an isocyanate trimer concentration of 60 mass %, an isocyanate group concentration 1 of 24.8 mass %, a viscosity 1 at 25° C. of 1610 mPa·s, and a color 1 of APHA 20. These values measured are shown in Table 3 as measured values before heat acceleration test.

Then, polyisocyanate composition (B) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 24.6 mass %, a viscosity 2 at 25° C. of 1740 mPa·s, and a color 2 of APHA20. The measured values are shown as measured values after heat acceleration test in Table 3.

Example 9

Production of Polyisocyanate Composition (C)

Pentamethylenediisocyanate (c) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (c) had a purity of 99.8% after the storage stability test.

A four-neck flask equipped with a mixer, a thermometer, a reflux pipe, and a nitrogen inlet tube was charged with 500 parts by mass of pentamethylene diisocyanate (c) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.025 parts by mass of a catalyst was further added. The reaction rate was reached a predetermined reaction rate after 40 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (C).

The polyisocyanate composition (C) had a pentamethylene diisocyanate concentration of 0.3 mass %, an isocyanate trimer concentration of 59 mass %, an isocyanate group concentration 1 of 24.6 mass %, a viscosity 1 at 25° C. of 1630 mPa·s, and a color 1 of APHA 20. These values measured are shown in Table 3 as measured values before heat acceleration test.

Then, polyisocyanate composition (C) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 24.3 mass %, a viscosity 2 at 25° C. of 1780 mPa·s, and a color 2 of APHA20. The measured values are shown as measured values after heat acceleration test in Table 3.

Example 10

Production of Polyisocyanate Composition (D)

Pentamethylenediisocyanate (d) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (d) had a purity of 99.8% after the storage stability test.

A four-neck flask equipped with a mixer, a thermometer, a reflux pipe, and a nitrogen inlet tube was charged with 500 parts by mass of pentamethylene diisocyanate (d) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.025 parts by mass of a catalyst was further added. The reaction rate reached a predetermined reaction rate after 50 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (D).

The polyisocyanate composition (D) had a pentamethylene diisocyanate concentration of 0.4 mass %, an isocyanate trimer concentration of 58 mass %, an isocyanate group concentration 1 of 24.5 mass %, a viscosity 1 at 25° C. of 1670 mPa·s, and a color 1 of APHA 20. These values measured are shown in Table 3 as measured values before heat acceleration test.

Then, polyisocyanate composition (D) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 24.0 mass %, a viscosity 2 at 25° C. of 1870 mPa·s, and a color 2 of APHA20. The measured values are shown as measured values after heat acceleration test in Table 3.

Example 11

Production of Polyisocyanate Composition (E)

Pentamethylenediisocyanate (e) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (e) had a purity of 99.8% after the storage stability test.

A four-neck flask equipped with a mixer, a thermometer, a reflux pipe, and a nitrogen inlet tube was charged with 500 parts by mass of pentamethylene diisocyanate (e) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.025 parts by mass of a catalyst was further added. The reaction rate reached a predetermined reaction rate after 50 minutes, and thus, 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (E).

The polyisocyanate composition (E) had a pentamethylene diisocyanate concentration of 0.5 mass %, an isocyanate trimer concentration of 58 mass %, an isocyanate group concentration 1 of 24.3 mass %, a viscosity 1 at 25° C. of 1680 mPa·s, and a color 1 of APHA 30. These values measured are shown in Table 3 as measured values before heat acceleration test.

Then, polyisocyanate composition (E) was transferred to a metal-made container, and after nitrogen purge, the mixture was allowed to stand in a 40° C., oven for 14 days, thereby carrying out heat acceleration test. The polyisocyanate composition after the test had an isocyanate group concentration 2 of 23.8 mass %, a viscosity 2 at 25° C. of 1880 mPa·s, and a color 2 of APHA40. The measured values are shown as measured values after heat acceleration test in Table 3.

Example 12

Production of Polyisocyanate Composition (F)

Pentamethylenediisocyanate (0 was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (f) had a purity of 99.6% after the storage stability test.

A four-neck flask equipped with a mixer, a thermometer, a reflux pipe, and a nitrogen inlet tube was charged with 500 parts by mass of pentamethylene diisocyanate (f) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.05 parts by mass of a catalyst was further added. The reaction rate reached a predetermined reaction rate after 50 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (F).

The polyisocyanate composition (F) had a pentamethylene diisocyanate concentration of 0.4 mass %, an isocyanate trimer concentration of 53 mass %, an isocyanate group concentration 1 of 23.6 mass %, a viscosity 1 at 25° C. of 1890 mPa·s, and a color 1 of APHA 50. These values measured are shown in Table 3 as measured values before heat acceleration test.

Then, polyisocyanate composition (F) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 22.5 mass %, a viscosity 2 at 25° C. of 2290 mPa·s, and a color 2 of APHA70. The measured values are shown as measured values after heat acceleration test in Table 3.

Comparative Example 5

Production of Polyisocyanate Composition (G)

Pentamethylenediisocyanate (g) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate had a purity of 99.2% after the storage stability test.

A four-neck flask equipped with a mixer, a thermometer, a reflux pipe, and a nitrogen inlet tube was charged with 500 parts by mass of pentamethylene diisocyanate (g) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.1 parts by mass of a catalyst was further added. The reaction rate reached a predetermined reaction rate after 60 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (G).

The polyisocyanate composition (G) had a pentamethylene diisocyanate concentration of 0.5 mass %, an isocyanate trimer concentration of 49 mass %, an isocyanate group concentration 1 of 22.0 mass %, a viscosity 1 at 25° C. of 2130 mPa·s, and a color 1 of APHA 100. These values measured are shown in Table 3 as measured values before heat acceleration test.

Then, polyisocyanate composition (G) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 20.9 mass %, a viscosity 2 at 25° C. of 2710 mPa·s, and a color 2 of APHA 130. The measured values are shown as measured values after heat acceleration test in Table 3.

Comparative Example 6

Production of Polyisocyanate Composition (H)

Pentamethylenediisocyanate (i) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (i) had a purity of 99.0% after the storage stability test.

A four-neck flask equipped with a mixer, a thermometer, a reflux pipe, and a nitrogen inlet tube was charged with 500 parts by mass of pentamethylene diisocyanate (i) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.075 parts by mass of a catalyst was further added. The reaction rate reached a predetermined reaction rate after 60 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (H).

The polyisocyanate composition (H) had a pentamethylene diisocyanate concentration of 0.6 mass %, an isocyanate trimer concentration of 50 mass %, an isocyanate group concentration 1 of 22.6 mass %, a viscosity 1 at 25° C. of 2070 mPa·s, and a color 1 of APHA 90. These values measured are shown in Table 3 as measured values before heat acceleration test.

Then polyisocyanate composition (H) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 21.7 mass %, a viscosity 2 at 25° C. of 2610 mPa·s, and a color 2 of APHA 120. The measured values are shown as measured values after heat acceleration test in Table 3.

Comparative Example 7

Production of Polyisocyanate Composition (I)

Pentamethylenediisocyanate (j) was transferred to a metal container, and 0.005 parts by mass of BHT relative to 100 parts by mass of pentamethylene diisocyanate was added thereto. After nitrogen purge, the mixture was allowed to stand in a 50° C. oven for 14 days, and storage stability test was performed. Pentamethylenediisocyanate (j) had a purity of 98.4% after the storage stability test.

A four-neck flask equipped with a mixer, a thermometer, a reflux pipe, and a nitrogen inlet tube was charged with 500 parts by mass of pentamethylene diisocyanate (j) after storage stability test, 1 part by mass of isobutyl alcohol, 0.3 parts by mass of 2,6-di(tert-butyl)-4-methylphenol, and 0.3 parts by mass of tris(tridecyl) phosphite, and reaction was performed at 80° C. for 2 hours.

Then, 0.05 parts by mass of N-(2-hydroxypropyl)-N,N,N-trimethylammonium-2-ethylhexanoate as a trimerization catalyst was added. The refractive index and the isocyanate purity were measured, and the reaction was continued until reaching a predetermined reaction rate, and 0.25 parts by mass of a catalyst was further added. The reaction rate reached a predetermined reaction rate after 80 minutes, and thus 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (I).

The polyisocyanate composition (I) had a pentamethylene diisocyanate concentration of 0.7 mass %, an isocyanate trimer concentration of 44 mass %, an isocyanate group concentration 1 of 20.3 mass %, a viscosity 1 at 25° C. of 2280 mPa·s, and a color 1 of APHA 150. These values measured are shown in Table 3 as measured values before heat acceleration test.

Then, polyisocyanate composition (I) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 19.1 mass %, a viscosity 2 at 25° C. of 3010 mPa·s, and a color 2 of APHA190. The measured values are shown as measured values after heat acceleration test in Table 3.

TABLE 3

| Example and Comparative Example No. | Example 7 | Example 8 | Example 9 | Example 10 | Example 11 |
|---|---|---|---|---|---|
| Polyisocyanate Composition | A | B | C | D | E |
| Pentamethylenediisocyanate | a | b | c | d | e |
| Pentamethylenediisocyanate Concentration (mass %) | 0.3 | 0.3 | 0.3 | 0.4 | 0.5 |
| Isocyanurate trimer Concentration (mass %) | 58 | 60 | 59 | 58 | 58 |
| Amount of Catalyst Added (ppm) | 100 | 100 | 100 | 100 | 150 |
| Reaction Time (min) | 50 | 40 | 40 | 50 | 50 |

TABLE 3-continued

| | | | | | | |
|---|---|---|---|---|---|---|
| Before Heat Acceleration Test | Isocyanate Group Concentration 1 (mass %) | 24.4 | 24.8 | 24.6 | 24.5 | 24.3 |
| | Viscosity 1(mPa·s) | 1660 | 1610 | 1630 | 1670 | 1680 |
| | Color 1(—) | 20 | 20 | 20 | 20 | 30 |
| After Heat Acceleration Test | Isocyanate Group Concentration2 (mass %) | 24.0 | 24.6 | 24.3 | 24.0 | 23.8 |
| | Viscosity 2(mPa·s) | 1860 | 1740 | 1780 | 1870 | 1880 |
| | Color 2(—) | 20 | 20 | 20 | 20 | 40 |
| Decrease Rate in Isocyanate Group Concentration After Heat Acceleration Test(%) | | 2 | 1 | 1 | 2 | 2 |
| Increase Rate in Viscosity After Heat Acceleration Test (%) | | 12 | 8 | 9 | 12 | 12 |
| Changes in Color After Heat Acceleration Test (Color 2 − Color 1) | | 0 | 0 | 0 | 0 | 10 |

| Example and Comparative Example No. | Example 12 | Comparative Example 5 | Comparative Example 6 | Comparative Example 7 |
|---|---|---|---|---|
| Polyisocyanate Composition | F | G | H | I |
| Pentamethylenediisocyanate | f | g | i | j |
| Pentamethylenediisocyanate Concentration (mass %) | 0.4 | 0.5 | 0.6 | 0.7 |
| Isocyanurate Trimer Concentration (mass %) | 53 | 49 | 50 | 44 |
| Amount of Catalyst Added (ppm) | 200 | 300 | 250 | 600 |
| Reaction Time (min) | 50 | 60 | 60 | 80 |
| Before Heat Acceleration Test — Isocyanate Group Concentration1 (mass %) | 23.2 | 22.0 | 22.6 | 20.3 |
| Viscosity 1 (mPa·S) | 1890 | 2130 | 2070 | 2280 |
| Color 1 (—) | 50 | 100 | 90 | 150 |
| After Heat Acceleration Test — Isocyanate Group Concentration 2 (mass %) | 22.5 | 20.9 | 21.7 | 19.1 |
| Viscosity 2(mPa·s) | 2290 | 2710 | 2610 | 3010 |
| Color 2(—) | 70 | 130 | 120 | 190 |
| Decrease in Isocyanate Group Concentration After Heat Acceleration Test(%) | 3 | 5 | 4 | 6 |
| Increase in Viscosity After Heat Acceleration Test (%) | 21 | 27 | 26 | 32 |
| Changes in Color After Heat Acceleration Test (Color 2 − Color 1) | 20 | 30 | 30 | 40 |

Example 13

Production of Polyisocyanate Composition (J)

A four-neck flask equipped with a mixer, a thermometer, a reflux pipe, and a nitrogen inlet tube was charged with 500 parts by mass of pentamethylene diisocyanate (a), 19 parts by mass of isobutanol, 0.3 parts by mass of 2,6-di(t-butyl)-4-methylphenol, and 0.3 parts by mass of tris(tridecyl) phosphite, and the temperature was increased to 85° C. thereby performing urethane-forming reaction for 3 hours. Then, 0.02 parts by mass of lead octoate was added as an allophanate-forming catalyst, and reaction was performed until the isocyanate group concentration reached calculated value. Thereafter, 0.02 parts by mass of o-toluenesulfonamide was added. The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (J).

The polyisocyanate composition (J) had a pentamethylene diisocyanate concentration of 0.2 mass %, an isocyanate group concentration 1 of 20.5 mass %, a viscosity 1 at 25° C. of 190 mPa·s, and a color 1 of APHA 20. These values measured are shown in Table 4 as measured values before heat acceleration test.

Then, polyisocyanate composition (J) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 20.1 mass %, a viscosity 2 at 25° C. of 210 mPa·s, and a color 2 of APHA20. The measured values are shown as measured values after heat acceleration test in Table 4.

Comparative Example 8

Production of Polyisocyanate Composition (K)

Urethane-forming and allophanate-forming reaction were performed in the same manner as Example 13 using pentamethylene diisocyanate (g) instead of pentamethylene diisocyanate (a). However, it was confirmed that the reaction velocity was low based on the isocyanate group concentration measurement, 0.01 parts by mass of lead octoate was further added, thereby producing polyisocyanate composition (K).

The polyisocyanate composition (K) had a pentamethylene diisocyanate concentration of 0.3 mass %, an isocyanate group concentration 1 of 18.2 mass %, a viscosity 1 at 25° C. of 270 mPa·s, and a color 1 of APHA 70. These values measured are shown in Table 4 as measured values before heat acceleration test.

Then, polyisocyanate composition (K) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 17.0 mass %, a viscosity 2 at 25° C. of 340 mPa·s, and a color 2 of APHA110. The measured values are shown as measured values after heat acceleration test in Table 4.

Example 14

Production of Polyisocyanate Composition (L)

A four-neck flask equipped with a mixer, a thermometer, a reflux pipe, and a nitrogen inlet tube was charged with 500 parts by mass of pentamethylene diisocyanate (a), 0.2 parts by mass of tris(tridecyl) phosphite, 8 parts by mass of trimethylphosphoric acid, and 4 parts by mass of water. The temperature was increased to 130° C., and reaction was performed until the isocyanate group concentration reached the calculated value. The obtained reaction solution was allowed to pass through a thin film distillation apparatus (degree of vacuum 0.093 KPa, temperature 150° C.) to remove unreacted pentamethylene diisocyanate, thereby producing polyisocyanate composition (L).

The polyisocyanate composition (L) had a pentamethylene diisocyanate concentration of 0.6 mass %, an isocyanate group concentration 1 of 25.0 mass %, a viscosity 1 at 25° C. of 2700 mPa·s, and a color 1 of APHA 20. These values measured are shown in Table 4 as measured values before heat acceleration test.

Then, polyisocyanate composition (L) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 24.2 mass %, a viscosity 2 at 25° C. of 3110 mPa·s, and a color 2 of APHA20. The measured values are shown as measured values after heat acceleration test in Table 4.

Comparative Example 9

Production of Polyisocyanate Composition (M)

Using pentamethylene diisocyanate (g) instead of pentamethylene diisocyanate (a), reaction was conducted in the same manner as in Example 14, thereby producing polyisocyanate composition (M).

The polyisocyanate composition (M) had a pentamethylene diisocyanate concentration of 0.7 mass %, an isocyanate group concentration 1 of 22.3 mass %, a viscosity 1 at 25° C. of 3780 mPa·s, and a color 1 of APHA 60. These values measured are shown in Table 4 as measured values before heat acceleration test.

Then, polyisocyanate composition (M) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 20.9 mass %, a viscosity 2 at 25° C. of 4880 mPa·s, and a color 2 of APHA90. The measured values are shown as measured values after heat acceleration test in Table 4.

Example 15

Production of Polyisocyanate Composition (N)

A four-neck flask equipped with a mixer, a thermometer, a reflux pipe, and a nitrogen inlet tube was charged with 500 parts by mass of pentamethylene diisocyanate (a) of Example 1, and as a low-molecular-weight polyol, 40 parts by mass of trimethylolpropane (abbreviation: TMP) (equivalent ratio (NCO/OH)=5.8). The temperature was increased to 75° C. in a nitrogen atmosphere, and after confirming that trimethylolpropane was dissolved, reaction was performed at 83° C. until the isocyanate group concentration reached the calculated value.

Then, after the temperature of the reaction solution was decreased to 55° C. 350 parts by mass of a mixed extractant (n-hexane/ethyl acetate=90/10 (mass ratio)) was added thereto. The reaction solution was stirred for 10 min, and after the reaction solution was allowed to stand for 10 min, the extractant layer was removed. This extraction operation was repeated 4 times.

Thereafter, the extractant remained in the reaction liquid was removed from the obtained reaction liquid under reduced pressure, while heating to 80° C. Ethyl acetate was further added, and the polyisocyanate composition concentration was adjusted to 75 mass %, thereby producing polyisocyanate composition (N). The polyisocyanate composition (N) had a pentamethylene diisocyanate concentration of 0.3 mass %, an isocyanate group concentration 1 of 20.7 mass %, a viscosity 1 at 25° C. of 480 mPa·s, and a color 1 of APHA 20. These values measured are shown in Table 4 as measured values before heat acceleration test.

Then, polyisocyanate composition (N) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 20.3 mass %, a viscosity 2 at 25° C. of 540 mPa·s, and a color 2 of APHA20. The measured values are shown as measured values after heat acceleration test in Table 4.

Comparative Example 10

Production of Polyisocyanate Composition (O)

Using pentamethylene diisocyanate (g) instead of pentamethylene diisocyanate (a), reaction was conducted in the same manner as in Example 15, thereby producing polyisocyanate composition (O).

The polyisocyanate composition (O) had a pentamethylene diisocyanate concentration of 0.4 mass %, an isocyanate group concentration 1 of 18.5 mass %, a viscosity 1 at 25° C. of 670 mPa·s, and a color 1 of APHA 40. These values measured are shown in Table 4 as measured values before heat acceleration test.

Then, polyisocyanate composition (O) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 17.5 mass %, a viscosity 2 at 25° C. of 850 mPa·s, and a color 2 of APHA70. The measured values are shown as measured values after heat acceleration test in Table 4.

Example 16

Production of Polyisocyanate Composition (P)

A four-neck flask equipped with a mixer, a thermometer, a reflux pipe, and a nitrogen inlet tube was charged with 500 parts by mass of pentamethylene diisocyanate (a), 0.3 parts by mass of 2,6-di(tert-butyl)-4-methylphenol, 0.3 parts by mass of tris(tridecyl) phosphite, and 105 parts by mass of methoxypolyethyleneetherglycol having an average molecular weight of 400 and reaction was performed in a nitrogen atmosphere at 85° C. for 3 hours.

Then, 0.1 parts by mass of N-(2-hydroxypropyl)-N,N,N-trimethylammonium-2-ethylhexanoate was added as a trimerization catalyst. After performing reaction for 1 hour, 0.12 parts by mass of o-toluenesulfonamide was added (conversion rate of isocyanate group: 10 mass %). The obtained reaction solution was allowed to pass through a thin film distillation apparatus (degree of vacuum 0.093 KPa, temperature 150° C.) to remove unreacted pentamethylene diisocyanate, and 0.02 parts by mass of o-toluenesulfonamide relative to 100 parts by mass of the obtained composition was further added, thereby producing polyisocyanate composition (P).

The polyisocyanate composition (P) had a pentamethylene diisocyanate concentration of 0.1 mass %, an isocyanate group concentration 1 of 13.3 mass %, a viscosity 1 at 25° C. of 270 mPa·s, and a color 1 of APHA 20. These values measured are shown in Table 4 as measured values before heat acceleration test.

Then, polyisocyanate composition (P) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 12.9 mass %, a viscosity 2 at 25° C. of 310 mPa·s, and a color 2 of APHA20. The measured values are shown as measured values after heat acceleration test in Table 4.

Comparative Example 11

Production of Polyisocyanate Composition (Q)

Trimerization reaction was performed in the same manner as Example 16, except that pentamethylene diisocyanate (g) was used instead of pentamethylene diisocyanate (a). However, it was confirmed that the reaction velocity was low based on the isocyanate group concentration, and therefore 0.2 parts by mass of N-(2-hydroxypropyl)-N,N,N-trimethylammonium-2-ethylhexanoate was added. The reaction was continued for 2 hours, thereby producing polyisocyanate composition (Q).

The polyisocyanate composition (Q) had a pentamethylene diisocyanate concentration of 0.2 mass %, an isocyanate group concentration 1 of 11.7 mass %, a viscosity 1 at 25° C. of 380 mPa·s, and a color 1 of APHA 80. These values measured are shown in Table 4 as measured values before heat acceleration test.

Then, polyisocyanate composition (Q) was transferred to a metal-made container, and after nitrogen purge, the mixture was allowed to stand in a 40° C. oven for 14 days, thereby carrying out heat acceleration test. The polyisocyanate composition after the test had an isocyanate group concentration 2 of 10.9 mass %, a viscosity 2 at 25° C. of 490 mPa·s, and a color 2 of APHA120. The measured values are shown as measured values after heat acceleration test in Table 4.

TABLE 4

| | | Example and Comparative Example No. | | | |
|---|---|---|---|---|---|
| | | Example 13 | Comparative Example 8 | Example 14 | Comparative Example 9 |
| Polyisocyanate Composition | | J | K | L | M |
| Pentamethylenediisocyanate | | a | g | a | g |
| Pentamethylenediisocyanate Concentration (mass %) | | 0.2 | 0.3 | 0.6 | 0.7 |
| Before Heat Acceleration Test | Isocyanate Group Concentration1 (mass %) | 20.5 | 18.2 | 25.0 | 22.3 |
| | Viscosity 1 (mPa·s) | 190 | 270 | 2700 | 3780 |
| | Color 1 (—) | 20 | 70 | 20 | 60 |
| After Heat Acceleration Test | Isocyanate Group Concentration2 (mass %) | 20.1 | 17.0 | 24.2 | 20.9 |
| | Viscosity 2 (mPa·s) | 210 | 340 | 3110 | 4880 |
| | Color 2 (—) | 20 | 110 | 20 | 90 |
| Decrease in Isocyanate Group Concentration After Heat Acceleration Test (%) | | 2 | 7 | 3 | 6 |
| Increase in Viscosity After Heat Acceleration Test (%) | | 10 | 28 | 15 | 29 |
| Changes in Color After Heat Acceleration Test (Color 2 − Color 1) | | 0 | 40 | 0 | 30 |

| | | Example and Comparative Example No. | | | |
|---|---|---|---|---|---|
| | | Example 15 | Comparative Example 10 | Example 16 | Comparative Example 11 |
| Polyisocyanate Composition | | N | O | P | Q |
| Pentamethylenediisocyanate | | a | g | a | g |
| Pentamethylenediisocyanate Concentration (mass %) | | 0.3 | 0.4 | 0.1 | 0.2 |
| Before Heat Acceleration Test | Isocyanate Group Concentration1 (mass %) | 20.7 | 18.5 | 13.3 | 11.7 |
| | Viscosity 1 (mPa·s) | 480 | 670 | 270 | 380 |
| | Color 1 (—) | 20 | 40 | 20 | 80 |
| After Heat Acceleration Test | Isocyanate Group Concentration2 (mass %) | 20.3 | 17.5 | 12.9 | 10.9 |
| | Viscosity 2 (mPa·s) | 540 | 850 | 310 | 490 |
| | Color 2 (—) | 20 | 70 | 20 | 120 |
| Decrease Rate in Isocyanate Group Concentration After Heat Acceleration Test (%) | | 2 | 5 | 3 | 7 |
| Increase Rate in Viscosity After Heat Acceleration Test (%) | | 12 | 26 | 13 | 30 |
| Changes in Color After Heat Acceleration Test (Color 2 − Color 1) | | 0 | 30 | 0 | 40 |

Example 17

Production of Polyurethane Resin (A)

Polyisocyanate composition (A) produced in Example 7 and acrylic polyol (manufactured by Mitsui Chemicals, Inc. trade name: OLESTER Q666, hereinafter referred to as Q666.) were blended such that the equivalent ratio (NCO/OH) of the isocyanate group in the polyisocyanate composition relative to the hydroxyl group in the acrylic polyol was 1.0, and the mixture was stirred at 23° C. for 90 seconds, thereby producing a reaction mixture solution. Then, the reaction mixture solution was applied on a standard test plate (type: electroplated tin, in the following, referred to as test plate.) in conformity with JIS 63303, and thereafter, cured at 80° C. for 30 min, further at 110° C. for 1 hour, thereby producing a polyurethane resin (A) having a thickness of about 45 nm.

The obtained polyurethane resin (A) was allowed to stand in a room at 23° C. and a relative humidity of 55% for 7 days.

Example 18

Production of Polyurethane Resin (B)

Polyurethane resin (B) having a thickness of about 45 µm was produced in the same conditions and manner as in Example 17, except that polyisocyanate composition (E) produced in Example 11 was used instead of polyisocyanate composition (A).

The obtained polyurethane resin (B) was allowed to stand in a room at 23° C. and a relative humidity of 55% for 7 days.

Example 19

Production of Polyurethane Resin (C)

Polyurethane resin (C) having a thickness of about 45 µm was produced in the same conditions and manner as in Example 17, except that polyisocyanate composition (F) produced in Example 12 was used instead of polyisocyanate composition (A).

The obtained polyurethane resin (C) was allowed to stand in a room at 23° C. and a relative humidity of 55% for 7 days.

Example 20

Production of Polyurethane Resin (D)

Polyurethane resin (D) having a thickness of about 45 µm was produced in the same conditions and manner as in Example 17, except that plant derived polyol mainly composed of castor oil (manufactured by Mitsui Chemicals, Inc., trade name: TAKELAC U27, hereinafter referred to as U-27) was used instead of acrylic polyol Q666.

The obtained polyurethane resin (D) was allowed to stand in a room at 23° C. and a relative humidity of 55% for 7 days.

Comparative Example 12

Production of Polyurethane Resin (E)

Polyurethane resin (E) having a thickness of about 45 µm was produced in the same conditions and manner as in Example 17, except that polyisocyanate composition (G) produced in Comparative Example 5 was used instead of polyisocyanate composition (A).

The obtained polyurethane resin (E) was allowed to stand in a room at 23° C. and a relative humidity of 55% for 7 days.

Comparative Example 13

Production of Polyurethane Resin (F)

Polyurethane resin (F) having a thickness of about 45 µm was produced in the same conditions and manner as in Example 17, except that polyisocyanate composition (H) produced in Comparative Example 6 was used instead of polyisocyanate composition (A).

The obtained polyurethane resin (F) was allowed to stand in a room at 23° C. and a relative humidity of 55% for 7 days.

Comparative Example 14

Production of Polyurethane Resin (G)

Polyurethane resin (G) having a thickness of about 45 µm was produced in the same conditions and manner as in Example 17, except that polyisocyanate composition (1) produced in Comparative Example 7 was used instead of polyisocyanate composition (A).

The obtained polyurethane resin (G) was allowed to stand in a room at 23° C. and a relative humidity of 55% for 7 days.

Synthesis Example 1

Production of Polyol A

A four-neck flask equipped with a mixer, a thermometer, a reflux condenser, and a nitrogen inlet tube was charged with 100 parts by mass of butyl acetate as an organic solvent, and while conducting nitrogen replacement, the mixture was heated so that its temperature increased to 95° C. Thereafter, in the mixture, a mixture liquid of 34.3 parts of methyl methacrylate, 25.5 parts of butyl acrylate, 10.2 parts of 2-hydroxyethylacrylate, 30 parts by mass of isobornyl methacrylate as a polymerizable monomer, and 0.4 parts by mass of tert-butylperoxy-2-ethylhexanoate (hereinafter abbreviated as PBO) as a polymerization initiator were fed, taking four hours. After 1 hour and 2 hours of the completion of feed, 0.2 parts by mass of PRO was added. After the addition of PBO, reaction was performed for 2 hours, thereby producing polyol A.

Example 21

Production of Polyurethane Resin (H)

A polyol mixture in which polyol A produced in Synthesis Example 1 and U-27 were blended at a proportion of polyol A/U-27=78.9/21.1 (weight ratio) and polyisocyanate composition (A) produced in Example 7 were blended such that the equivalent ratio (NCO/hydroxyl group) of the isocyanate group in the polyisocyanate composition relative to the hydroxyl group in the polyol mixture was 1.0, and stirred at 23° C. for 90 seconds, thereby producing a reaction mixture liquid. Then, the reaction mixture liquid was applied to a standard test plate in conformity with JISG3303 (type: electroplated tin, hereinafter referred to as test plate), and thereafter, cured at 80° C. for 30 min, and further at 110° C. for 1 hour, thereby producing a polyurethane resin (H) having a thickness of about 45 µm.

The obtained polyurethane resin (H) was allowed to stand in a room at 23° C. and a relative humidity of 55% for 7 days.

Example 22

Production of Polyurethane Resin (I)

ALMATEX™ RE4788 (aqueous acrylic emulsion, solid content concentration 44.3 mass %, hydroxyl group value 86 mgKOH/g, Manufactured by Mitsui Chemicals Inc.) as a main component, and water were blended such that the solid content concentration after addition of a curing agent was 20 mass %, and while stirring with a magnetic stirrer, as a curing agent, polyisocyanate composition (P) produced in Example 16 was blended so that the equivalent ratio (NCO/hydroxyl group) of the isocyanate group in the curing agent relative to the hydroxyl group in the main component was 1.0.

The produced liquid blend was applied on an ABS plate and a PP plate such that the dried thickness was 20 μm. Then, the water was dried at 80° C. for 5 minutes, and thereafter, the liquid blend was cured in a room at 23° C. and a relative humidity of 55% for 48 hours, thereby producing polyurethane resin (I).

The surface of the ABS plate to which the polyurethane resin was applied was soaked with hot water of 75° C., and the surface conditions of the polyurethane resin after elapse of a predetermined time (after one day and 7 days) were observed.

The polyurethane resin on the PP plate was removed from the plate, and its weight was measured. The weight measured was regarded as an initial polyurethane resin weight. Then, a solution (hereinafter may be referred to as acetone/methanol solution) in which acetone and methanol were mixed at a weight ratio of 1 was put into a beaker, and the polyurethane resin was soaked therein, and allowed to stand for 4 hours. The SUS304 stainless steel wire net 300 mesh (hereinafter, may be abbreviated as stainless steel wire net) was weighed in advance, and the acetone/methanol solution in which the polyurethane resin was soaked was filtered. The stainless steel wire net containing undissolved polyurethane resin was dried at 40° C. for 1 hour, and then weighed, thereby calculating undissolved polyurethane resin weight.

Synthesis Example 2

Production of Polyol B 339.4 parts by mass of isophthalic acid, 110.9 parts by mass of ethylene glycol, 107.2 parts by mass of neopentyl glycol, 158.1 parts by mass of 1,6-hexanediol, and 0.21 parts by mass of zinc acetate were charged, and esterification reaction was performed at 200 to 220° C. for 6 hours. After distilling off a predetermined amount of water, 99.5 parts by mass of adipic acid was added, and esterification reaction was further performed for 7 hours. Thereafter, the pressure was reduced gradually, and transesterification was performed under 133 to 266 Pa at 200 to 230° C. for 4 hours, thereby producing polyesterpolyol having a number average molecular weight of 6,000. The produced polyesterpolyol was dissolved in 420 parts by mass of ethyl acetate, thereby producing polyol B having a solid content concentration of 60%.

Synthesis Example 3

Production of Polyol C 529.4 parts by mass of isophthalic acid, 128.8 parts by mass of ethylene glycol, and 302.4 parts by mass of neopentyl glycol were blended, and esterification reaction was performed under nitrogen stream at 180 to 220° C. After distilling off a predetermined amount of water, 214.8 parts by mass of sebacic acid was added, and esterification reaction was performed at 180 to 220° C., thereby producing polyester-polyol having a number average molecular weight of 2500. The total amount was dissolved in 428.6 parts by mass of ethyl acetate, thereby producing a solution having a solid content of 70%. To 643.3 parts by mass of the polyester-polyol, 49.6 parts by mass of isophorone diisocyanate was added in a nitrogen atmosphere, and urethane-forming reaction was performed at 77 to 80° C. for 3 hours. Thereafter, 0.10 parts by mass of stannous octoate was added as a catalyst, and the urethane-forming reaction was continued for further 3 hours, thereby producing polyurethane polyol having a number average molecular weight of 10,000. 307.0 parts by mass of ethyl acetate was added thereto, thereby producing polyol C having a solid content concentration of 50%.

Example 23

Production of Polyurethane Resin (J)

1 part by mass of polyisocyanate composition (A) produced in Example 7 and 15 parts by mass of polyol B were mixed, thereby preparing an adhesive. Then, the adhesive was applied under normal temperature using a bar coater to a nylon film (15 μm thickness) and the solvent was volatilized so that the solid content thereof was 3.5 g/m². Thereafter, the surface to which the adhesive was applied was bonded to a corona treatment side of an unstretched polyethylene film (40 μm thickness, one side subjected to corona treatment), and matured at 40° C. for 5 days to cure the adhesive, thereby producing a polyurethane resin (1) of a two-layer composite film. Normal adhesive strength of the obtained two-layer composite film polyurethane resin (J) was measured. Then, the end of the two-layer composite film polyurethane resin (J) was heat-sealed to produce a pouch of 130 mm×170 mm, and the pouch was charged with 100 ml of a mixture of water/salad oil=10/1 (volume ratio) as contents. Then, the charged pouch was subjected to boiling water sterilization at 100° C. for 30 minutes. Thereafter, the contents were taken out and adhesive strength after boiling water sterilization was measured.

Example 24

Production of Polyurethane Resin (K)

A two-layer composite film polyurethane resin (K) was produced in the same conditions and manner as in Example 23, except that 1 part by mass of polyisocyanate composition (A) produced in Example 7 and 20 parts by mass of polyol C were mixed.

Normal adhesive strength, pouch appearance after boiling water sterilization, and adhesive strength after boiling water sterilization were measured in the same manner as in Example 23.

Example 25

Synthesis of Polyurethane Resin (L)

In a nitrogen atmosphere, a reactor equipped with an impeller, a thermometer, and a water-cooling condenser was charged with 126.4 parts by mass of polytetramethylene ether glycol (manufactured by Hodogaya Chemical Co., LTD trade name: BIO PTG2000SN, hereinafter referred to as PTMEG) that had been subjected to a reduced-pressure dehydration treatment in advance having a number average molecular weight of 2000 and 16.6 parts by mass of pentamethylene diisocyanate (a) produced in Example 1 so that the equivalent ratio (NCO/hydroxyl group) of the isocyanate group in pentamethylene diisocyanate relative to the hydroxyl group in PTMEG was 1.7 and the temperature was increased to 70° C.

Then, while stirring, reaction was performed at 70° C. for 1 hour, and then thereafter, 0.003 parts by mass of NEOSTANN U-600 (manufactured by Nitto Kasei Co., Ltd.) was added as a catalyst.

Then, reaction was performed until the isocyanate group content was 2.6 mass % at the same temperature, thereby producing an isocyanate group-terminated polyurethane prepolymer (hereinafter abbreviated as prepolymer).

Then, 810.3 parts by mass of N,N'-dimethylacetamide (manufactured by Wako Pure Chemical Industries. Ltd., organic synthesis grade) (hereinafter abbreviated as DMAc) in which molecular sieves 4 A were soaked in advance was added to the prepolymer whose temperature was decreased to 50° C. or less so that the prepolymer concentration was 15 mass %, thereby dissolving the prepolymer.

Thereafter, a 42.0 mass % DMAc solution (hereinafter abbreviated as amine solution) of an amine mixture of 4.34 parts by mass of pentamethylenediamine (a) obtained in Production Example 1 and 0.33 parts by mass of diethylamine (hereinafter abbreviated as DEA) was added dropwise, so that the temperature of the DMAc solution of the prepolymer does not exceed 30° C., thereby performing chain extension reaction. The amino group concentration ratio of pentamethylenediamine (a) to DEA was 95 mol %:5 mol %, and the equivalent ratio of the amino group in the amine mixture relative to the isocyanate group in the DMAc solution of the prepolymer was 1.001.

After dropping the amine solution, the temperature was increased to 50° C., and reaction was performed for 2 hours at the same temperature, thereby producing a DMAc solution of polyurethane resin (L).

Then, on a glass plate, the DMAc solution of polyurethane resin (L) was applied so that the film thickness after drying was 100 μm, and the DMAc was distilled off in a nitrogen atmosphere at 40° C. for 24 hours under normal pressure.

Then, after the temperature was increased to 60° C., drying was performed for 5 hours at the same temperature. Furthermore, the pressure was reduced at the same temperature for 7 hours, thereby distilling off DMAc and producing a polyurethane resin (L).

Example 26

Synthesis of Polyurethane Resin (M)

A four-neck flask equipped with a mixer, a thermometer, a reflux pipe, and a nitrogen inlet tube was charged with 100 parts by mass of polytetramethylene ether glycol (manufactured by Hodogaya Chemical Co., LTD., trade name: BIO PTG2000SN, biomass concentration: 95%, hereinafter abbreviated as PTMEG) having a number average molecular weight of 2000 and subjected to a reduced-pressure dehydration treatment in advance and 23.1 parts by mass of pentamethylene diisocyanate (a) produced in Example 1 such that the equivalent ratio (NCO/hydroxyl group) of the isocyanate group in pentamethylene diisocyanate relative to the hydroxyl group in PTMEG was 2.0, and in a nitrogen atmosphere, reaction was performed at 80° C. until the isocyanate group content was 6.8 mass %, thereby producing an isocyanate group-terminated polyurethane prepolymer (hereinafter referred to as prepolymer).

Then, 123 parts by mass of a prepolymer adjusted to 80° C. in advance, 0.4 parts by mass of a heat-resistant stabilizer (Ciba Specialty Chemicals, trade name: IRGANOX 1135), 0.002 parts by mass of stannous octoate (manufactured by API Corporation, trade name: Stanoct) as a catalyst, and 0.001 parts by mass of an antifoaming agent (manufactured by BYK Japan KK, trade name: BYK-088) were introduced into a stainless steel container, and mixed while stirring at 700 rpm using Three-One Motor (manufactured by SHINTO Scientific Co., ltd., trade name: HEIDON FBL3000) for about 1 min. Then, 7.6 parts by mass of 1,3-propanediol (manufactured by Du Pont Kabushiki Kaisha, trade name: Bio-PDO, biomass concentration: 100%, hereinafter abbreviated as 1,3-PDO) adjusted to 80° C. in advance as a chain extender was added. After stirring sufficiently for about additional 2 minutes until the entire mixture was homogenous, vacuum defoaming was immediately performed, thereby removing foams in the mixture liquid. The mixture liquid was poured into a sheet mold to which a mold release agent (manufactured by Miyoshi Oil & Fat Co., Ltd., trade name: MIRAX RS-102) was applied in advance, whose temperature was controlled to 100° C., and which has a thickness of 2 mm with care not to include bubbles, and reaction was performed at 100° C. for 22 hours, thereby producing polyurethane resin (M). Thereafter, the obtained polyurethane resin (M) was removed from the mold, and allowed to stand in a room having a temperature of 23° C. and a relative humidity of 55% for 7 days. Pentamethylene diisocyanate (a) had a biomass concentration of 71% as measured in conformity with the method of ASTMD6866B. Based on the material biomass concentration, the biomass concentration of polyurethane resin (M) was calculated to be 90.8%.

Example 27

Production of Polyurethane Resin (N)

95 parts by mass of an amorphous polytetramethylene ether glycol (manufactured by Asahi Kasei Fibers Corporation, trade name: PTXG-1800) adjusted to 80° C. 5 parts by mass of polyoxypropylene glycol having a number average molecular weight of 1800 (hydroxyl group value 31.2 mgKOH/g) produced by addition polymerization of propyleneoxide to dipropylene glycol using a phosphazenium compound as a catalyst in conformity with the method described in Example 2 of Japanese Patent No. 3905638, 10.3 parts by mass of polyisocyanate composition (A) obtained in Example 7, 0.01 parts by mass of dibutyltin dilaurate (IV)(manufactured by Wako Pure Chemical Industries, Ltd.) as a catalyst, and 0.005 parts by mass of an antifoaming agent (manufactured by BYK Japan KK, trade name: BYK-088) were introduced into a stainless steel container so that the equivalent ratio (NCO/hydroxyl group) of the isocyanate group to the hydroxyl group was 0.54, and mixed while stirring at 700 rpm using Three-One Motor (manufactured by SHINTO Scientific Co., ltd., trade name: HEIDOM FBL3000) for about 1 min. A reduced-pressure defoaming was immediately performed to remove the bubbles in the mixture liquid, and then the mixture liquid was poured into a sheet mold having a thickness of 2 mm, a block mold having a thickness of 15 mm, and a button mold having a thickness of 12.5 mm and a diameter of 29 mm to which a mold release agent (manufactured by Miyoshi Oil & Fat Co., Ltd., trade name: MIRAX RS-102) was applied in advance and whose temperatures were adjusted to 80° C., with care not to include bubbles, and reaction was performed at 80° C. for 5 hours, thereby producing polyurethane resin (N).

Thereafter, the obtained polyurethane resin (N) was removed from the mold, and allowed to stand in a room having a temperature of 23° C. and a relative humidity of 55% for 7 days.

Comparative Example 15

Production of Polyurethane Resin (O)

Polyurethane resin (O) was obtained in the same conditions and manner as in Example 27, except that the equivalent ratio (isocyanate group/hydroxyl group) of the isocyanate group to the hydroxyl group was set to 0.54, and 12.2 parts by mass of TAKENATE D-170N (Manufactured by Mitsui Chemicals Inc.) was used instead of polyisocyanate composition (A). Thereafter, the obtained polyurethane resin (O) was removed from the mold, and allowed to stand in a room having a temperature of 23° C. and a relative humidity of 55% for 7 days.

Physical Property Evaluation

The Martens hardness, tensile strength, solvent resistance, surface conditions, gel fraction, adhesive strength, pouch appearance after boiling water sterilization, 100% deformation stress, tensile strength 2, elongation at break, residual strain after repeated elongation deformation, hardness, tensile strength 3, elongation at break 2, compression set, softening temperature, and tackiness of the polyurethane resins (hereinafter abbreviated as coating) obtained in Examples and Comparative Examples were measured by the following method. The results are shown in Tables 5 to 11.

<Martens Hardness (Unit: N/mm$^2$)>

The Martens hardness (HMT 115) of the coating that was in close contact with the test plate was measured under the following conditions using a Dynamic Ultra Micro Hardness Tester (manufactured by Shimadzu Corporation, DUH-211). Type of indenter: Triangular 115, Test mode: Load-unload test, Test Force: 10.00 mN, Loading Rate: 3.0 mN/sec, Holding Time: 10 sec.

<Tensile Strength (TS)(Unit: MPa)>

The coating was punched out into a size of a width of 1 cm, and a length of 10 cm with a dumbbell. Then, this test sample was subjected to tensile test using tensile compression tester (manufactured by INTESCO co. Ltd. Model 205N) with the following conditions: 23° C., under an atmosphere of a relative humidity of 55%, tensile speed 10 mm/min, distance between chucks 50 mm. The tensile strength (TS) was measured in this manner.

<Solvent Resistance (Unit: Times)>

A cotton swab sufficiently impregnated with a test solution was placed on the coating that is in close contact with the test plate, and allowed to go back and forth in a distance of about 1 cm while a constant load is applied. The above operation was repeated several times, and the test was terminated at the point when a damage was found on the coating. The outbound and the inbound was counted as once (back and forth), and the number until a damage is found on the coating is regarded as SOLVENT RESISTANCE. The test solutions used were ethyl acetate and methyl ethyl ketone.

<Surface Conditions>

The polyurethane resin was soaked in hot water of 75° C., and the surface conditions thereof after one day and after seven days were evaluated based on the following criteria.
Good: No change was observed.
Average: Slight whitening was confirmed.
Poor: Significant whitening was confirmed.

<Gel Fraction (Unit: Mass %)>

The gel fraction was calculated by the following formula.

Gel Fraction=undissolved polyurethane resin weight/initial polyurethane resin weight×100

<Adhesive Strength (Unit: N/15 mm)>

A test piece having a length of 100 mm and a width of 15 mm was cut out from the composite film, and the adhesive strength was measured conducting T-type peel test using a tensile tester (manufactured by INTESCO co., Ltd model 201B) under the conditions of the following: at 23° C. and under an atmosphere of a relative humidity of 55%, at a peeling speed of 300 mm/min.

<Pouch Appearance after Boiling Water Sterilization>

Pouch appearance after Boiling Water Sterilization was evaluated based on the following criteria.
Good: No change was observed.
Poor: Change was observed.

<100% Deformation Stress (Unit: MPa)>

The polyurethane resin was punched out into a size of a width of 1 cm, and a length of 10 cm with a dumbbell.

Then, this test sample was subjected to tensile test using tensile tester (manufactured by INTESCO co., Ltd., Model 205N) with the following conditions: 23° C. under an atmosphere of a relative humidity of 55%, tensile speed 300 mm/min, distance between chucks 30 mm. At the time of 100% deformation, that is, the stress when the distance between the chucks was 60 mm was regarded as 100% deformation stress.

<Tensile Strength 2 (Unit: MPa)>

Tensile test was performed under the same conditions with the 100% deformation stress, measuring tensile strength 2.

<Elongation at Break (Unit: %)>

Tensile test was performed under the same conditions as the 100% deformation stress, measuring elongation at break.

<Residual Strain after Repeated Elongation Deformation (Unit: %)>

The polyurethane resin was punched out into a size of a width of 1 cm, and a length of 10 cm with a dumbbell.

Then, this test sample was subjected to tensile test using a tensile compression tester (manufactured by Simadzu Corporation, AG-X.) with the following conditions: 23° C., under an atmosphere of a relative humidity of 55%. To be more specific, a film having a sample length (L1) of 30 mm in the tensile direction was elongated at a tensile speed of 500 mm/min to 300%, and this operation was repeated to a total of 5 times.

After stretching to 300% at the fifth time, the film was allowed to stand as is for 30 seconds. Then, the sample length (L2) was measured when the sample was recovered from the stretching until no stress was detected.

Then, using formula below, the residual strain after repeated elongation deformation was calculated.

$$\{(L2-L1)/L1\}\times 100$$

<Tensile Strength 3 (Unit: MPa)>

A polyurethane resin obtained by using a sheet mold was punched out with a dumbbell of JIS-3. Then, a tensile test was conducted using a tensile tester (manufactured by A & D Company, Limited, Model: RIG-1310) with the following conditions: 23° C., under an atmosphere of a relative humidity of 55%, a tensile speed of 500 mm/min, and a distance between the chucks of 20 mm. Tensile Strength 3 was measured in this manner.

<Elongation at Break 2 (Unit: %)>

The tensile test was conducted in the same manner as in Tensile strength 3, thereby measuring elongation at break 2.

<Hardness (Unit: %)>

Type C hardness test was conducted in conformity with JIS K7312 using a polyurethane resin obtained by using a block mold.

<Total Luminous Transmittance (Unit: %)>

The total luminous transmittance was measured using a polyurethane resin obtained by using a sheet mold in conformity with JIS K7105 using a Haze Meter (manufactured by Nippon Denshoku Industries Co., Ltd., Model: NDH2000, light source: $D_{65}$).

<Haze (Unit: %)>

The haze was measured using a polyurethane resin obtained by using a sheet mold under the same conditions as in the measurement of the total luminous transmittance.

<Tear Strength (Unit: kN/m)>

A polyurethane resin obtained by using a sheet mold was punched out with a dumbbell of JIS-B. Then, a tensile test was conducted under the same conditions as in the measurement of tensile strength 3 to measure a tear strength.

<Compression Set (Unit: %)>

A compression set was measured using a polyurethane resin obtained by using a button mold in conformity with JIS K6262 with the following conditions: measurement temperatures of 23° C. and 70° C., under an atmosphere of a relative humidity of 55%, compression proportion of 25%, and a holding time of 22 hours.

<Softening Temperature (Unit: ° C.)>

A polyurethane resin obtained by using a sheet mold was punched out to give a size of a width of 5 mm, and a length of 10 cm with a dumbbell. Then, a measurement was conducted using a dynamic viscoelasticity apparatus (manufactured by TA Instruments, model: RSA-III) under the following conditions: in a nitrogen atmosphere, tensile mode (Auto Tension, Auto Strain Control), measurement temperature from −100 to 200° C., temperature rising speed of 3° C./min, and at a frequency of 10 Hz. The temperature at which the tangent lines of the dynamic region and the flat region in high-temperature-side storage modulus cross was regarded as a softening temperature.

<Tackiness>

A polyurethane resin obtained by using a sheet mold was cut out to a square of 5 cm. The obtained polyurethane resin pieces were arranged on a PP plate, and allowed to stand for one day in a room having a temperature of 23° C. and a relative humidity of 55%. Then, the PP plate was reversed upside down, and occurrence/nonoccurrence of fallout of the polyurethane resin pieces within 1 min was observed. The results were evaluated as tackiness.
Good: the polyurethane resin pieces fell off within 1 minute.
Poor: the polyurethane resin pieces did not fall off within 1 minutes.

TABLE 6

| | | | Example No. Example 21 |
|---|---|---|---|
| Polyurethane Resin | | | H |
| Polyisocyanate Composition | | | A |
| Physical Property Evaluation | Martens hardness (N/mm²) | | 158 |
| | Solvent Resistance (Times) | Ethyl Acetate | 720 |
| | | Methyl Ethyl Ketone | 260 |

TABLE 7

| | | | Example No. Example 22 |
|---|---|---|---|
| Polyurethane Resin | | | I |
| Polyisocyanate Composition | | | P |
| Physical Property Evaluation | Surface Conditions | After One Day | Good |
| | | After Seven Days | Good |
| | Gel Fraction (%) | | 95 |

TABLE 8

| | | Example No. | |
|---|---|---|---|
| | | Example 23 | Example 24 |
| Polyurethane Resin | | J | K |
| Polyisocyanate Composition | | A | A |
| Physical Property Evaluation | Normal adhesive strength (N/15 mm) | 10.0 | 9.4 |
| | Pouch appearance after Boiling Water Sterilization | Good | Good |
| | Adhesive Strength after Boiling Water Sterilization (N/15 mm) | 9.5 | 8.7 |

TABLE 9

| | | Example No. Example 25 |
|---|---|---|
| Polyurethane Resin | | L |
| Physical Property Evaluation | 100% Deformation Stress(MPa) | 3.0 |
| | Tensile Strength 2 (MPa) | 40 |
| | Elongation at Break(%) | 900 |
| | Residual Strain After Repeated Elongation Deformation(%) | 30.1 |

TABLE 5

| Example and Comparative Example No. | | Example 17 | Example 18 | Example 19 | Example 20 |
|---|---|---|---|---|---|
| Polyurethane Resin | | A | B | C | D |
| Polyisocyanate Composition | | A | E | F | A |
| Physical Property Evaluation | Martens hardness (N/mm²) | 168 | 164 | 148 | 36 |
| | Tensile Strength (MPa) | 54 | 52 | 47 | 25 |
| | Solvent Resistance (Times) Ethyl Acetate | 800 | 780 | 590 | 670 |
| | Methyl Ethyl Ketone | 290 | 280 | 230 | 300 |

| Example and Comparative Example No. | | Comparative Example 12 | Comparative Example 13 | Comparative Example 14 |
|---|---|---|---|---|
| Polyurethane Resin | | E | E | G |
| Polyisocyanate Composition | | G | H | I |
| Physical Property Evaluation | Martens hardness (N/mm²) | 129 | 136 | 124 |
| | Tensile Strength (MPa) | 42 | 43 | 38 |
| | Solvent Resistance (Times) Ethyl Acetate | 390 | 400 | 340 |
| | Methyl Ethyl Ketone | 180 | 190 | 140 |

TABLE 10

| | Example No. Example 26 |
|---|---|
| Polyurethane Resin | M |
| Physical Property Evaluation — Tensile Strength 3 (MPa) | 30 |
| Elongation at Break2 (%) | 500 |

TABLE 11

| | | Example No. | Comparative Example No. |
|---|---|---|---|
| | | Example 27 | Comparative Example 15 |
| Polyurethane Resin | | N | O |
| Polyisocyanate Composition | | A | TAKENATE D-170N |
| Physical Property Evaluation | Hardness (C) | 15 | 18 |
| | Appearance | Transparent | Non-transparent |
| | Total Luminous Transmittance (%) | 93.3 | 91.6 |
| | Haze (%) | 5.7 | 47.1 |
| | Tensile Strength3 (MPa) | 0.9 | 0.4 |
| | Elongation at Break2 (%) | 810 | 580 |
| | Tear Strength (kN/m) | 2.2 | 1.7 |
| | Compression 23° C. | 0.4 | 1.4 |
| | Set (%) 70° C. | 0.9 | 1.8 |
| | Softening Temperature (° C.) | 110 | 93 |
| | Tackiness | Good | Poor |

Example 28

Using pentamethylene diisocyanate (a) described in Example 1 and pentamethylenediamine (a) described in Production Example 1, vapor deposition polymerization reaction was performed using a vacuum treatment device described in Japanese Unexamined Patent Publication No. 2008-56790. A glass substrate (manufactured by Corning Incorporated, trade name: EAGLE XG) with transparent conductive film (ITO) was used as a substrate, and the temperature was adjusted to 20° C. Meanwhile, setting pentamethylenediamine (a) to 20° C. and pentamethylene diisocyanate (a) to 70° C., and controlling their pressures to 20 Pa, they were evaporated simultaneously. Pentamethylenediamine (a) and pentamethylene diisocyanate (a) were supplied such that their stoichiometric ratio was 1:1. The temperature in the chamber at this time was controlled to 20° C.

After forming a polyurea resin film on the substrate, the temperature was increased to 80° C. in a nitrogen atmosphere at a speed of 10° C./min, and heated for 10 minutes, thereby producing a polyurea resin having a thickness of 1 μm.

The polyurea resin film was subjected to corona discharge at a room temperature and a voltage of −10 kV, thereby subjecting the polyurea resin film to poling process.

A piezoelectric $d_{33}$ constant $d_{33}$ was measured by using a Berlin court method $d_{33}$ meter manufactured by Channel Products Inc., with a frequency of 20 Hz, the results showed the maximum of $30 \times 10^{-12}$ C/N.

Comparative Example 16

A polyurea resin was obtained in the same manner as in Example 28 except that pentamethylene diisocyanate (j) described in Comparative Example 4 was used instead of pentamethylene diisocyanate (a). The polyurea resin has a piezoelectric d constant $d_{33}$ at maximum of $20 \times 10^{-12}$ C/N.

The results show that by using the pentamethylene diisocyanate of the present invention, the piezoelectric d constant $d_{33}$ of a polyurea resin obtained by reaction with a polyamine, for example, pentamethylenediamine improves.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

A pentamethylene diisocyanate, a production method thereof, and a polyisocyanate composition of the present invention are useful for a polyurethane resin material and a production method thereof, and the polyurethane resin of the present invention can be widely used in various industrial fields.

The invention claimed is:

1. A pentamethylene diisocyanate obtained by phosgenating pentamethylenediamine or its salt obtained by a biochemical method, wherein the pentamethylene diisocyanate contains 5 to 200 ppm of a compound represented by the general formula (1) below and a compound represented by the general formula (2) below in total:

[Chemical Formula 1]

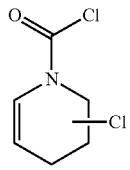

(1)

[Chemical Formula 2]

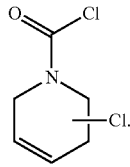

(2)

2. The pentamethylene diisocyanate according to claim 1, obtained by: preparing an aqueous solution of pentamethylenediamine or its salt by a biochemical method, extracting the pentamethylenediamine or its salt from the aqueous solution, and phosgenating the extracted pentamethylenediamine or its salt to produce a pentamethylene diisocyanate, and heating the pentamethylene diisocyanate in the presence of an inactive gas at 180° C. to 245° C., and thereafter, purifying the pentamethylene diisocyanate by distillation.

3. The pentamethylene diisocyanate according to claim 2, obtained by heating the pentamethylene diisocyanate in the presence of a phosphorus-containing compound.

4. The pentamethylene diisocyanate according to claim 2, wherein the pentamethylene diisocyanate is heated at 190° C. to 245° C.

* * * * *